United States Patent
Van Meir et al.

(10) Patent No.: US 8,071,795 B2
(45) Date of Patent: Dec. 6, 2011

(54) HIF INHIBITORS

(75) Inventors: Erwin G Van Meir, Tucker, GA (US);
Kyriacos Nicolaou, La Jolla, CA (US)

(73) Assignees: Emory University, Atlanta, GA (US);
Scripps Research Institute, LaJolla, CA (US)

(*) Notice: Subject to any disclaimer, the term of this patent is extended or adjusted under 35 U.S.C. 154(b) by 809 days.

(21) Appl. No.: 11/997,809

(22) PCT Filed: Aug. 25, 2006

(86) PCT No.: PCT/US2006/033286
§ 371 (c)(1),
(2), (4) Date: Apr. 21, 2008

(87) PCT Pub. No.: WO2007/025169
PCT Pub. Date: Mar. 1, 2007

(65) Prior Publication Data
US 2008/0226622 A1    Sep. 18, 2008

Related U.S. Application Data

(60) Provisional application No. 60/711,602, filed on Aug. 25, 2005.

(51) Int. Cl.
*C07D 309/30* (2006.01)
(52) U.S. Cl. ..................................................... 549/292
(58) Field of Classification Search .................. 549/292
See application file for complete search history.

(56) References Cited

FOREIGN PATENT DOCUMENTS

WO    2004/087066        10/2004
WO    2004/087066 A2    10/2004

OTHER PUBLICATIONS

International Search Report and Written Opinion, dated Jul. 29, 2008.
Nicolaou, et al. Natural Product-like Combinatorial Libraries Based on Privileged Structures. 2. Construction of a 10000-Membered Benzopyran Library by Directed Split-and-Pool Chemistry Using NanoKans and Optical Encoding, J. Am. Chem. Soc. vol. 122, pp. 9954-9967 (2000).
Giatromanolaki , A. et al., 2001, "Relation of hypoxia inducible factor 1 alpha and 2 alpha in operable non-small cell lung cancer to angiogenic/molecular profile of tumours and survival", Br J Cancer, 85(6), pp. 881-890.
Pugh, C., et al., 2001, "Hypoxia and oxidative stress in breast cancer. Hypoxia signalling pathways;" Breast Cancer Res., 3(5), pp. 313-317.
Semenza, Gregg, 2002, entitled "Involvement of hypoxia-inducible factor 1 in human cancer" first sentence of col. 2, p. 80, Intern Med., 41(2), pp. 79-83.
Zhong, H., et al., 1999, "Overexpression of hypoxia-inducible factor 1alpha in common human cancers and their metastase", Cancer Res., 59(22), p. 5830.
Zhong, H., et al., 2001, "Hypoxia-inducible factor 1alpha and 1beta proteins share common signaling pathways in human prostate cancer cells", Biochem Biophys Res Commun., 284(2), pp. 352-356.

(Continued)

*Primary Examiner* — Janet L. Andres
*Assistant Examiner* — Raymond Covington
(74) *Attorney, Agent, or Firm* — Emory Patent Group; James M. Mason; Susanne Hollinger

(57) ABSTRACT

HIF-1 inhibitors and methods of use thereof are provided.

11 Claims, 37 Drawing Sheets

OTHER PUBLICATIONS

Narita et al., "Identification of a Novel Small Molecule HIF-1α Translation Inhibitor," Clinical Cancer Research, 15(19): 6128-6136 (2009).

Nicolaou et al., "Combinatorial synthesis through disulfide exchange: discovery of potent psammaplin A type antibacterial agents active against methicillin-resistant *Staphylococcus aureus* (MRSA)," Chemistry—A European Journal, 7(19): 4280-4295 (2001).

Tan et al., "Identification of a Novel Small-Molecule Inhibitor of the Hypoxia-Inducible Factor 1 Pathway," Cancer Research, 65(2):605-612 (2005).

Formula A'

Formula B'

Formula C'

Formula D'

Formula K

Formula L

Formula M

Formula T

Formula U

Formula V

Formula W

Formula X

Formula E'

Formula F'

Formula G'

Formula H'

Formula I'

Formula J'

Formula K'

Formula L'

Formula M'

Formula N'

Formula O'

Formula P'

Formula Q'

Formula R'

Formula S'

Formula T'

Formula U'

Formula V'

Formula W'

Formula X'

Formula C'/X2'

Formula C/X3"

Formula C'/X4'

Formula C'/X5'

Formula C'/X6'

Formula C'/X7'

Formula C'/X8'

Formula D'/X7'

Formula D'/X1'

FIG. 22

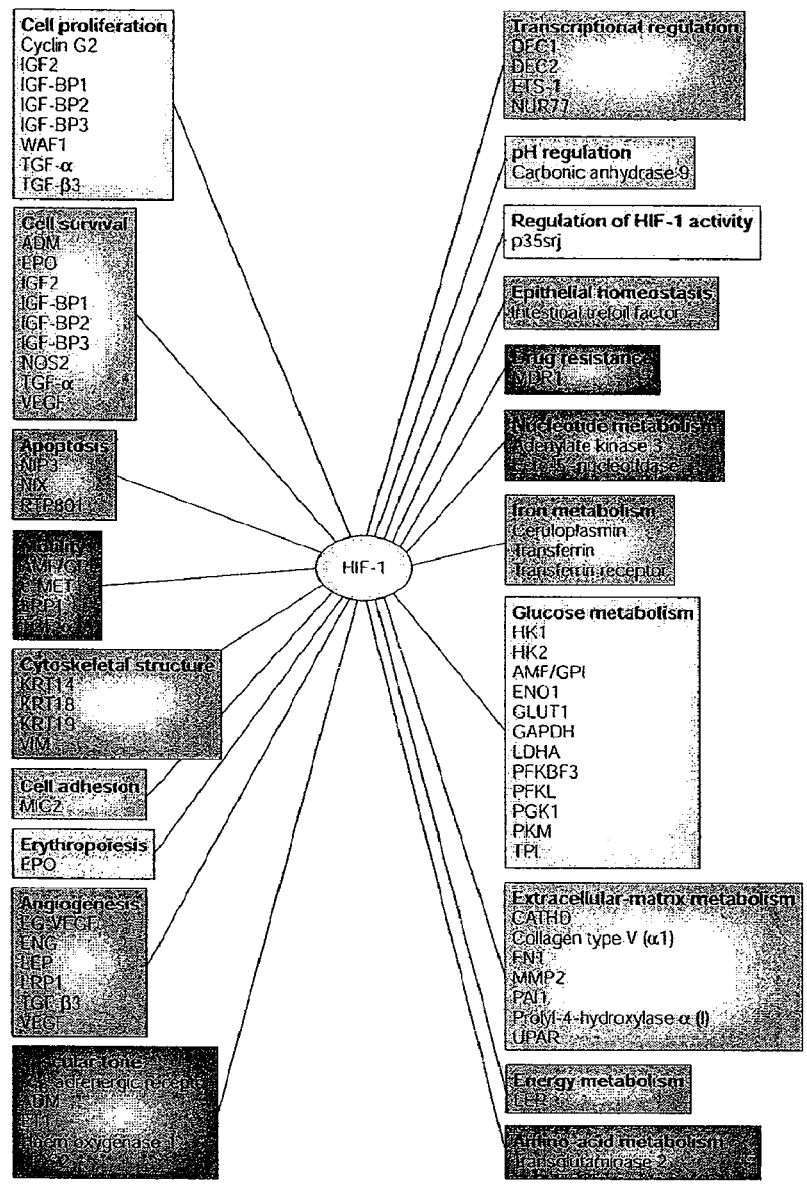

Genes that are transcriptionally activated by HIF-1. Genes that are involved in many processes are transcriptionally activated by HIF-1. ADM, adrenomedullin; ALDA, aldolase A; ALDC, aldolase C; AMF, autocrine motility factor; CATHD, cathepsin D; EG-VEGF, endocrine-gland-derived VEGF; ENG, endoglin; ET1, endothelin-1; ENO1, enolase 1; EPO, erythropoietin; FN1, fibronectin 1; GLUT1, glucose transporter 1; GLUT3, glucose transporter 3; GAPDH, glyceraldehyde-3-P-dehydrogenase; HK1, hexokinase 1; HK2, hexokinase 2; IGF2, insulin-like growth-factor 2; IGF-BP1, IGF-factor-binding-protein 1; IGF-BP2, IGF-factor-binding-protein 2; IGF-BP3, IGF-factor-binding-protein 3; KRT14, keratin 14; KRT18, keratin 18; KRT19, keratin 19; LDHA, lactate dehydrogenase A; LEP, leptin; LRP1, LDL-receptor-related protein 1; MDR1, multidrug resistance 1; MMP2, matrix metalloproteinase 2; NOS2, nitric oxide synthase 2; PFKBF3, 6-phosphofructo-2-kinase/fructose-2,6-biphosphatase-3; PFKL, phosphofructokinase L; PGK 1, phosphoglycerate kinase 1; PAI1, plasminogen-activator inhibitor 1; PKM, pyruvate kinase M; TGF-α, transforming growth factor-α; TGF-β3, transforming growth factor-β3; TPI, triosephosphate isomerase; VEGF, vascular endothelial growth factor; UPAR, urokinase plasminogen activator receptor; VEGFR2, VEGF receptor-2; VIM, vimentin.

HIF INHIBITORS

CROSS REFERENCE TO RELATED APPLICATION

This application claims priority to "HIF INHIBITORS," having serial number PCT/US2006/033286, filed on Aug. 25, 2006. This application also claims priority to and benefit of U.S. Provisional Patent entitled "HIF-1 Inhibitors", having Application No. 60/711,602 filed on Aug. 25, 2005, which is incorporated by reference in its entirety.

STATEMENT REGARDING FEDERALLY FUNDED RESEARCH

This invention was made in part with government support under Grant No. CA 46446 awarded by the National Institutes of Health. The government has certain rights in the invention.

TECHNICAL FIELD

The present disclosure is generally directed to inhibitors of the Hypoxia Inducible Factor (HIF-1) pathway and methods of their use.

BACKGROUND

Despite significant progress in cancer treatments, a number of malignant tumors remain deadly diseases. Among those are central nervous system (CNS) tumors, which are the leading cause of cancer death for people under 35 years of age. The incidence of primary brain tumors increased by more than 25% between 1979-1991 and the death rate increased by 15%. Finding novel treatments for brain tumors is currently a major challenge, especially for malignant gliomas, which have the highest death rates (>13,000 deaths/yr in the United States). Patients with GBM have an average survival of 10-12 months and a 2-yr survival rate of less than 10%, irrespective of therapy.

Cancer can be a fatal disease, in part, because cancer can spread or metastasize throughout an organism. Metastasis plays a major role in the morbidity and mortality of breast cancer. Breast cancer metastasizes in a stereotypical pattern resulting in lesions found in the lymph node, lung, liver, and bone marrow. Generally, cancer cells lose differentiated properties, proper tissue compartmetalization, cell-cell attachment as well as obtain altered cell substratum attachment, altered cytoskeletal organization, cell locomotion, and the ability to survive at distant sites.

Hypoxia is a major hindrance to effective solid tumor therapy. The microenvironment of rapidly growing solid tumors is associated with increased energy demand and diminished vascular supply, resulting in focal areas of prominent hypoxia, regions with reduced oxygen tensions. Tissue oxygen electrode measurements taken in cancer patients showed a median range of oxygen partial pressure of 10 to 30 mmHg, with a significant proportion of readings below 2.5 mmHg, whereas those in normal tissues ranged from 24 to 66 mg. In the absence of oxygen, which is the most electron-affinic molecule in cells and reacts chemically with the fundamental biological lesion produced by ionizing radiation, radiotherapy is severely compromised in its ability to kill hypoxic tumor cells. On the other hand, hypoxia (and possibly hypoxia-associated deficiencies in other nutrients such as glucose) causes tumor cells to stop or slow their rate of progression through the cell cycle. Because most anticancer drugs are more effective against rapidly proliferating cells than slowly or non-proliferating cells, this slowing of cell proliferation leads to decreased cell killing. Chemotherapy is further affected by hypoxia as chemotherapeutic drugs are delivered systemically and the diffusion of these into the tumor makes the hypoxic regions exposed to less drug than the oxygenated cells proximal to the vessels. Moreover, the multidrug resistance (MDR1) gene product P-glycoprotein is induced by ambient hypoxia.

Tumor hypoxia increases malignant progression and metastasis by promoting angiogenesis through induction of both pro-angiogenic proteins such as VEGF and metabolic adaptation through elevation of glycolytic enzymes. Hypoxia also generates selective pressure for cells to acquire genetic alterations (e.g., TP53, K-ras), that will circumvent hypoxia-induced apoptosis.

An essential component of tumor growth is angiogenesis. Tumors need to disrupt physiological controls over angiostasis to initiate neovascularization, a process triggered by the release of hypoxia-inducible angiogenic factors by nascent tumors. Angiogenesis is a stepwise process during the grade II-IV progression of astrocytoma. First, new blood vessels appear in low grade astrocytoma (II) followed by an increase in vessel density in anaplastic astrocytoma (III). Then, with the transition to GBM (IV), extensive micro-vascular proliferation leading to abnormal vessels occurs. Hypoxia is an integral component of astrocytoma progression and increases with grade. Most $PO_2$ readings are in the 0.5-2.5% range, although severe hypoxia (0.1% range) has also been reported. Hypoxia-mediated angiogenesis is most prevalent in the transition from grade III to IV tumors. Hypoxia occurs at the leading/actively growing edge of tumors where it leads to the florid microvascular proliferation characteristic of GBM. The combination of hypoxia/micro-vascular proliferation accelerates peripheral expansion of GBM up to 10-fold compared to lower grade astrocytoma, while over time the center of the tumor becomes anoxic and necrotic. Despite their appearance on MR imaging, GBM are not like spheroids with central hypoxia and necrosis. Hypoxia occurs over micron distances as do changes in oxygen gradients. Pimonidazole staining for hypoxic regions in the actively growing part of experimental and human GBM shows micro-constellations of hypoxic regions. Immunohistochemistry studies in human GBM have also shown that these regions strongly stain for HIF-1, a major regulator of the physiologic response to hypoxia. The appearance of hypoxia is a critical physiological change that heralds a more malignant tumor behavior which dramatically reduces patient survival. Vascularity and microvascular cell proliferation are morphological features used to distinguish grade IV gliomas from grade II/III and they correlate with patient prognosis. Angiogenesis is known to occur as the result of a disruption in the balanced synthesis of molecules that stimulate and inhibit new blood vessel formation. VEGF, the most important known regulator of tumor angiogenesis is transcriptionally upregulated by HIF-1. In situ hybridization has shown that VEGF mRNA is strongly expressed in pseudopalisading cells, a rim of viable hypoxic tumor cells that line micro-necrotic areas in GBM and which express high levels of HIF-1. In addition to promoting angiogenesis, hypoxic tumor cells are also refractive to radio- and chemo-therapies. Therefore, hypoxic areas of astrocytic tumors represent an important target for anti-tumor therapy and preliminary clinical studies targeting hypoxia have shown modification of outcome in GBM.

HIF is the primary transcription factor activated by hypoxia. Its activation and regulation are complex, with numerous points of potential inhibition. Active HIF is composed of alpha (HIF-1α, 2α) and beta (HIF-1β) subunits that dimerize and bind to consensus sequences (hypoxia responsive elements, HRE) in the regulatory regions of target genes. HIF controls the expression of more than 60 target genes whose products are critical to many aspects of tumor progression, including metabolic adaptation, apoptosis resistance, angiogenesis and metastasis. These include VEGF, erythropoietin, glucose transporters, and glycolytic enzymes. In normoxia, HIF is hydroxylated and interacts with the von Hippel Lindau protein (pVHL), an E3 ubiquitin ligase subunit that targets HIF for degradation. In the absence of oxygen, HIF hydroxylation is inhibited, preventing binding to pVHL and leading to its intracellular accumulation. HIF-1 has been recognized as an important molecular target for solid tumor therapy due to its crucial role in tumor angiogenesis and progression. Increased levels of intracellular HIF-1α are found in many cancers and are associated with poor prognosis and resistance therapy. HIF-2α upregulation is found predominantly in cancers with VHL gene mutations. HIF-1α expression correlates with tumor grade and vascularization in gliomas, while HIF-2α expression is usually absent. The relative importance of HIF-1α and HIF-2α subunits in different tissues and cancer types is still under investigation as are their multiple levels of regulation.

Accordingly, there is a need for new and effective treatments for cancer. In particular, there is a need for new and effective treatments that address hypoxia and its role in hyperproliferative pathologies.

SUMMARY

Generally, aspects of the present disclosure are directed to HIF inhibitors, and derivatives thereof, pharmaceutical compositions including a HIF inhibitor, and methods of using these compounds, for example, in the treatment of ischemic diseases, proliferative diseases such as cancer, hypoxia-related pathologies, diseases related to excessive vascularization, and the like.

Embodiments of the present disclosure include pharmaceutical compositions including one or more compounds selected from: formula A, formula B, formula C, and formula D, where each of formula A, formula B, formula C, and formula D can include an "X" group such as, but not limited to, X1, X2, X3, X4, X5, X6, X7, and X8. The compounds of formula A, formula B, formula C, and formula D and groups X1, X2, X3, X4, X5, X6, X7, and X8 are illustrated hereinafter.

Embodiments of the present disclosure include pharmaceutical compositions comprising, one or more compounds selected from: formula A', formula B', formula C', and formula D', where each of formula A', formula B', formula C', and formula D' can include an "X" group such as, but not limited to, X1', X2', X3', X4', X5', X6', X7', and X8'. The compounds of formula $A^1$, formula $B^1$, formula $C^1$, and formula $D^1$ and groups X1', X2', X3', X4', X5', X6', X7', and X8' are illustrated hereinafter.

It should also be noted that the $CH_2$—$SO_2$ group shown in X1-X8 (and in X1'-X8' in other figures) can be replaced by a linker group such as, but not limited to, an alkyl group, an amide group, a phosphonamide group, a carbamate group, a phosphodiester group, a phosphoramidate group, and a phosphinamide group. In addition, the benzene group (the far right of the formula) in formula A, D, $A^1$ and $D^1$ can be replaced with a monocyclic heterocyclic group (e.g., a pyrimidine group), a substituted heterocyclic group, a bicyclic heterocyclic group (e.g., a purine group), a substituted bicyclic heterocyclic group, a tricyclic heterocyclic group, a substituted tricyclic heterocyclic group, and the like.

Embodiments of the present disclosure include pharmaceutical compositions comprising, one or more compounds selected from: formula E, formula F, formula G, formula H, formula I, formula J, formula K, formula L, formula M, formula N, formula O, formula P, formula Q, formula R, formula S, formula T, formula U, formula V, formula W, and formula X. The compounds of formula E, formula F, formula G, formula H, formula I, formula J, formula K, formula L, formula M, formula N, formula O, formula P, formula Q, formula R, formula S, formula T, formula U, formula V, formula W, and formula X are illustrated hereinafter.

Embodiments of the present disclosure include pharmaceutical compositions comprising, one or more compounds selected from: formula E', formula F', formula G', formula H', formula I', formula J', formula K', formula L', formula M', formula N', formula O', formula P', formula Q', formula R', formula S', formula T', formula U', formula V', formula W', and formula X'. The compounds of formula E', formula F', formula G', formula H', formula I', formula J', formula K', formula L', formula M', formula N', formula O', formula P', formula Q', formula R', formula S', formula T', formula U', formula V', formula W', and formula X' are illustrated hereinafter.

Embodiments of the present disclosure include pharmaceutical compositions comprising, one or more compounds selected from: formula A'/X2', formula B'/X7', formula B'/X8', formula C'/X2', formula C'/X3', formula C'/X4', formula C'/X5', formula C'/X6', formula C'/X7', formula C'/X8', formula D'/X1', and formula D'/X7'. In particular, the HIF-1 inhibitors include, but are not limited to, formula B'/X7', formula B'/X8', formula C'/X7', formula C'/X8', and formula D'/X7'. The compounds of formula A'/X2', formula B'/X7', formula B'/X8', formula C'/X2', formula C'/X3', formula C'/X4', formula C'/X5', formula C'/X6', formula C'/X7', formula C'/X8', formula D'/X1', and formula D'/X7' are illustrated hereinafter.

Embodiments of the present disclosure include pharmaceutical compositions comprising, one or more compounds selected from: formula H', formula I', formula J', formula P', formula Q', formula R', formula S', formula T', formula U', formula V', formula W', and formula X'. The compounds of formula H', formula I', formula J', formula P', formula Q', formula R', formula S', formula T', formula U', formula V', formula W', and formula X' are illustrated hereinafter.

Embodiments of the present disclosure include pharmaceutical compositions comprising a hydrolysis, oxidation, or reduction reaction product of any of the compounds described herein.

Embodiments of the present disclosure include methods for the treatment or prevention of a hypoxia-related pathology comprising: administering to a host in need of such treatment a HIF inhibiting amount of any of the compositions described herein.

Embodiments of the present disclosure include methods of modulating HIF activity in a cell comprising: contacting the cell with a HIF inhibiting amount of any of the compositions described herein.

Embodiments of the present disclosure include methods of treating or preventing cancer or a tumor in a host comprising administering to the host a HIF inhibiting amount of any of the compositions described herein.

Embodiments of the present disclosure include methods of modulating gene transcription in a cell comprising contacting the cell with a HIF inhibiting amount of one or more of the compositions described herein.

Embodiments of the present disclosure include methods of modulating mRNA translation in a cell comprising contacting the cell with a HIF inhibiting amount of one or more of the compositions described herein.

Embodiments of the present disclosure include methods of treating or preventing excessive vascularization in a host comprising administering to the host a HIF inhibiting amount of any of the compositions described herein.

Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

FIG. 11 (C) shows that KCN1 inhibits hypoxia-induced HIF-1α but not normoxic induction with $CoCl_2$, DFX or MG132.

FIG. 17(A) illustrates a subcutaneous xenograft of LN-229 glioma cells. The hypoxic areas are in dark brown, at a distance of about 10 cell layers from the nearest vessel. FIG. 17(B) illustrates intra-cerebral xenograft of U87MG glioma cells. The dark brown rim of hypoxic cells surrounds vessels in pimonidazole-stained section on left. The right side shows H&E staining of an adjacent section. It should be noted that cells within a radius of about 10 cells proximal to vessel are alive (dark blue). Cells further distal are necrotic (light blue) and do not stain with pimonidazole.

FIG. 18(A) illustrates MRI of U87MG-EGFRvIII grown in mice brain. FIG. 18(B) illustrates the kinetics of KCN1 accumulation in normal and tumoral brain after iv. injection at 35 mg/kg.

FIG. 20(A) illustrates tumor volume over time as measured with a caliper. FIG. 20(B) shows a photograph of the dissected tumors at termination of experiment and illustrates that they weighed ~6-fold less in KCN1 group.

FIG. 22 illustrates HIF related genes, proteins, and pathways.

DETAILED DESCRIPTION

Figure 1A:
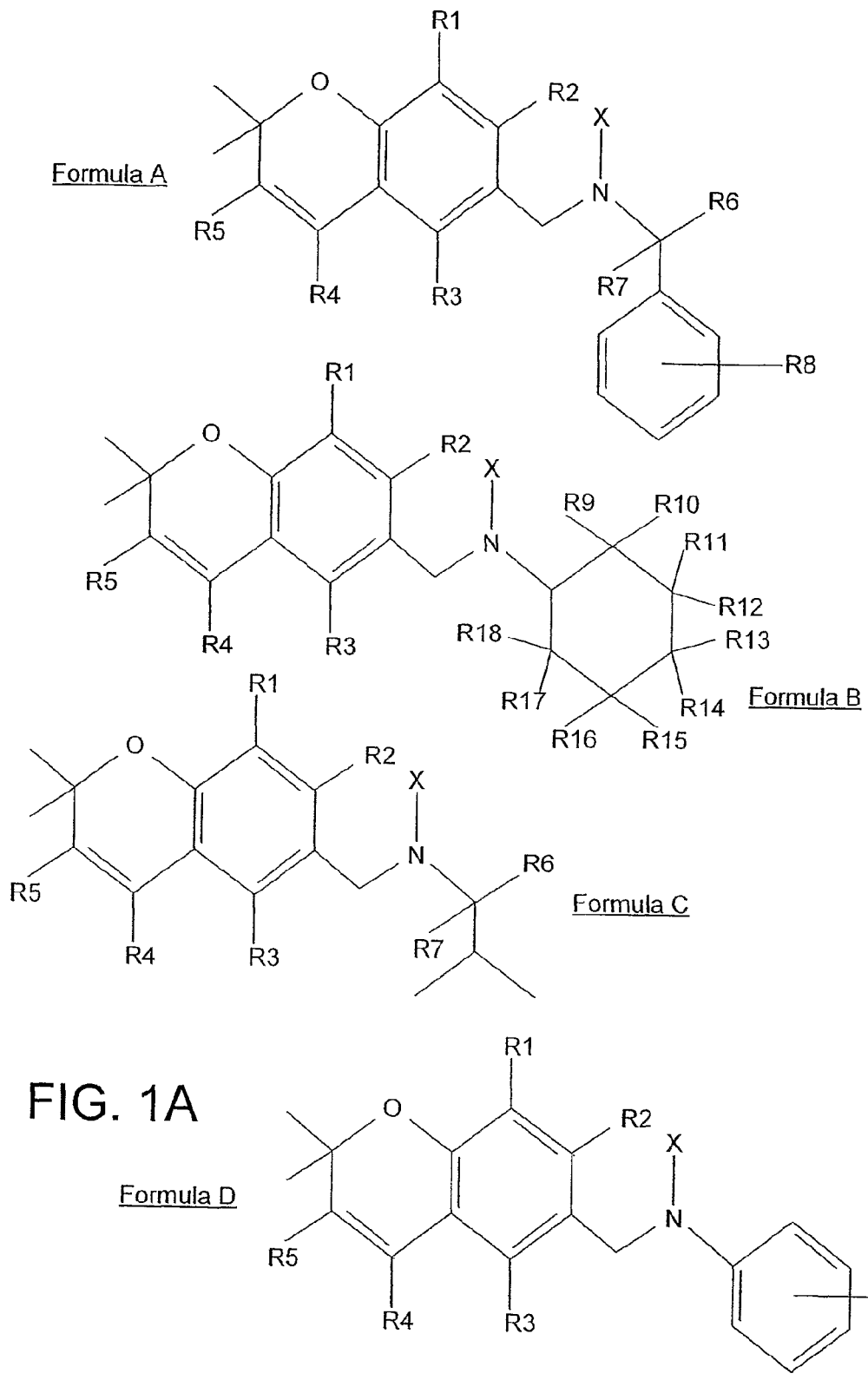
FIGS. 1A and 1B illustrate exemplar embodiments of formula for HIF inhibitors.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere. Experimental hypoxia was obtained by growing cells in culture medium in an incubator under an environment of 1% partial pressure of oxygen unless otherwise indicated.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DEFINITIONS

The term "organism" or "host" refers to any living entity comprised of at least one cell. A living organism can be as simple as, for example, a single eukaryotic cell or as complex as a mammal, including a human being.

The term "HIF inhibitor" means a compound, pharmaceutically acceptable salt, prodrug, or derivative thereof that inhibits the biological activity of HIF-1, HIF-2, and HIF-3, interferes with the HIF-1, HIF-2, and HIF-3, signal transduction pathway, or down regulates expression or availability of HIF-1, HIF-2, and HIF-3 in a cell or organism.

The term "hypoxia-related pathology" means a pathology that is caused in part, either directly or indirectly, by conditions of below typical physiological amounts of oxygen. The term "hypoxia-related pathology" also means a pathology caused by a non-hypoxic stimuli. The term includes cancer, cancer metastasis, ischemia, stroke and related conditions, diseases, or syndromes.

The term "derivative" means a modification to the disclosed compounds including but not limited to hydrolysis, reduction, or oxidation products of the disclosed compounds. In particular, the term encompasses opening of a nitrogen containing ring structure, including but not limited to an imidazole, of the disclosed compounds. Hydrolysis, reduction, and oxidation reactions are known in the art.

The term "therapeutically effective amount" as used herein refers to that amount of the compound being administered which will relieve to some extent one or more of the symptoms of the disorder being treated. In reference to cancer or pathologies related to unregulated cell division and/or lack of programmed cell death, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the local invasion and distant metastasis of cancer cells, (4) relieving to some extent (or, preferably, eliminating) one or more symptoms associated with a pathology related to or caused in part by unregulated or aberrant cellular division, including for example, cancer, (5) prevention of the formation of cancer by application of the compound (like sun screen to protect against cancer), and/or (6) to prevent the chain of events downstream of an initial ischemic condition which leads to the pathology.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer, these terms simply mean that the life expectancy of an individual affected with a cancer will be increased or that one or more of the symptoms of the disease will be reduced.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. *Progress in Drug Research*, 4:221-294; Morozowich et al. (1977). Application of Physical Organic Principles to Prodrug Design in E. B. Roche ed. *Design of Biopharmaceutical Properties through Prodrugs and Analogs*, APhA; Acad. Pharm. Sci.; E. B. Roche, ed. (1977). *Bioreversible Carriers in Drug in Drug Design, Theory and Application*, APhA; H. Bundgaard, ed. (1985) *Design of Prodrugs*, Elsevier; Wang et al. (1999) Prodrug approaches to the improved delivery of peptide drug, *Curr. Pharm. Design*. 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, Eds., *Transport Processes in Pharmaceutical Systems*, Marcell Dekker, p. 185-218; Balant et al. (1990) Prodrugs for the improvement of drug absorption via different routes of administration, *Eur. J. Drug Metab. Pharmacokinet.*, 15(2): 143-53; Balimane and Sinko (1999). Involvement of multiple transporters in the oral absorption of nucleoside analogues, *Adv. Drug Delivery Rev.*, 39(1-3):183-209; Browne (1997). Fosphenyloin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) *Design of Prodrugs*, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharm. Sci.*, 72(3): 324-325; Han, H. K. et al. (2000). Targeted prodrug design to optimize drug delivery, *AAPS PharmSci.*, 2(1): E6; Sadzuka Y. (2000). Effective prodrug liposome and conversion to active metabolite, *Curr. Drug Metab.*, 1(1):31-48; D. M. Lambert (2000) Rationale and applications of lipids as prodrug carriers, *Eur. J. Pharm. Sci.*, 11 Suppl 2:S15-27; Wang, W. et al. (1999) Prodrug approaches to the improved delivery of peptide drugs. *Curr. Pharm. Des.*, 5(4):265-87.

As used herein, the term "topically active agents" refers to compositions of the present disclosure that elicit pharmacological responses at the site of application (contact in a topical application) to a host.

As used herein, the term "topically" refers to application of the compositions of the present disclosure to the surface of the skin and mucosal cells and tissues.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, and the like. Lower alkyl groups, that is, alkyl groups of 1 to 6 carbon atoms, are generally most preferred. The term "substituted alkyl" refers to alkyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The term "alkoxy" means an alkyl group linked to oxygen thus: R—O—. In this function, R represents the alkyl group. An example would be the methoxy group $CH_3O$—.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The terms "halogen" and "halo" refer to fluorine, chlorine, bromine, and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 member monocyclic, 7 to 17 member bicyclic, or 10 to 20 member tricyclic ring systems, preferably containing a total of 3 to 10 ring atoms) that have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4-dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3 to 7 member ring.

The term "alkanoyl" refers to alkyl group (which may be optionally substituted as described above) linked to a carbonyl group (e.g., —C(O)-alkyl). Similarly, the term "aroyl" refers to an aryl group (which may be optionally substituted as described above) linked to a carbonyl group (e.g., —C(O)-aryl).

Throughout the specification, groups and substituents thereof may be chosen to provide stable moieties and compounds.

The disclosed compounds form salts which are also within the scope of this invention. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The disclosed compounds that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The disclosed compounds that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

To the extent that the disclosed compounds, and salts thereof, may exist in their tautomeric form, all such tautomeric forms are contemplated herein as part of the present disclosure.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974 Recommendations.

The terms "including", "such as", "for example" and the like are intended to refer to exemplary embodiments and not to limit the scope of the present disclosure.

Discussion

HIF inhibitor compounds and compositions including HIF inhibitors, pharmaceutical compositions, methods for the treatment or prevention of a hypoxia-related pathology, a HIF-related pathology, methods of modulating HIF activity (e.g., HIF-1, HIF-2, or HIF-3) activity in a cell, methods of treating or preventing cancer or a tumor in a host, methods of modulating gene transcription in a cell, and methods of treating pathologies characterized by excessive vascularization (for example of the eye), are disclosed. Exemplary HIF inhibitor compounds or compositions including HIF inhibitor compounds are shown in FIGS. 1A through 6. Additional details regarding HIF inhibitors are described below and in Examples 1 and 2.

The inhibition of HIF-1, HIF-2, and/or HIF-3-mediated gene regulation will reduce tumor angiogenesis and prevent the adaptative metabolic response to hypoxia, thus suppressing tumor growth. Although not intending to be bound by theory, HIF inhibitors of the present disclosure that lead to downstream prevention of HIF-1/HRE interaction are expected to lead to the attenuation of hypoxia- or HIF-include gene expression, retardation of tumor growth, and minimal toxicity towards normal tissues. Therefore, inhibitors of the HIF-1, HIF-2, and/or HIF-3 pathways should be able to interfere with solid tumor growth and have clinical therapeutic potential.

In addition, it should be noted that the compounds are described as "HIF inhibitors", but in some instances (some of which are mentioned below) the compounds have a direct or indirect effect on other proteins or pathways and such effects are beneficial. Thus, the HIF inhibitors are not limited to having an effect on only the HIF pathway.

Hypoxia Inducible Factors (HIF-1, HIF-2, and HIF-3)

HIF is a primary transcription factor responsible for specific induction of genes in hypoxia. HIF is composed of two subunits belonging to the bHLH-PAS family: HIF-1 alpha or HIF-2alpha and aryl hydrocarbon receptor nuclear translocator (ARNT also known as HIF-1 beta). To activate transactivation of target genes, HIF alpha subunits a dimerize with HIF-1 beta and bind to consensus sequences on DNA (hypoxia responsive element, HRE) in the promoter or enhancer regions of these genes. In contrast, HIF dimers containing HIF3alpha subunits are not transcriptionally active and HIF3alpha isoforms may act as dominant negative regulators. Proteins encoded by such genes include vascular endothelial growth factor (VEGF), erythropoietin, glucose transporter-1, glycolytic enzymes and tyrosine hydroxylase (Semenza G. L. Regulation of mammalian homeostasis by hypoxia-inducible factor 1. Annu Rev Cell Dev Biol 15, 551-78 (1999)). Additional HIF related genes are described in FIG. 22 and in the following publications, all of which are incorporated herein by reference: Cancer Treat Rev. 2006 Aug. 2; Cardiovasc Hematol Agents Med. Chem. 2006 July; 4(3):199-218; Cardiovasc Hematol Agents Med. Chem. 2006 July; 4(3):189-97; Curr Pharm Des. 2006; 12(21):2673-88; Ann NY Acad Sci. 2006 April; 1068:66-73; Circ Res. 2006 Jun. 23; 98(12): 1465-7; Cardiovasc Res. 2006 Sep. 1; 71(4):642-51; Sci STKE. 2006 May 30; 2006(337):pe25; Endocr Relat Cancer. 2006 June; 13(2):415-25; Nature. 2006 May 25; 441 (7092): 437-43; Shock. 2006 June; 25(6):557-70; Crit. Rev Oncol Hematol. 2006 July; 59(1):15-26; Novartis Found Symp. 2006; 272:2-8; discussion 8-14, 33-6; Curr Atheroscler Rep. 2006 May; 8(3):252-60; Am J Physiol Renal Physiol. 2006 August; 291(2):F271-81; Curr Opin Neurol. 2006 April; 19(2):141-7; Kidney Blood Press Res. 2005; 28(5-6):325-40; Kidney Int. 2006 April; 69(8):1302-7; Trends Mol. Med. 2006 April; 12(4):141-3; Int J Radiat Oncol Biol Phys. 2006

Feb. 1; 64(2):343-54; Int J Radiat Oncol Biol Phys. 2006 Feb. 1; 64(2):343-54; Z Gastroenterol. 2006 January; 44(1):67-76; EMBO Rep. 2006 January; 7(1):41-5; Curr Cancer Drug Targets. 2005 December; 5(8):595-610; and Chest. 2005 December; 128(6 Suppl):592S-594S.

In normoxia, von Hippel Lindau protein (pVHL) organizes the assembly of a complex that activates the E3 ubiquitin ligase which then ubiquitinylates HIF-1α, targeting its degradation. The interaction between HIF-1α and pVHL is regulated through hydroxylation of two proline residues of HIF-1α by a prolyl hydroxylase. In the absence of oxygen, this enzyme is no longer active and HIF-1α does not interact with pVHL and accumulates intracellularly (Ivan, M. et al. HIFα targeted for VHL-mediated destruction by proline hydroxylation: implications for $O_2$ sensing. Science 292, 464-8 (2001); Jaakkola, P. et al. Targeting of HIFα to the von Hipplel Lindau ubiquitylation complex by $O_2$ regulated prolyl hydroxylation. Science 292, 468-72 (2001)).

Tumor hypoxia increases malignant progression and metastasis by promoting angiogenesis through the induction of proangiogenic proteins such as VEGF (Schweiki, D. et al. Vascular endothelial growth factor induced by hypoxia may mediate hypoxia-induced angiogenesis. Nature 359, 843-5 (1992)). Most genes induced by hypoxia are regulated by HIF-1α, this protein therefore plays a pivotal role in tumor development (Dachs G. U. and Chaplin, D. J. Microenvironmental control of gene expression: implications for tumor angiogenesis, progression, and metastasis. Semin Radiat Oncol 8, 208-16 (1998); Maxwell, P. H. et al. Hypoxia-inducible factor-1 mediates gene expression in solid tumors and influences both angiogenesis and tumor growth. Proc Natl Acad Sci USA 94, 8104-9 (1997); Semenza, G. L. Hypoxia-inducible factor 1: master regulator of $O_2$ homeostasis. Curr Opin Genet Dev 8, 588-94 (1998)). Histological analyses have shown that an increased level of intracellular HIF-1α was associated with poor prognosis and resistance to therapy in head and neck, breast, cervical, and oropharyngeal cancers (Beasley, N.J. P. et al. Hypoxia-inducible factors HIF-1α and HIF-2α in head and neck cancer: relationship to tumor biology and treatment outcome in surgically resected patients. Cancer Res 62, 2493-7 (2002); Schindl, M. et al. Overexpresssion of hypoxia-inducible factor Iα is associated with an unfavorable prognosis in lymph node-positive breast cancer. Clin Cancer Res 8, 1831-7 (2002); Birner, P. et al. Overexpression of hypoxia-inducible factor Ia is a marker for an unfavorable prognosis in early-stage invasive cervical cancer. Cancer Res 60, 4693-6 (2000); Aebersold, D. M. et al. Expression of hypoxia-inducible factor-Iα: a novel predictive and prognostic parameter in the radiotherapy of oropharyngeal cancer. Cancer Res 61, 2911-6 (2001)). HIF-1α was overexpressed in the cytoplasm and the nucleus of colon, breast, gastric, lung, skin, ovarian, pancreatic, prostate, and renal carcinomas.

HIF Inhibitors

Embodiments of the present disclosure include the HIF inhibitors shown in FIGS. 1-8, derivatives thereof, pharmaceutically acceptable salts derivatives thereof, prodrugs derivatives thereof and pharmaceutical compositions including at least one HIF inhibitor.

Figure 1B:
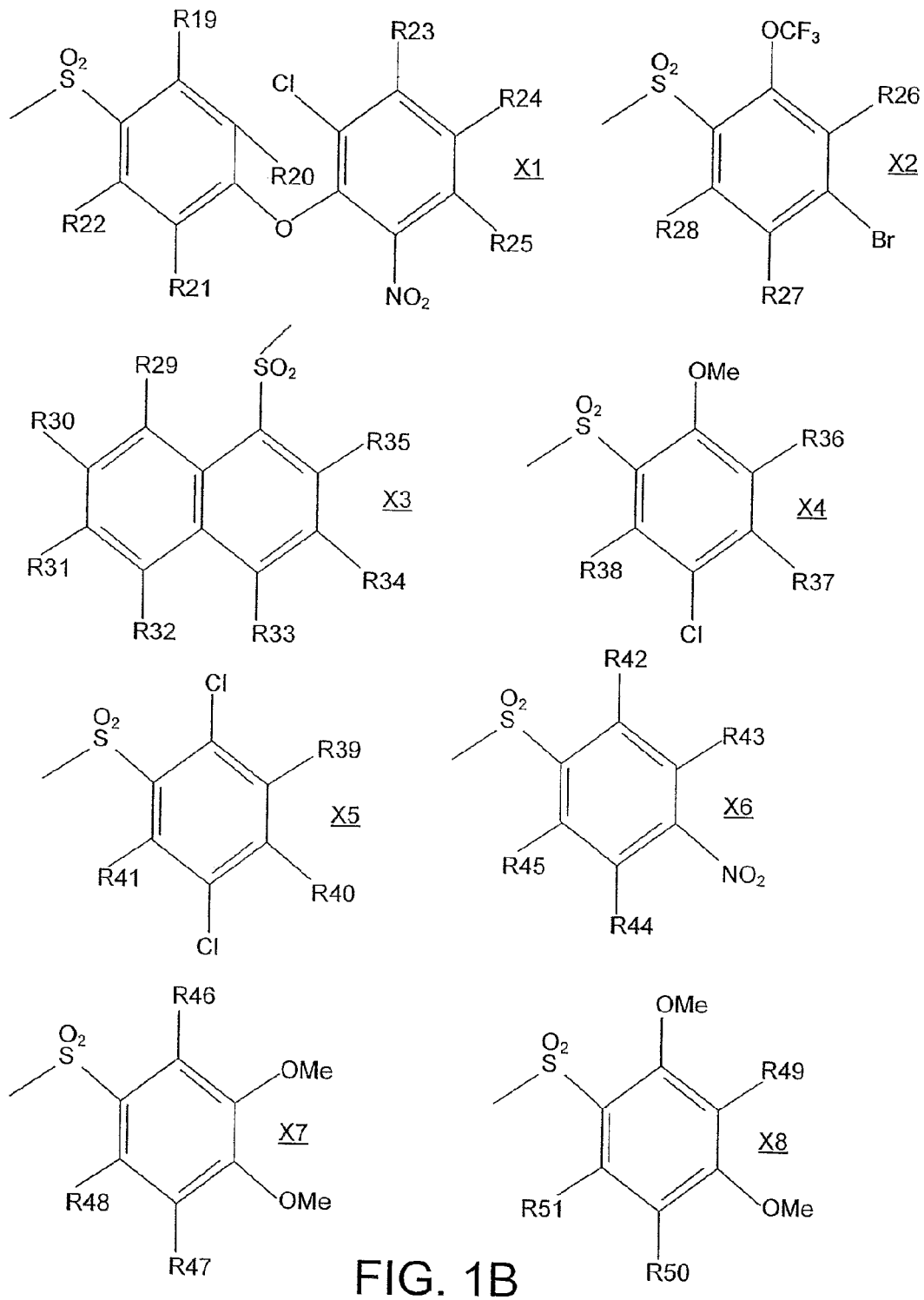

FIGS. 1A and 1B illustrate exemplar embodiments of formulae for HIF inhibitors. The HIF inhibitors include, but are not limited to, formula A, formula B, formula C, and formula D. Formula A, formula B, formula C, and formula D each can include an "X" group such as, but not limited to, X1, X2, X3, X4, X5, X6, X7, and X8 (e.g., formula A/X1, formula B/X8, and so on).

It should also be noted that the $CH_2$—$SO_2$ group shown in X1-X8 (and in X1'-X8' in other figures) can be replaced by a linker group such as, but not limited to, an alkyl group, an amide group, a phosphonamide group, a carbamate group, a phosphodiester group, a phosphoramidate group, and a phosphinamide group. In addition, the benzene group (the far right of the formula) in formula A and D can be replaced with a monocyclic a heterocyclic group (e.g., a pyrimidine group), a substituted heterocyclic group, a bicyclic heterocyclic group (e.g., a purin group), a substituted bicyclic heterocyclic group, a tricyclic heterocyclic group, a substituted tricyclic heterocyclic group, and the like.

R1, R2, R3, R4, R5, R6, R7, R8, R9, R10, R11, R12, R13, R14, R15, R16, R17, and R18, can each independently be selected from groups that enhance one or more of the following HIF inhibitor properties of the HIF inhibitor: enhance the solubility of the HIF inhibitor, the ADME properties, enhance the pharmacology, enhance the pharmacodynamics of the HIF inhibitor, enhance the pharmacokinetics of the HIF inhibitor, diminish toxicity, augment bioavailability, and combinations thereof.

In embodiments, R1, R2, R3, R4, R5, R6, R7, R8, R9, R10, R11, R12, R13, R14, R15, R16, R7, and R18, can each independently be selected from groups such as, but not limited to, H, OH, a branched or unbranched $C_{1-12}$ alkyl group, an alkenyl group, an alkoxy group, an aryl group, a heterocycle group, an imidazole group, a substituted imidazole group, an alkyl substituted aryl group, a halogen substituted aryl group, a halogen group, an amine group, $NO_2$, and an acyl group.

In other embodiments, R1, R2, R3, R4, R5, R6, R7, R8, R9, R10, R11, R12, R13, R14, R15, R16, R17, and R18, can each independently be selected from groups such as, but not limited to, H, OH, a branched or unbranched $C_{1-12}$ alkyl group, an alkoxy group, an aryl group, a heterocycle group, an imidazole group, an alkyl substituted aryl group, a halogen substituted aryl group, a halogen group, an amine group, and an acyl group.

In other embodiments, R1, R2, R3, R4, R5, R6, R7, R8, R9, R10, R1, R12, R13, R14, R15, R16, R17, and R18, can each independently be selected from groups such as, but not limited to, H, OH, a halogen, an alkyl group, an alkoxy group, and an alkenyl group.

In other embodiments, R1, R2, R3, R4, R5, R6, R7, R8, R9, R10, R11, R12, R13, R14, R15, R16, R17, and R18, can each independently be selected from groups such as, but not limited to, H, OH, a halogen, an alkyl group, and an alkoxy group.

In embodiments, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, and R51, can each independently be selected from groups that enhance the solubility of the HIF inhibitor, the ADME properties, enhance the pharmacology, enhance the pharmacodynamics of the HIF inhibitor, enhance the pharmacokinetics of the HIF inhibitor, diminish toxicity, augment bioavailability, and combinations thereof.

In other embodiments, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, and R51, can each independently be selected from groups such as, but not limited to, H, OH, a branched or unbranched $C_{1-12}$ alkyl group, an alkenyl group, an alkoxy group, an aryl group, a heterocycle group, an imidazole group, a substituted imidazole group, an alkyl substituted aryl group, a halogen substituted aryl group, a halogen group, an amine group, $NO_2$, and an acyl group.

In other embodiments, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, and R51, can each independently be selected from groups such as, but not limited to, H, OH, a branched or unbranched $C_{1-12}$ alkyl group, an alkoxy group, an aryl group, a heterocycle group, an imidazole group, an alkyl substituted aryl group, a halogen substituted an aryl group, a halogen group, an amine group, and an acyl group.

In other embodiments, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, and R52, can each independently be selected from groups such as, but not limited to, H, OH, a halogen, an alkyl group, an alkoxy group, and an alkenyl group.

In other embodiments, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, and R51, can each independently be selected from groups such as, but not limited to, H, OH, a halogen, an alkyl group, and an alkoxy group.

Figure 2A:
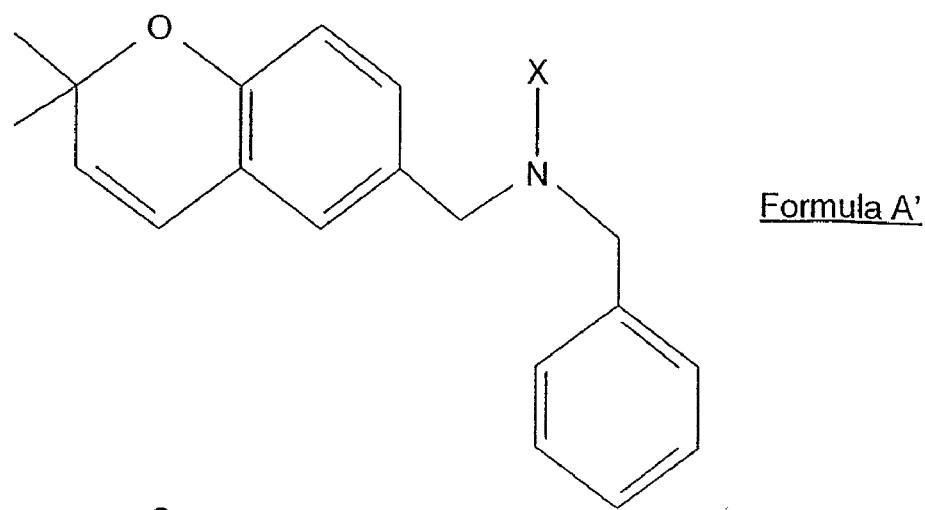
FIGS. 2A and 2B illustrate exemplar embodiments of formula for HIF inhibitors.
Figure 2A:
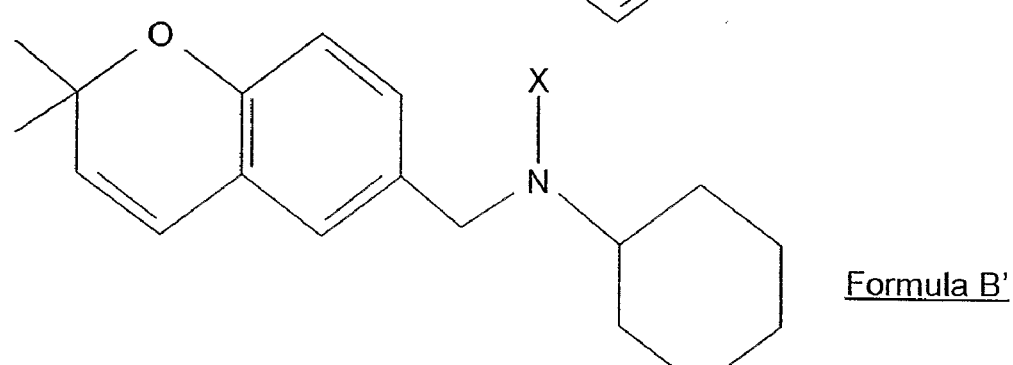
Figure 2A:
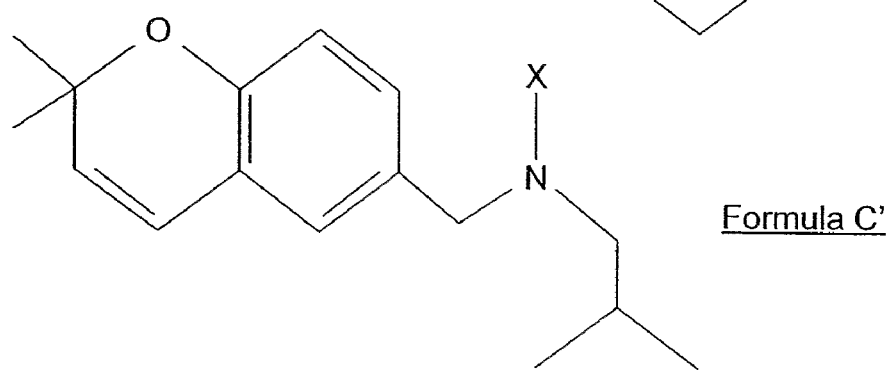
Figure 2A:
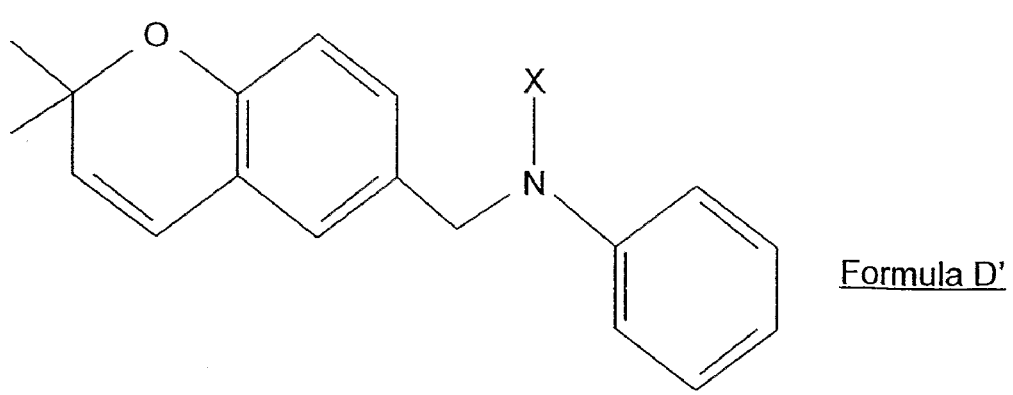
Figure 2B:
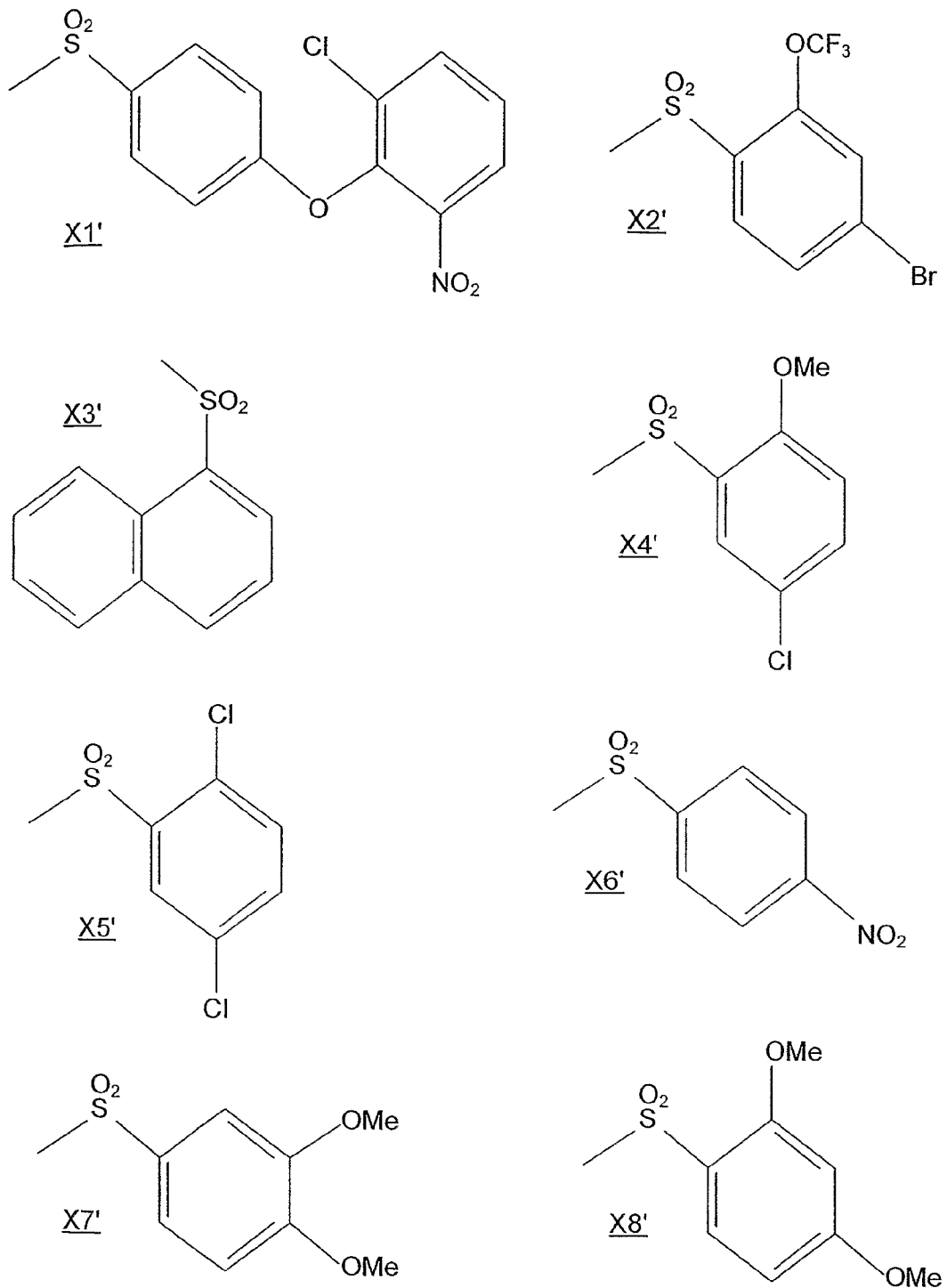
Figure 3A:
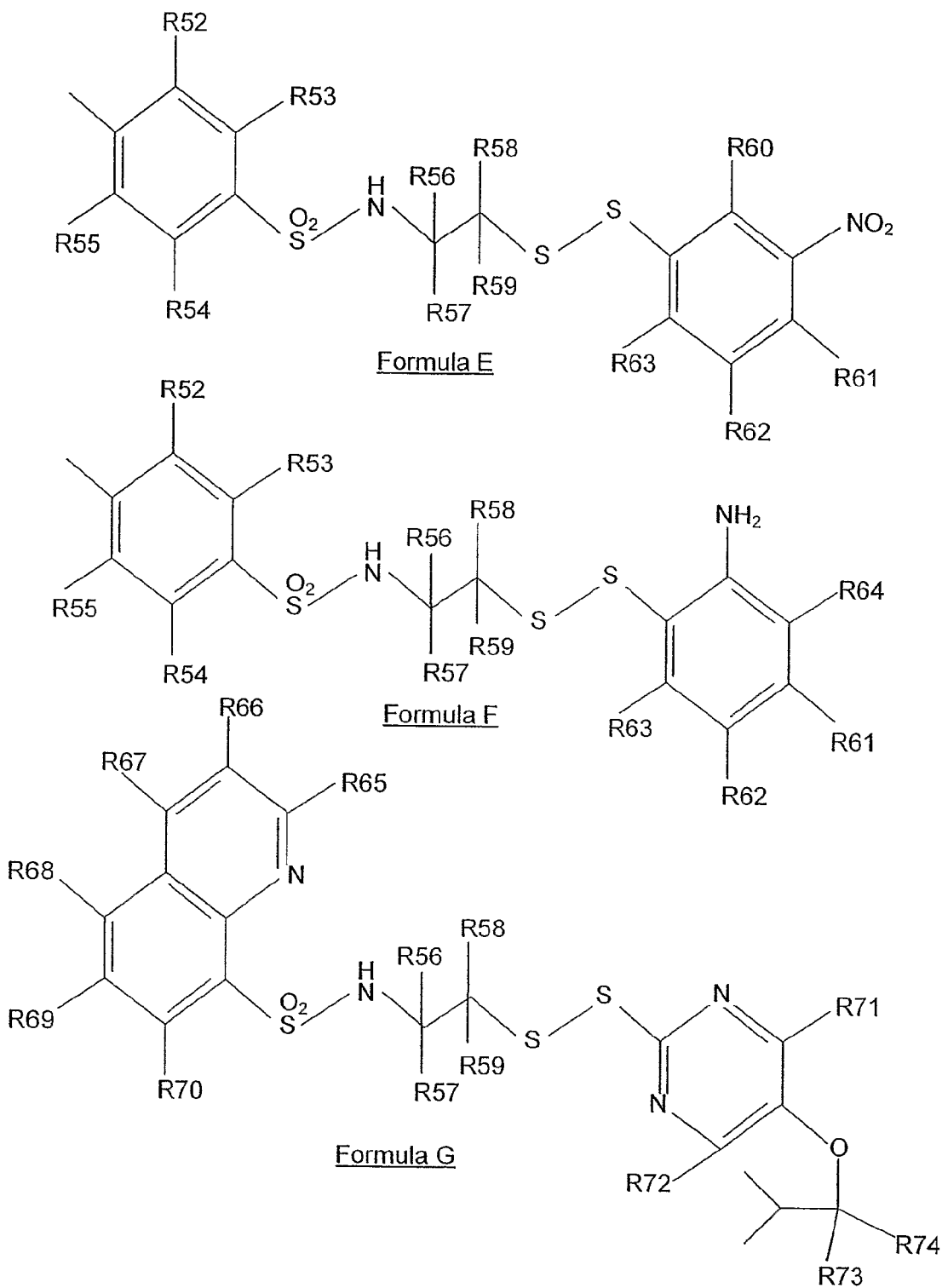
FIGS. 3A through 3G illustrate exemplar embodiments of formula for HIF inhibitors.
Figure 3B:
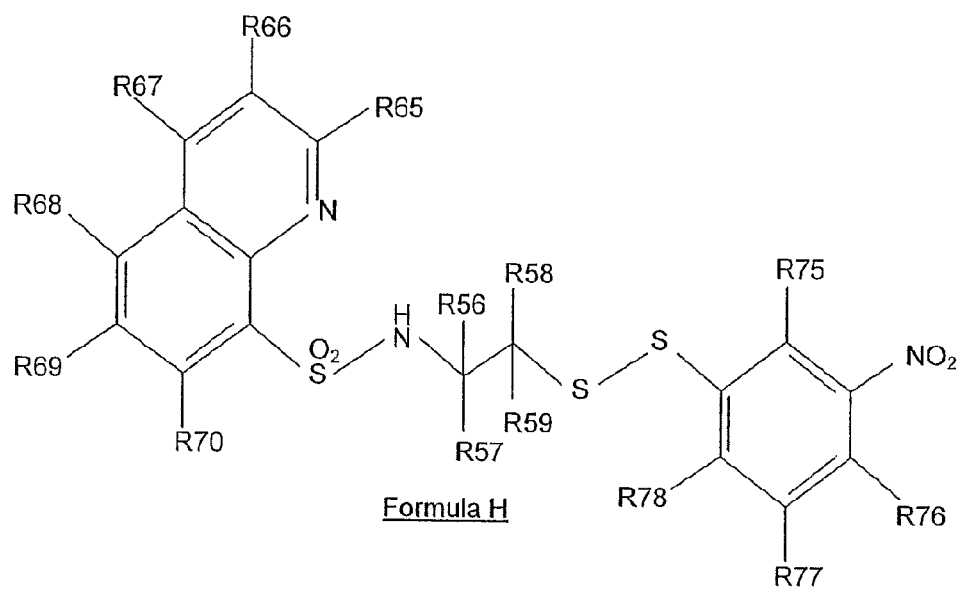
Figure 3B:
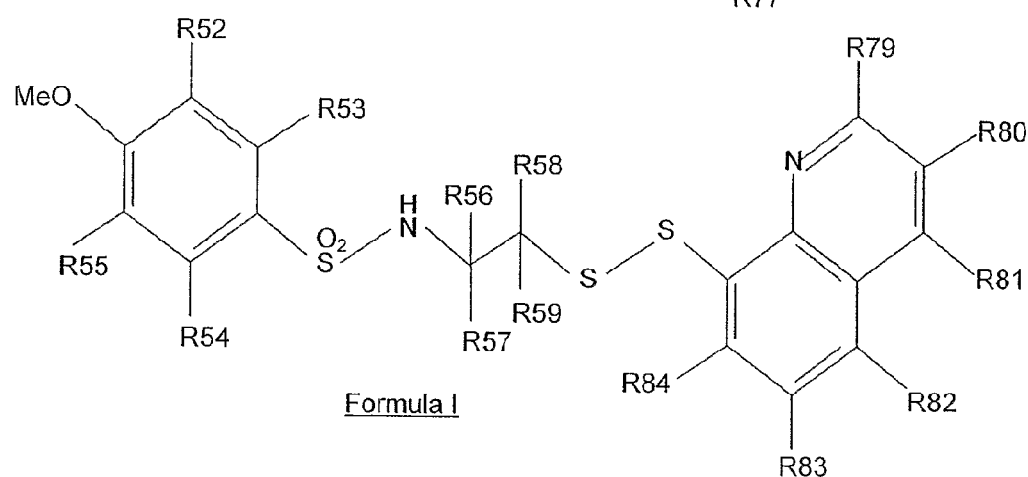
Figure 3B:
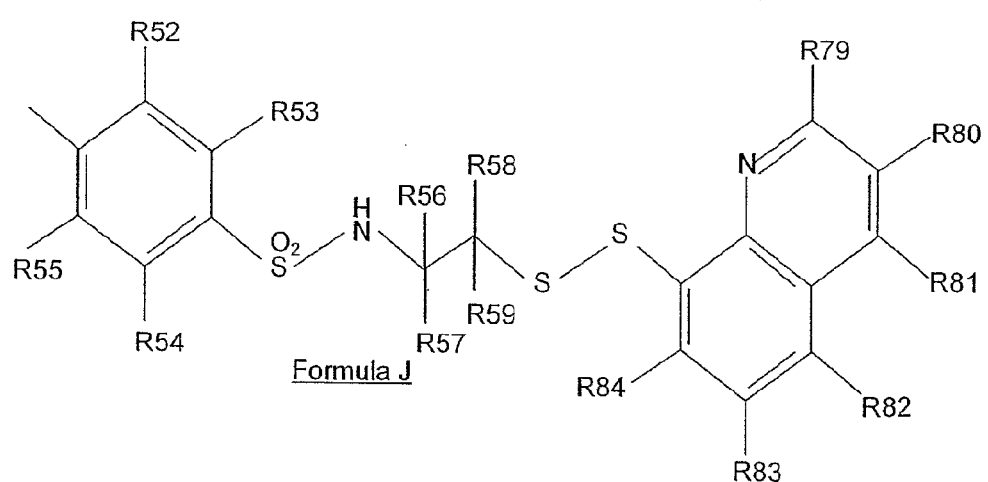
Figure 3C:
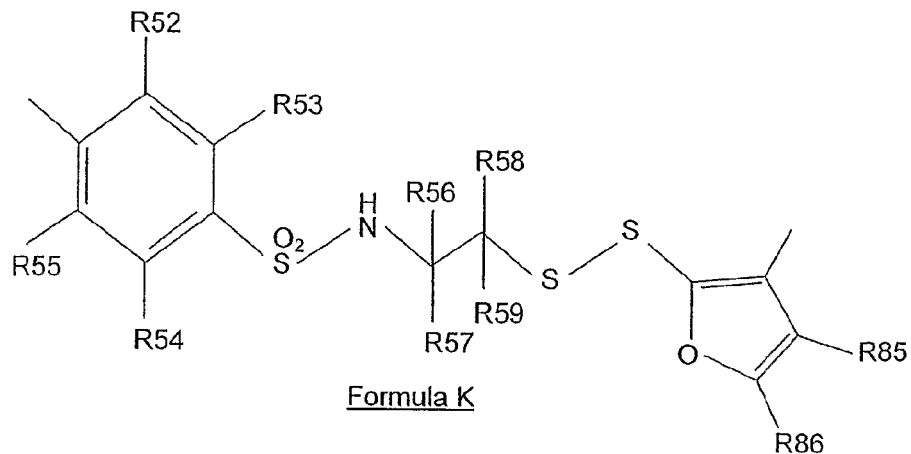
Figure 3C:
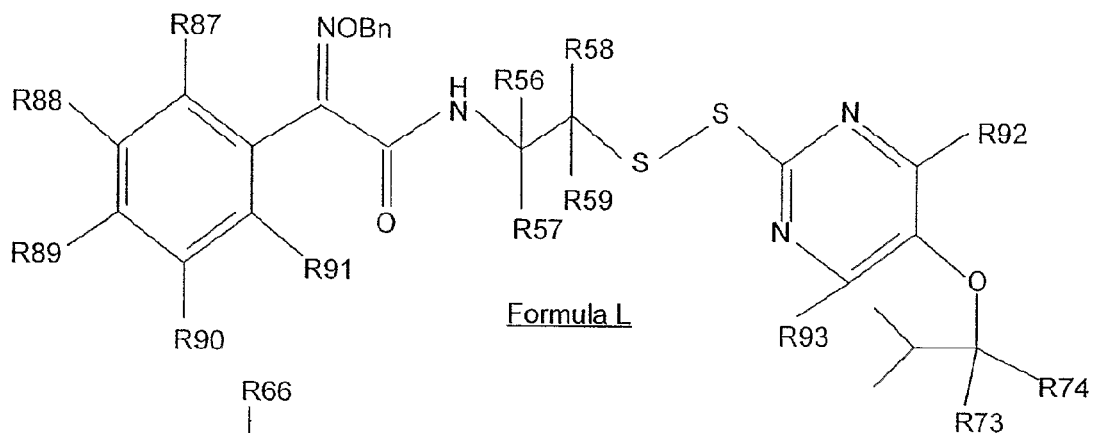
Figure 3C:
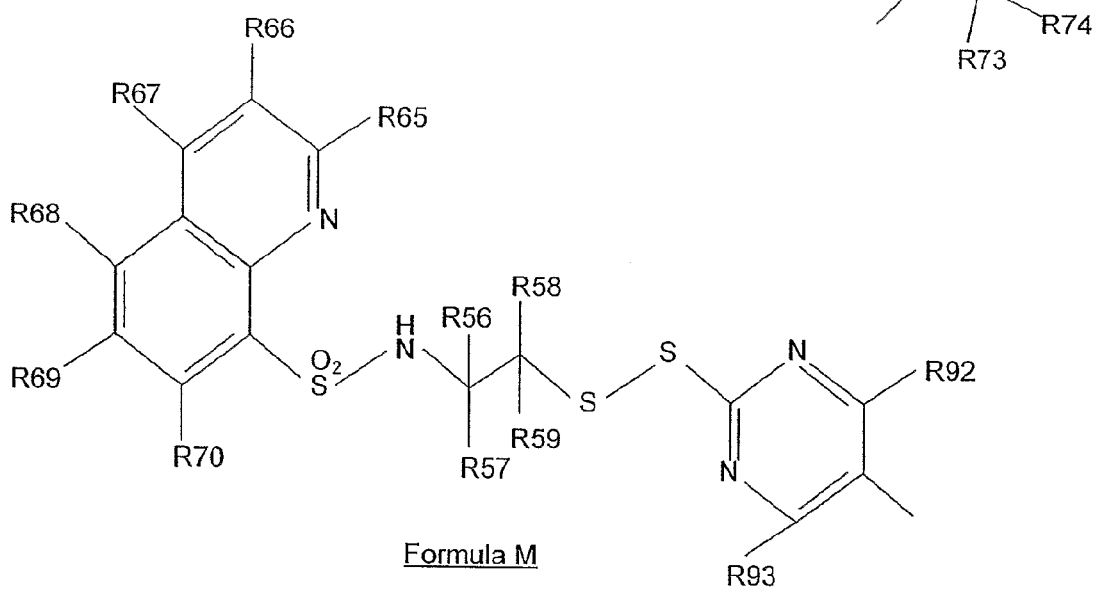
Figure 3D:
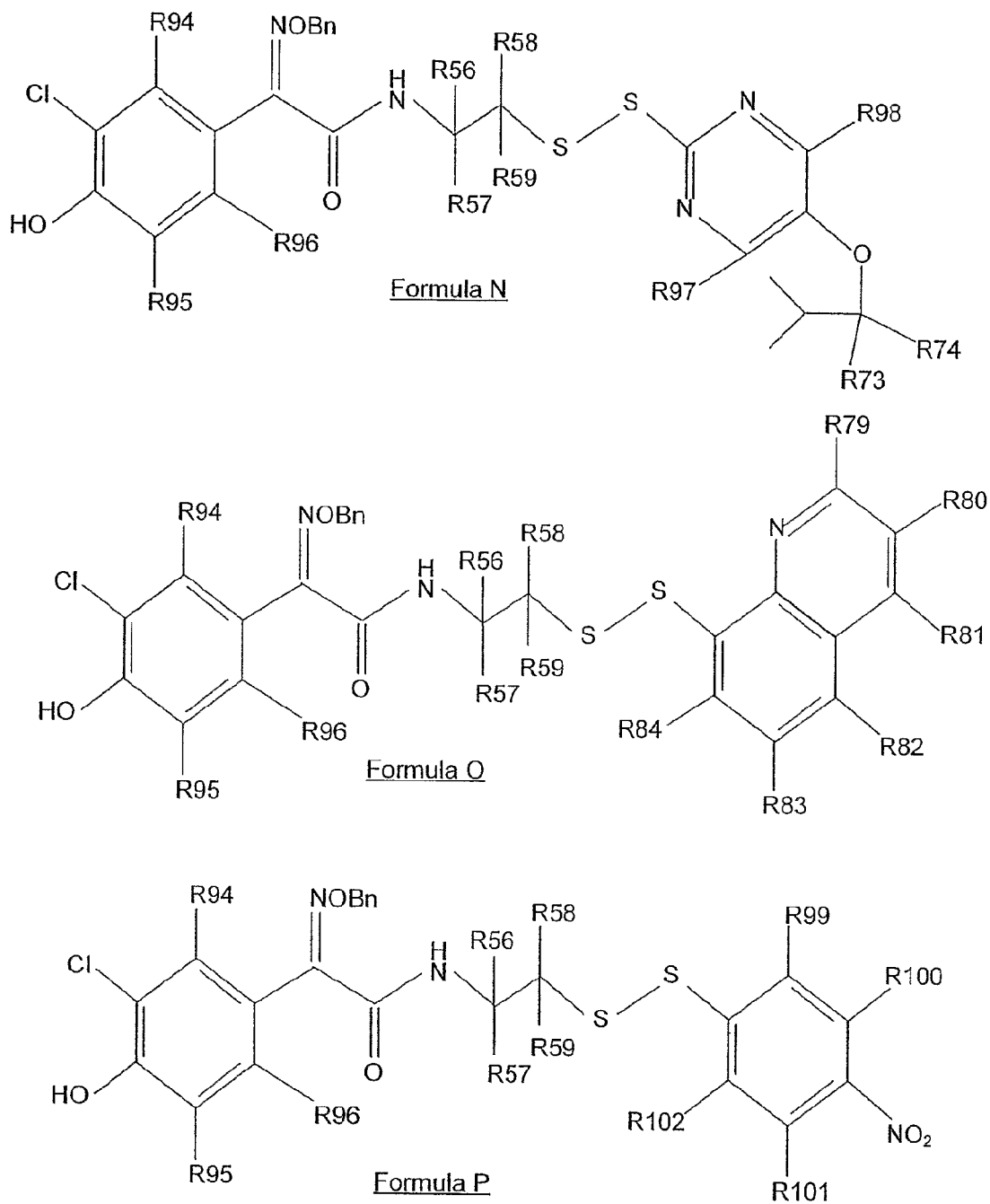
Figure 3E:
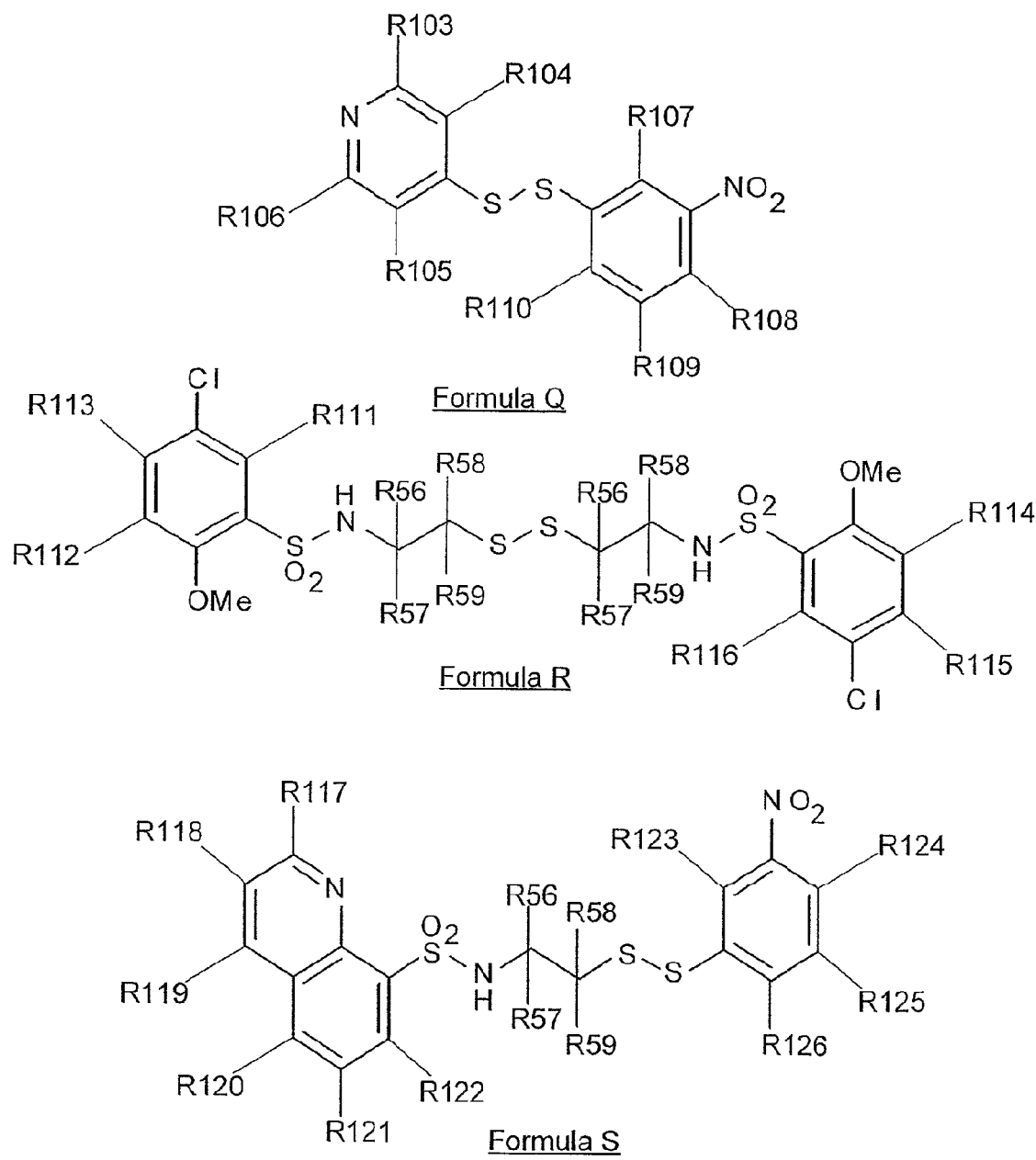
Figure 3F:
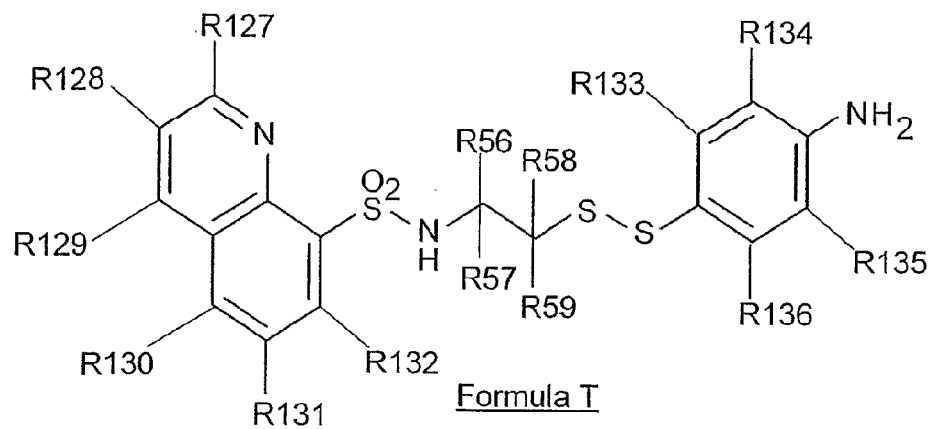
Figure 3F:
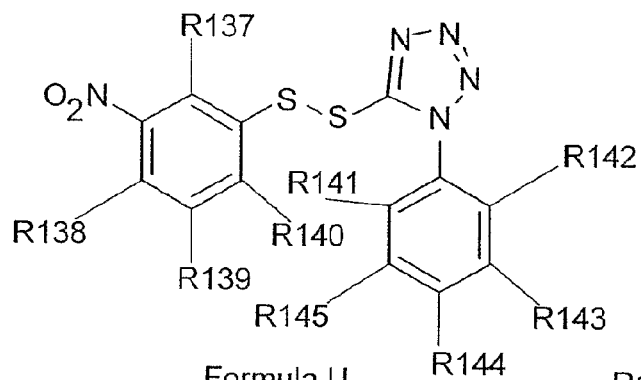
Figure 3F:
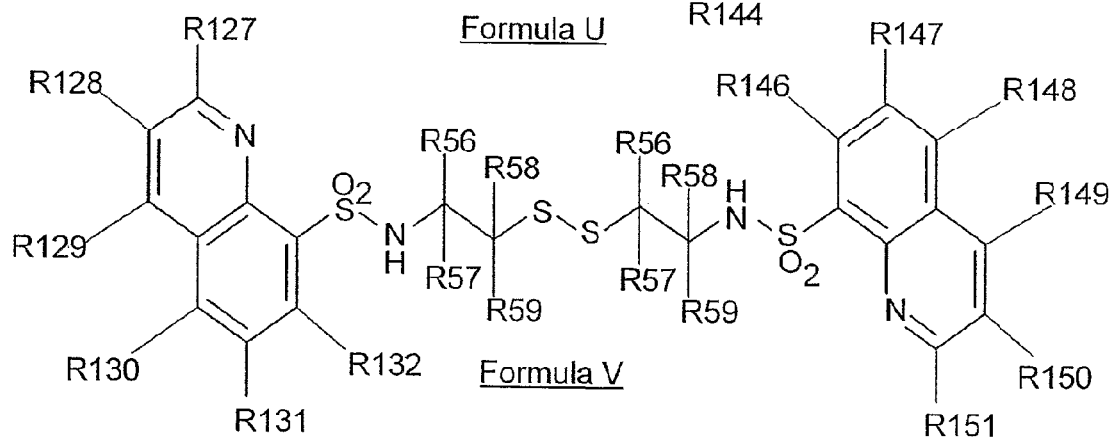
Figure 3G:
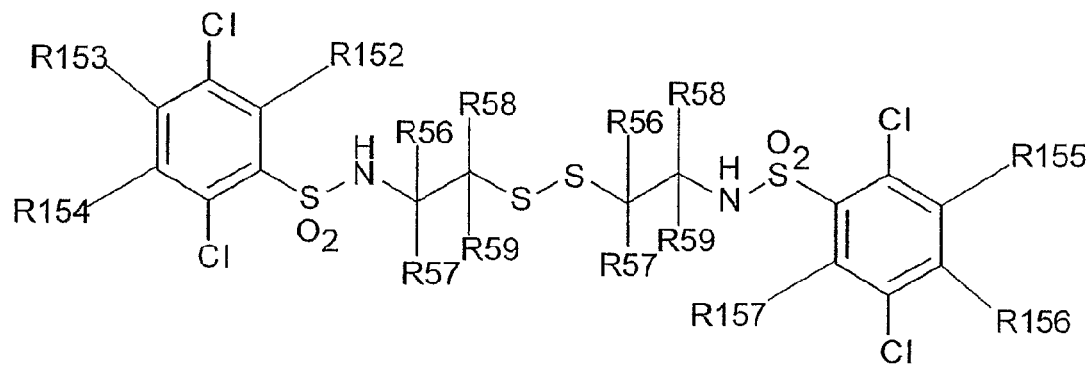
Figure 3G:
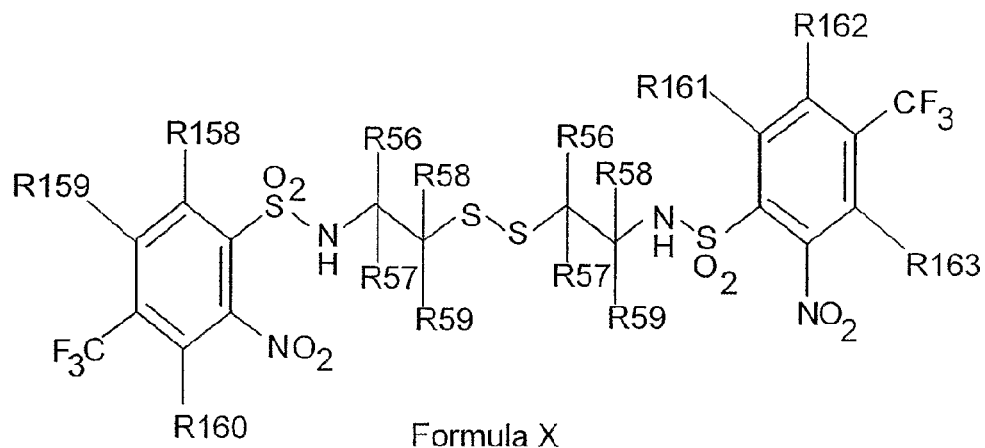
Figure 4A:
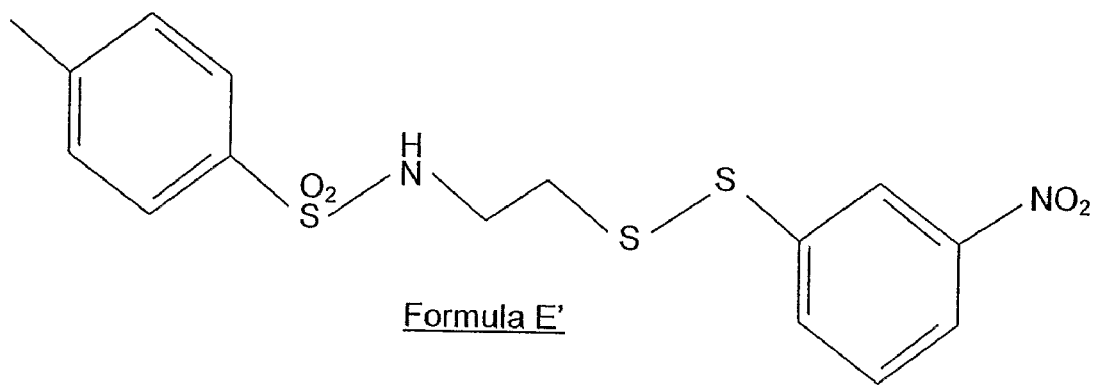
FIGS. 4A through 4G illustrate exemplar embodiments of formula for HIF inhibitors.
Figure 4A:
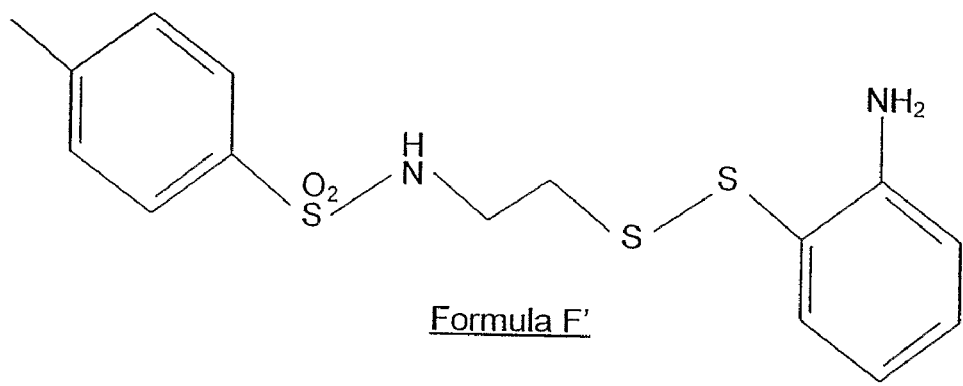
Figure 4A:
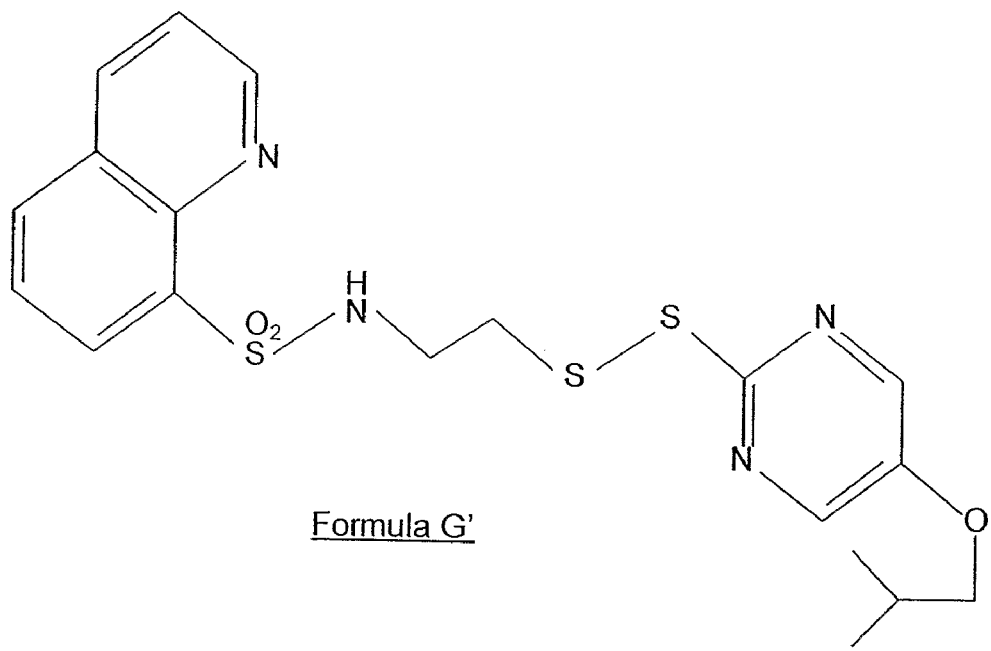
Figure 4B:
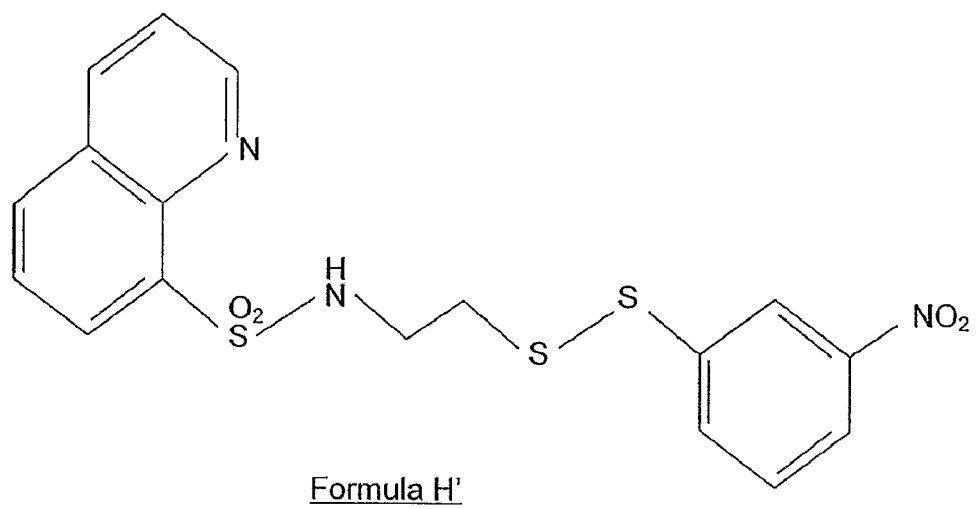
Figure 4B:
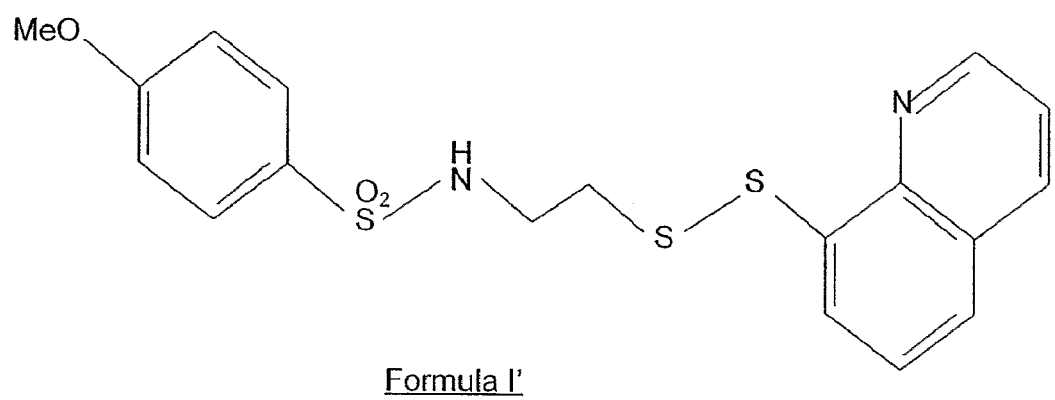
Figure 4B:
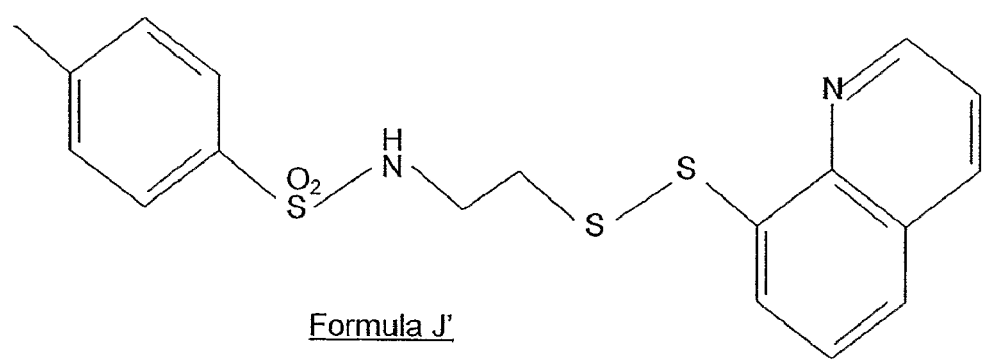
Figure 4C:
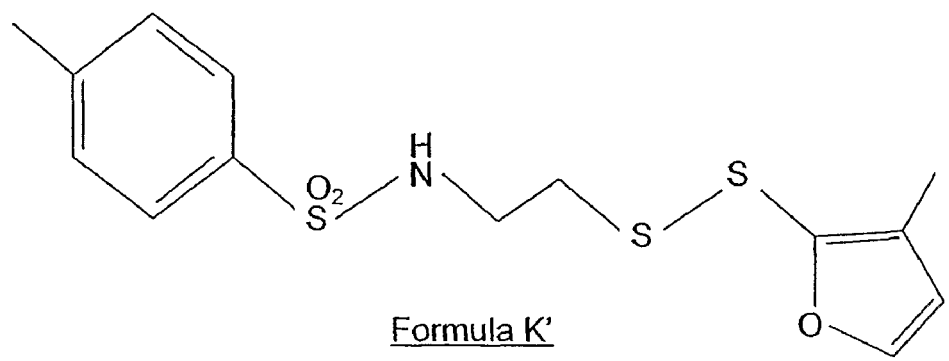
Figure 4C:
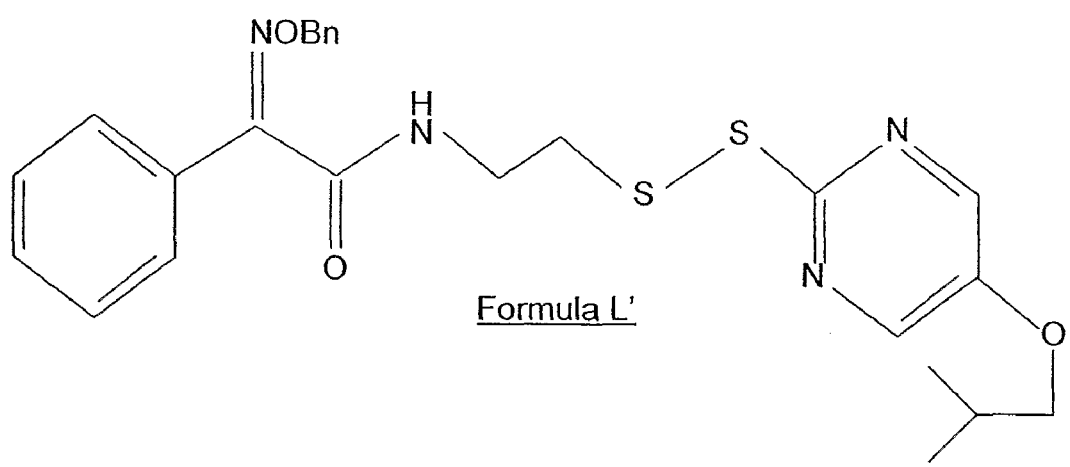
Figure 4C:
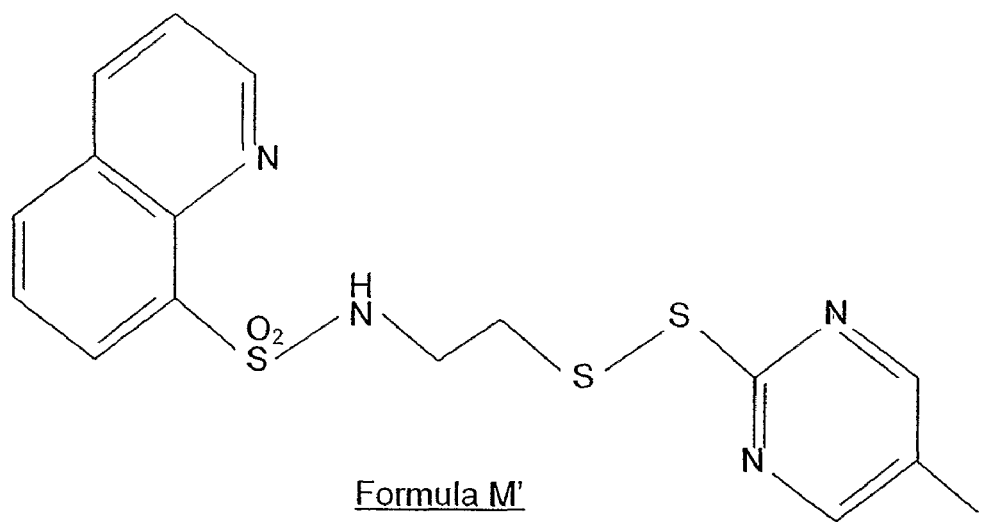
Figure 4D:
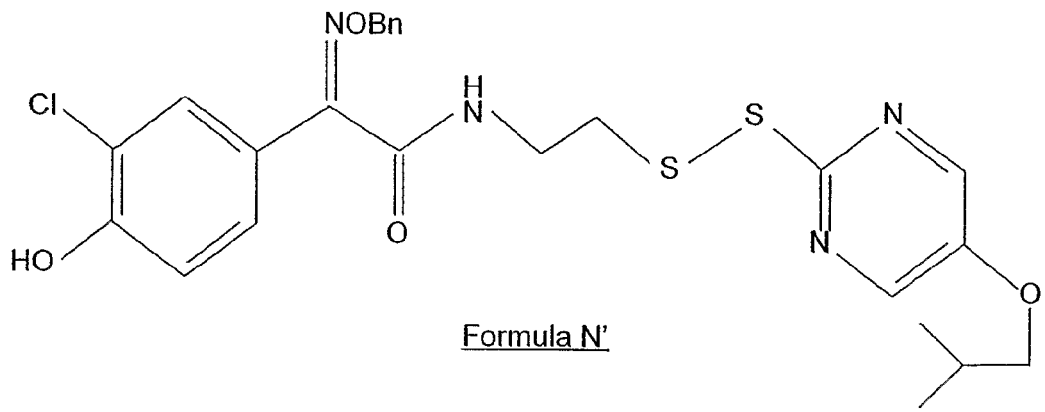
Figure 4D:
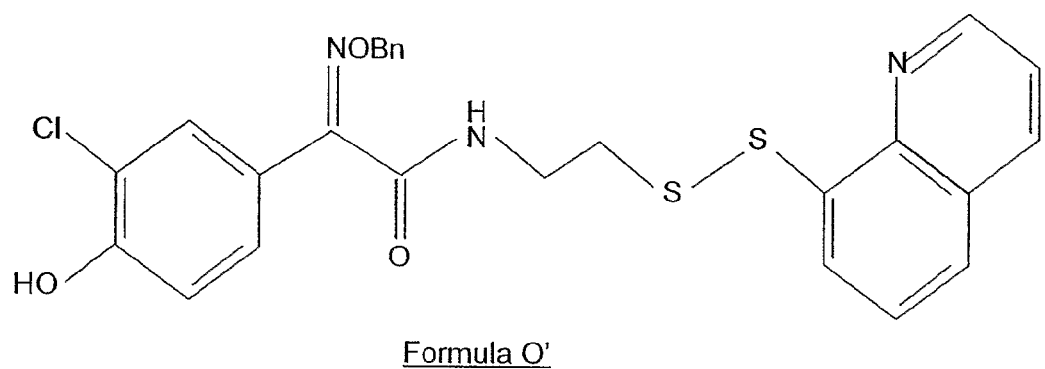
Figure 4D:
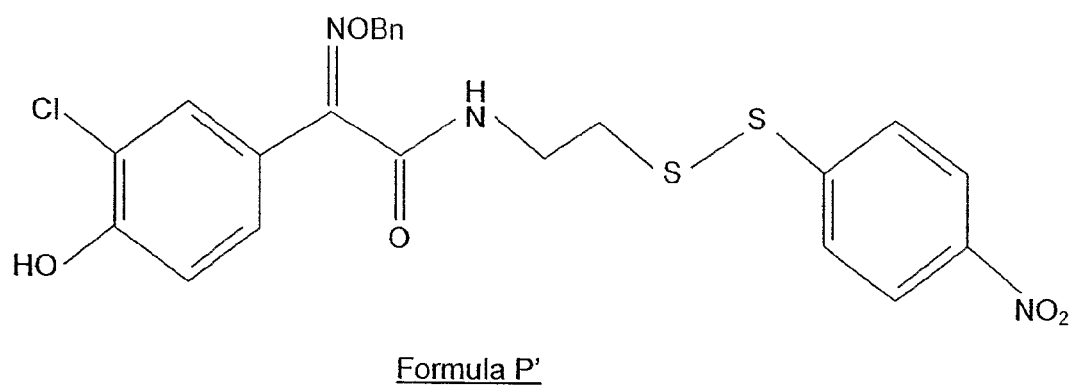
Figure 4E:
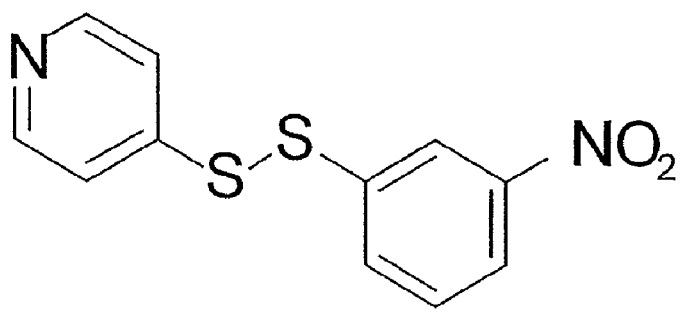
Figure 4E:
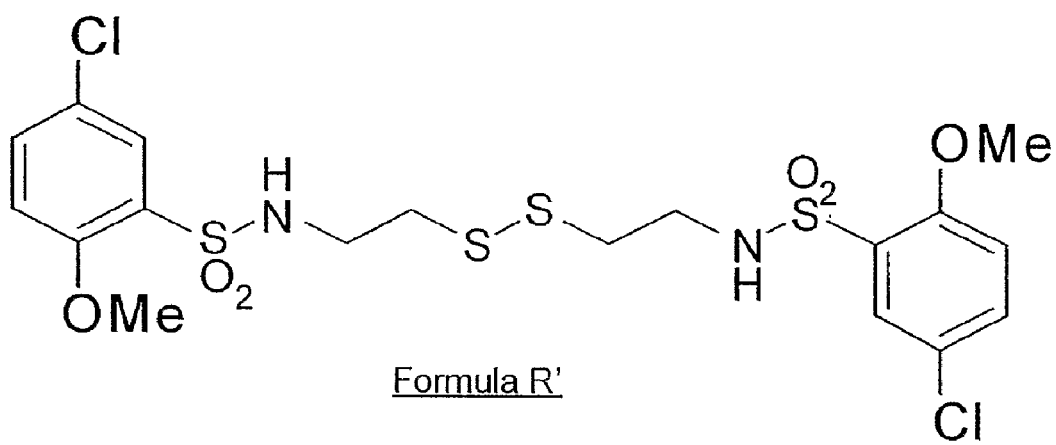
Figure 4E:
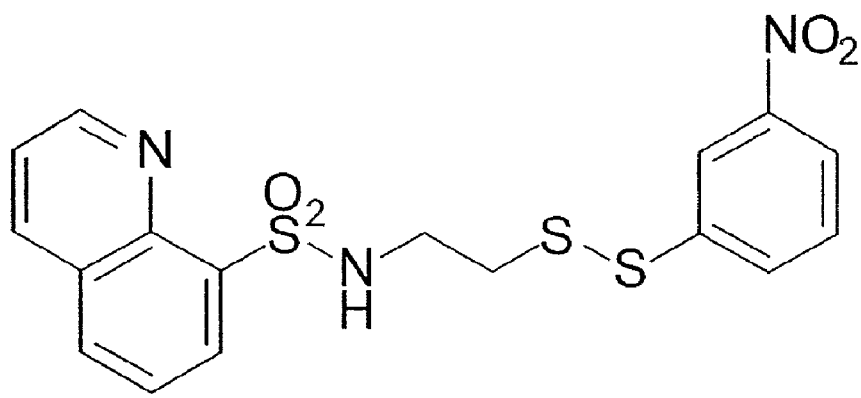
Figure 4F:
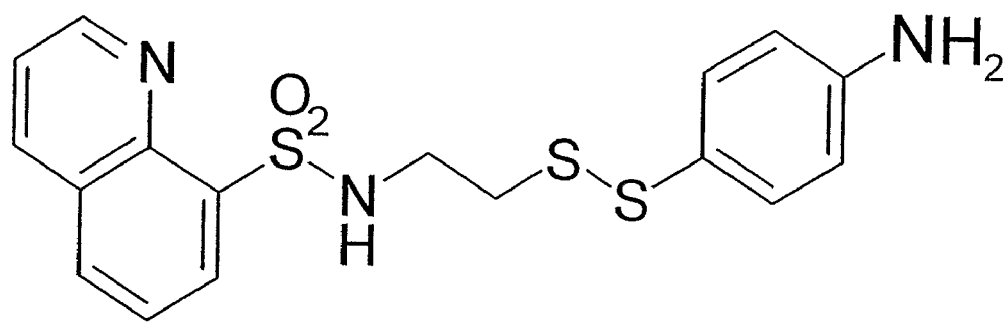
Figure 4F:
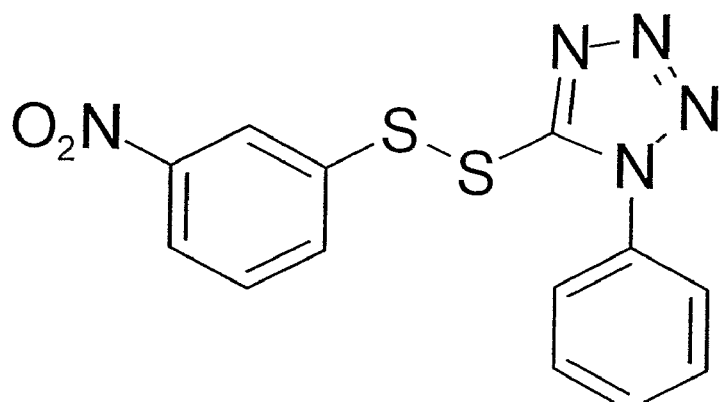
Figure 4F:
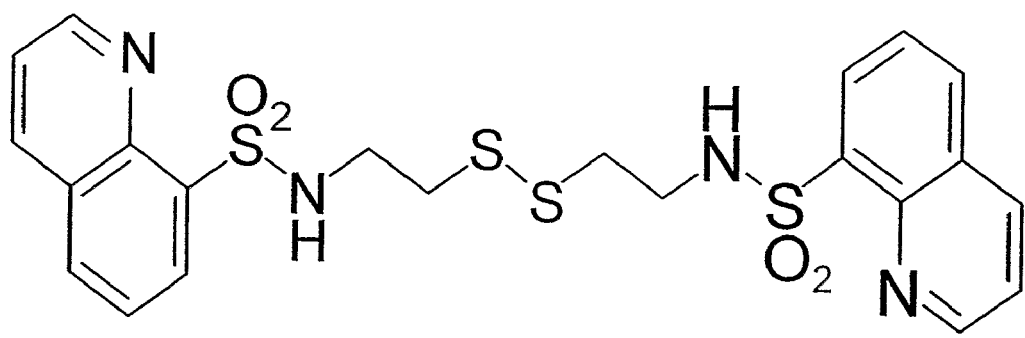
Figure 4G:
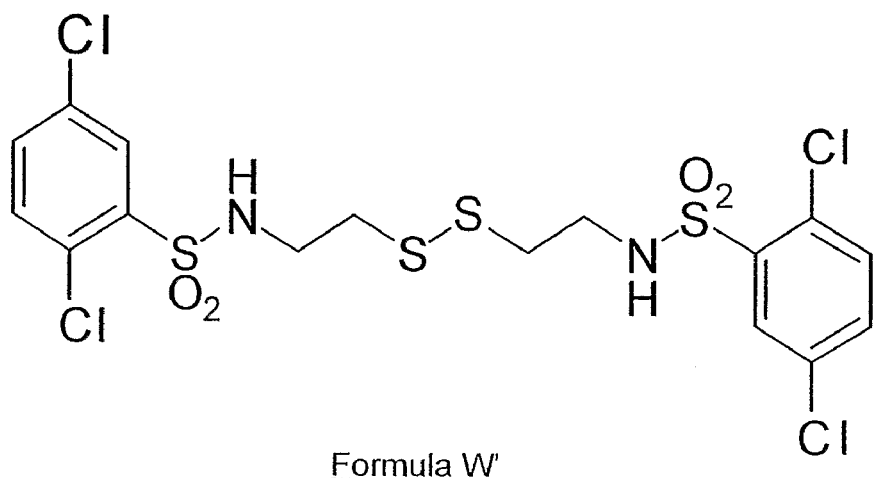
Figure 4G:
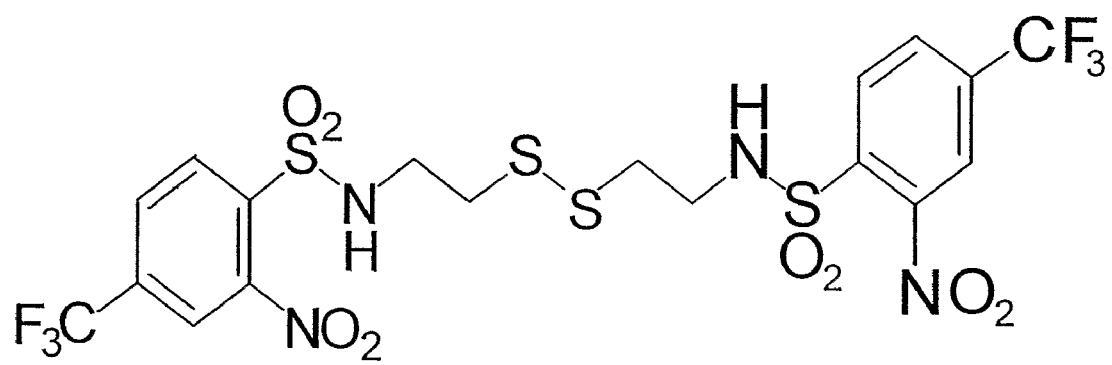

FIGS. 2A and 2B illustrate exemplar embodiments of formulae for HIF inhibitors. The HIF inhibitors include, but are not limited to, formula A', formula B', formula C', and formula D'. Formula A', formula B', formula C', and formula D' each can include an "X" group such as, but not limited to, X1', X2', X3', X4', X5', X6', X7', and X8' (e.g., formula A'/X1', formula B'/X8', and so on).

FIGS. 3A through 3G illustrate exemplar embodiments of formulae for HIF inhibitors. The HIF inhibitors include, but are not limited to, formula E, formula F, formula G, formula H, formula I, formula J, formula K, formula L, formula M, formula N, formula O, formula P, formula Q, formula R, formula S, formula T, formula U, formula V, formula W, and formula X.

In embodiments, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89, R90, R91, R92, R93, R94, R95, R96, R97, R98, R99, R100, R101, R102, R103, R104, R105, R106, R107, R108, R109, R110, R111, R12, R113, R114, R115, R116, R17, R118, R119, R120, R121, R122, R123, R124, R125, R126, R127, R128, R129, R130, R131, R132, R133, R134, R135, R136, R137, R138, R139, R140, R141, R142, R143, R144, R145, R146, R147, R148, R149, R150, R151, R152, R153, R154, R155, R156, R157, R158, R159, R160, R161, R162, and R163, can each independently be selected from groups that enhance one or more of the following HIF inhibitor properties of the HIF inhibitor: enhance the solubility of the HIF inhibitor, the ADME properties, enhance the pharmacology, enhance the pharmacodynamics of the HIF inhibitor, enhance the pharmacokinetics of the HIF inhibitor, diminish toxicity, augment bioavailability, and combinations thereof.

In other embodiments, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89, R90, R91, R92, R93, R94, R95, R96, R97, R98, R99, R100, R101, R102, R103, R104, R105, R106, R107, R108, R109, R110, R111, R112, R113, R114, R115, R116, R17, R118, R119, R120, R121, R122, R123, R124, R125, R126, R127, R128, R129, R130, R131, R132, R133, R134, R135, R136, R137, R138, R139, R140, R141, R142, R143, R144, R145, R146, R147, R148, R149, R150, R151, R152, R153, R154, R155, R156, R157, R158, R159, R160, R161, R162, and R163, can each independently be selected from groups such as, but not limited to, H, OH, a branched or unbranched $C_{1-12}$ alkyl group, an alkenyl group, an alkoxy group, an aryl group, a heterocycle group, an imidazole group, a substituted imidazole group, an alkyl substituted aryl group, a halogen substituted aryl group, a halogen group, an amine group, $NO_2$, and an acyl group.

In other embodiments, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89, R90, R91, R92, R93, R94, R95, R96, R97, R98, R99, R100, R101, R102, R103, R104, R105, R106, R107, R108, R109, R10, R111, R112, R113, R114, R115, R116, R117, R118, R119, R120, R121, R122, R123, R124, R125, R126, R127, R128, R129, R130, R131, R132, R133, R134, R135, R136, R137, R138, R139, R140, R141, R142, R143, R144, R145, R146, R147, R148, R149, R150, R151, R152, R153, R154, R155, R156, R157, R158, R159, R160, R161, R162, and R163, can each independently be selected from groups such as, but not limited to, H, OH, a branched or unbranched $C_{1-12}$ alkyl group, an alkoxy group, an aryl group, a heterocycle group, an imidazole group, an alkyl substituted aryl group, a halogen substituted aryl group, a halogen group, an amine group, and an acyl group.

In other embodiments, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89, R90, R91, R92, R93, R94, R95, R96, R97, R98, R99, R100, R101, R102, R103, R104, R105, R106, R107, R108, R109, R110, R11, R112, R113, R114, R15, R116, R117, R118, R119, R120, R121, R122, R123, R124, R125, R126, R127, R128, R129, R130, R131, R132, R133, R134, R135, R136, R137, R138, R139, R140, R141, R142, R143, R144, R145, R146, R147, R148, R149, R150, R151, R152, R153, R154, R155, R156, R157, R158, R159, R160, R161, R162, and R163, can each independently be selected from groups such as, but not limited to, H, OH, a halogen, an alkyl group, an alkoxy group, and an alkenyl group.

In other embodiments, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89, R90, R91, R92, R93, R94, R95, R96, R97, R98, R99, R100, R101, R102, R103, R104, R105, R106, R107, R108, R109, R110, R11, R112, R113, R114, R115, R16, R17, R118, R119, R120, R121, R122, R123, R124, R125, R126, R127, R128, R129, R130, R131, R132, R133, R134, R135, R136, R137, R138, R139, R140, R141, R142, R143, R144, R145, R146, R147, R148, R149, R150, R151, R152, R153, R154, R155, R156, R157, R158, R159, R160, R161, R162, and R163, can each independently be selected from groups such as, but not limited to, H, OH, a halogen, an alkyl group, and an alkoxy group.

FIGS. 4A through 4G illustrate exemplar embodiments of formulae for HIF inhibitors. The HIF inhibitors include, but are not limited to, formula E', formula F', formula G', formula H', formula I', formula J', formula K', formula L', formula M', formula N', formula O', formula P', formula Q', formula R', formula S', formula T', formula U', formula V', formula W', and formula X'.

Figure 5A:
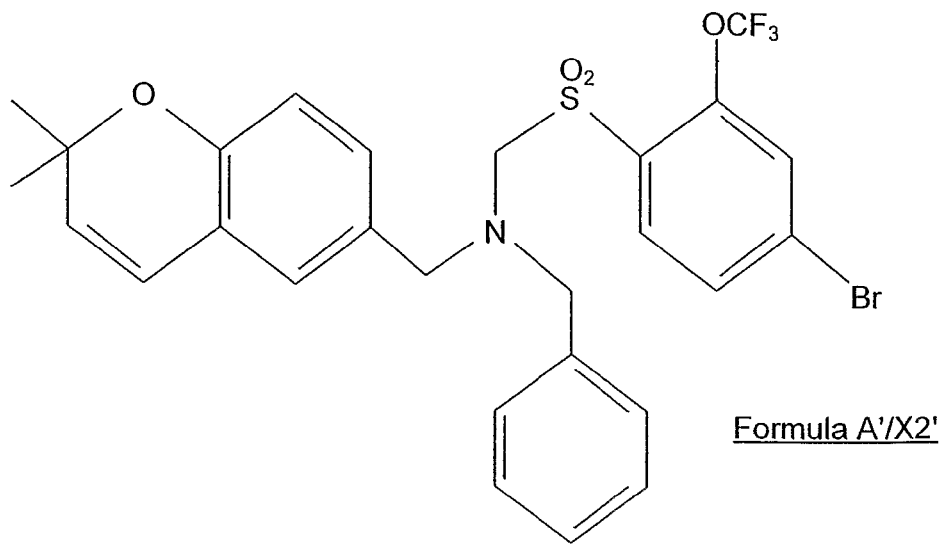
FIGS. 5A through 5D illustrate exemplar embodiments of formula for HIF inhibitors.
Figure 5A:
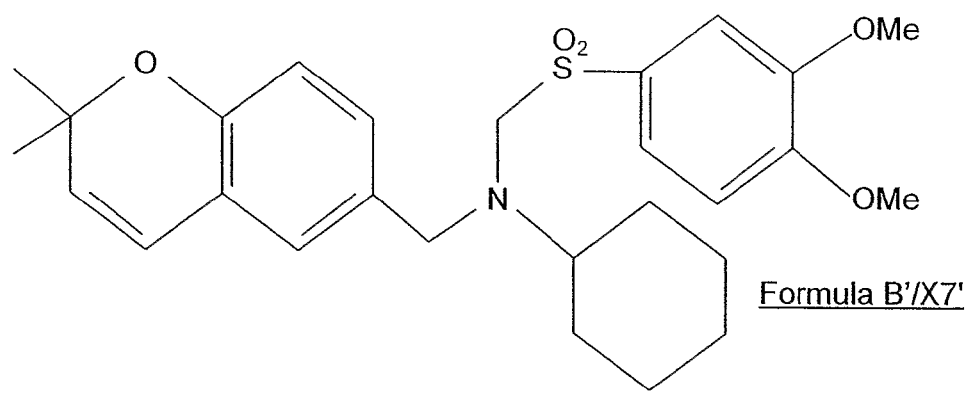
Figure 5A:
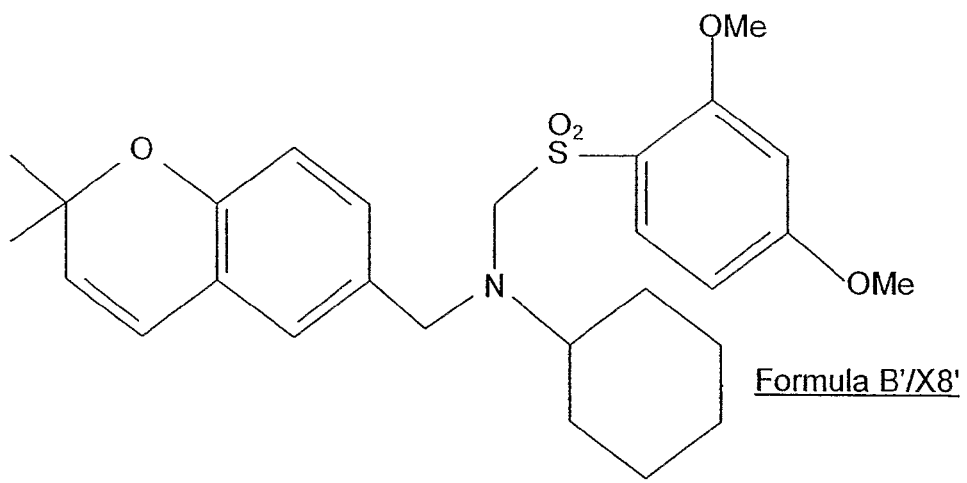
Figure 5B:
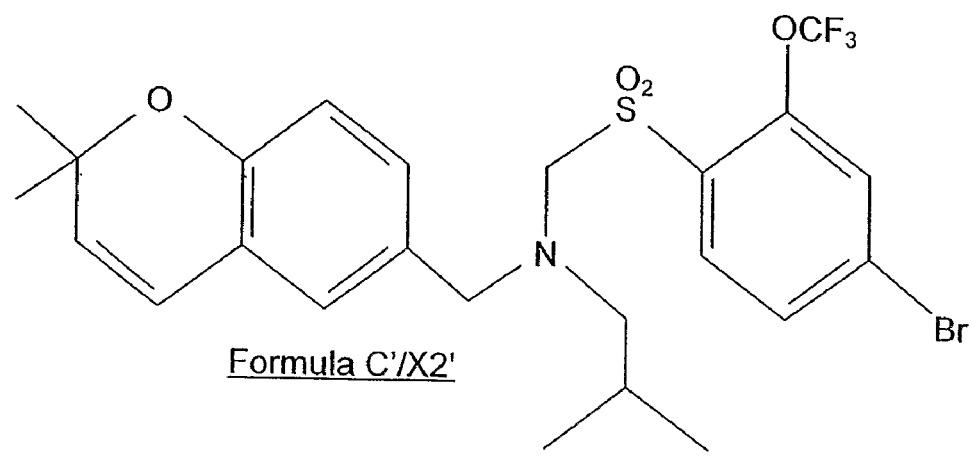
Figure 5B:
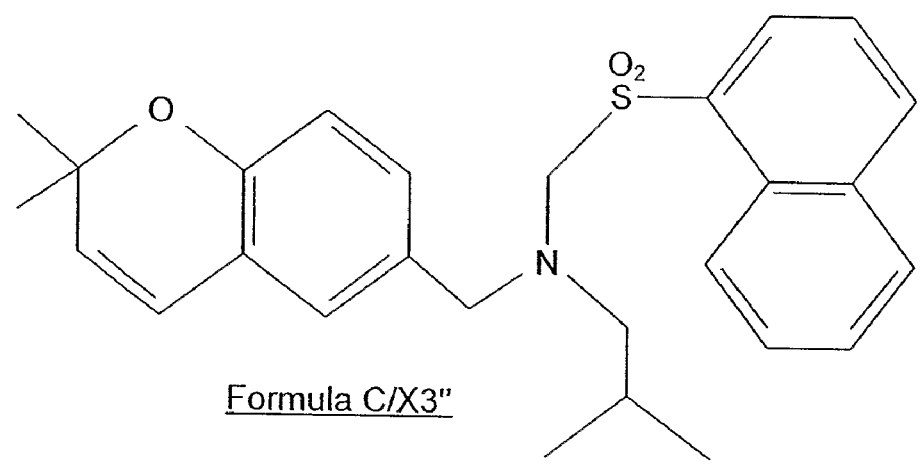
Figure 5B:
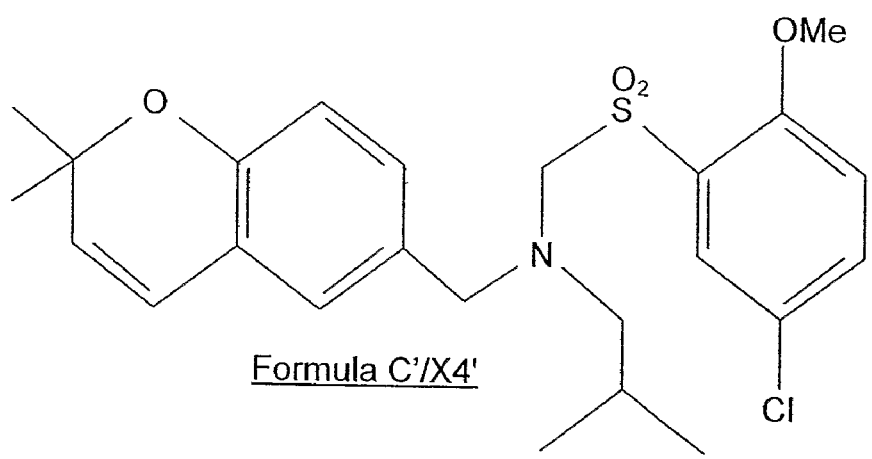
Figure 5C:
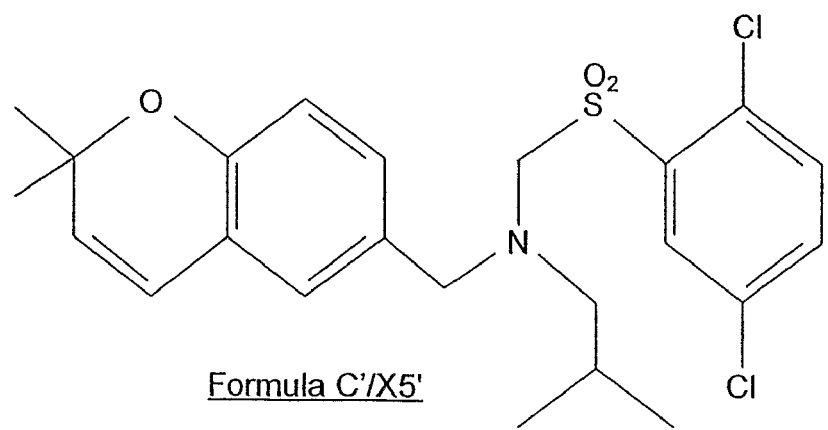
Figure 5C:
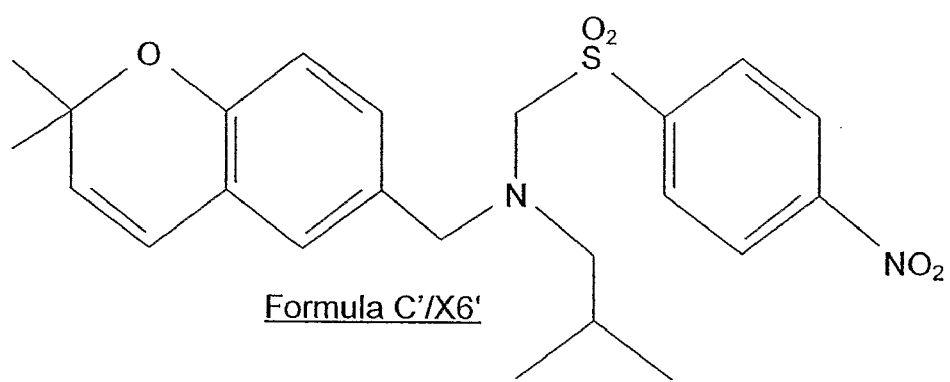
Figure 5C:
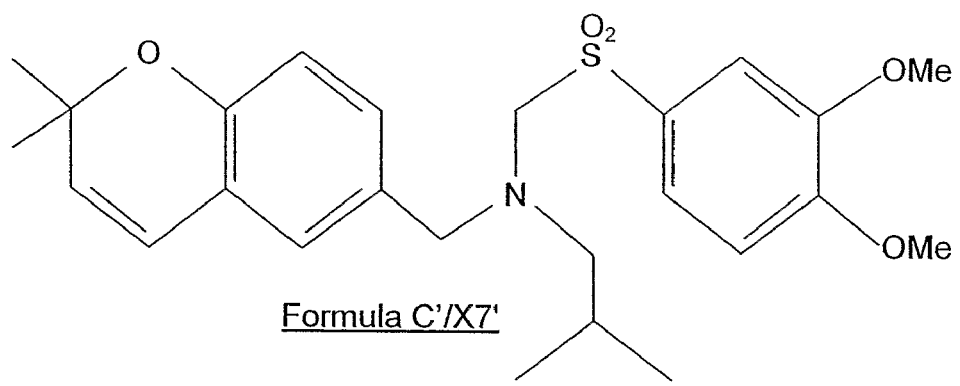
Figure 5D:
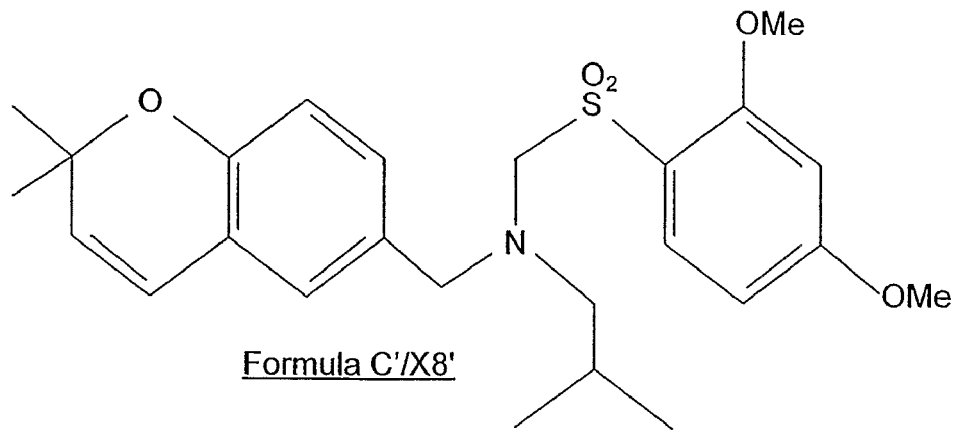
Figure 5D:
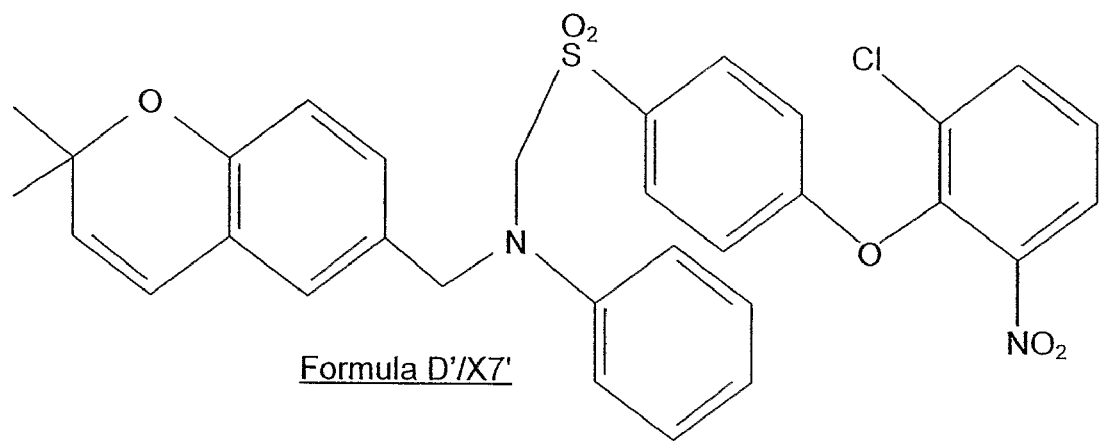
Figure 5D:
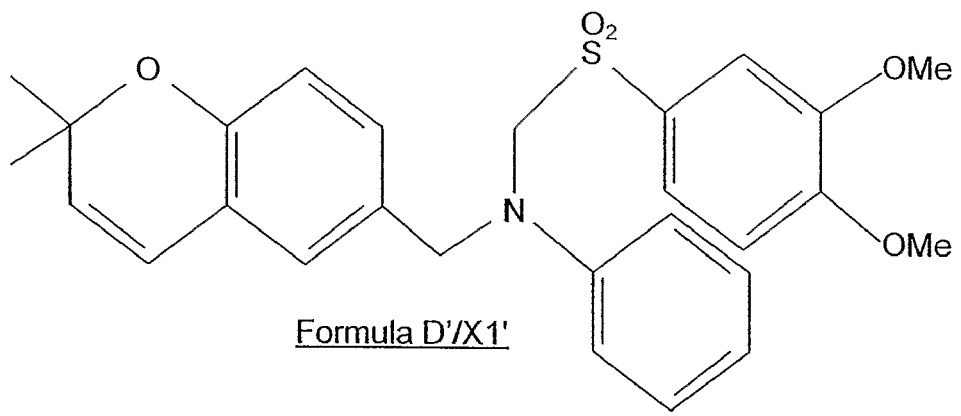

FIGS. 5A through 5C illustrate exemplar embodiments of formulae for HIF inhibitors. These include, but are not limited to, formula A'/X2', formula B'/X7', formula B'/X8', formula C'/X2', formula C'/X3', formula C'/X4', formula C'/X5', formula C'/X6', formula C'/X7', formula C'/X8', formula D'/X1', and formula D'/X7'. In particular, the HIF-1 inhibitors include, but are not limited to, formula B'/X7', formula B'/X8', formula C'/X7', formula C'/X8', and formula D'/X7'.

Figure 6:
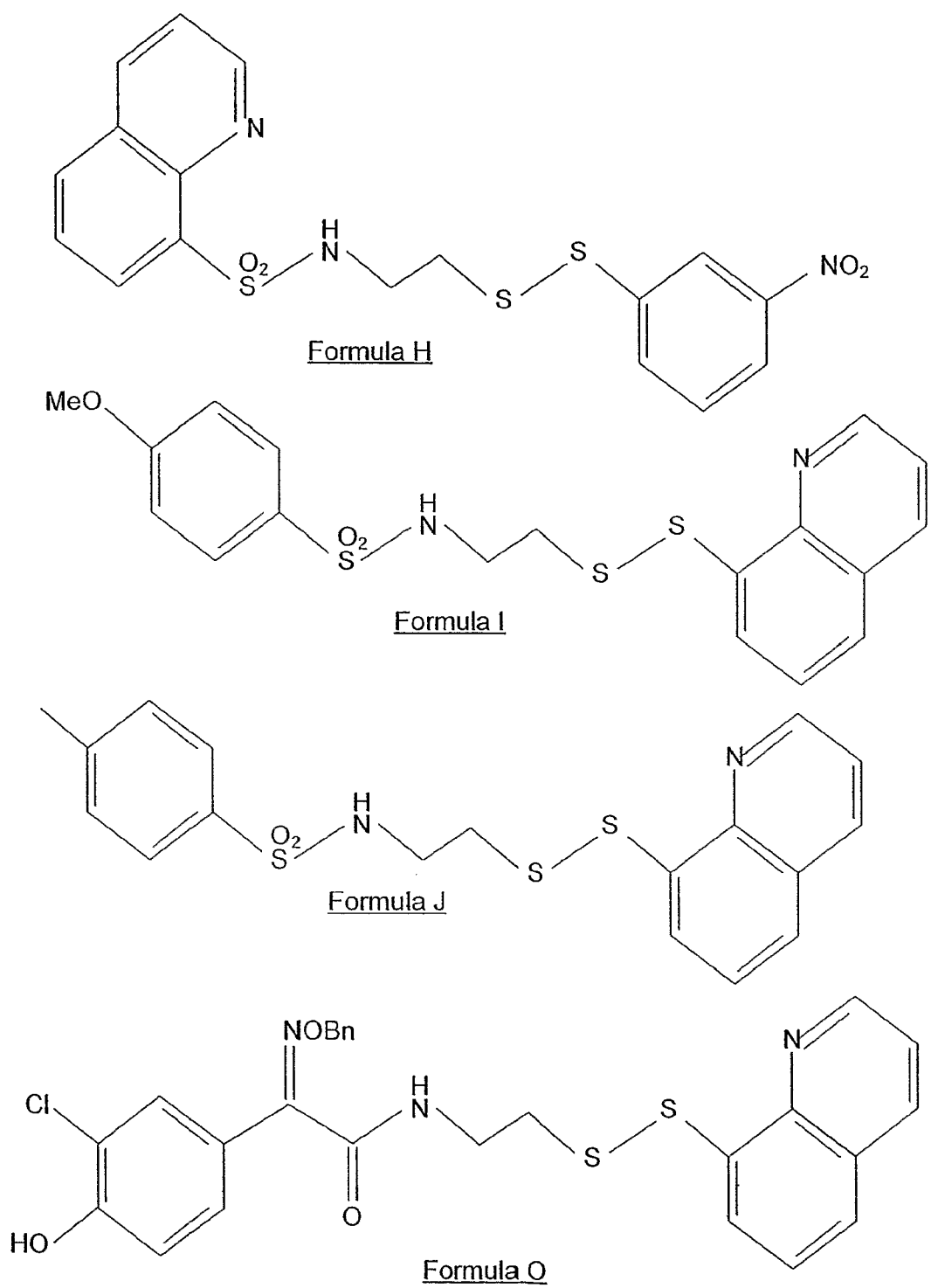
FIG. 6 illustrates exemplar embodiments of formula for HIF inhibitors.

FIG. 6 illustrates exemplar embodiments of formulae for HIF inhibitors. These include, but are not limited to, formula H', formula I', formula J', formula P', formula Q', formula R', formula S', formula T', formula U', formula V', formula W', and formula X'.

In another embodiment, the HIF inhibitor (e.g., HIF inhibitors shown in FIGS. 1-8) is a derivative of the disclosed compounds, including, but not limited to, an oxidation, reduction, or hydrolysis reaction product of the disclosed compounds, particularly those compounds in that a nitrogen containing ring, for example an imidazole ring, has been opened.

The HIF inhibitors were synthesized using methods and techniques for benzopyran synthesis known in the art. See for example, Nicolaou, K. C. et al. Natural Product-like Combinatorial Libraries Based on Privileged Structures 1. General Principles and Solid-Phase Synthesis of Benzopyrans. J. Am. Chem. Soc. 122:9939-9953 (2000); Nicolaou, K. C. et al. Natural Product-like Combinatorial Libraries Based on Privileged Structures. 2. Construction of a 10,000-Membered Benzopyran Library by Directed Split-and-Pool Chemistry Using NanoKans and Optical Encoding. J. Am. Chem. Soc. 122:9954-9967 (2000); Nicolaou, K. C. et al. Natural Product-like Combinatorial Libraries Based on Privileged Structures Natural Product-like Combinatorial Libraries Based on Privileged Structures 3. The "Libraries from Libraries" Principle for Diversity Enhancement of Benzopyran Libraries. J. Am. Chem. Soc. 122:9968-9976 (2000), which are incorporated by reference in their entirety.

Methods of Use

Some embodiments of the present disclosure are directed to modulating (e.g., interfering, inhibiting, or blocking) signal transduction through the HIF (e.g., HIF-1, HIF-2, and HIF-3) pathway. Such inhibition can be accomplished by binding of HIF or molecules associated with HIF with the disclosed HIF inhibitor compounds or their derivatives to render HIF inactive or unavailable. Alternatively, the HIF pathway can be inhibited, in whole or in part, by preventing the expression of HIF in a cell (through preventing HIF mRNA transcription, post-transcriptional modification of HIF mRNA, translation of HIF mRNA, posttranslational modification of HIF protein and HIF stability). HIF inhibition can also be achieved by interfering with the binding of HIF or HIF complexes to the hypoxia responsive element.

One embodiment provides a method for the treatment or prevention of a hypoxia-related pathology by administering to a host, for example a mammal, in need of such treatment, an HIF inhibiting amount of disclosed HIF inhibitor compounds, compositions, derivatives, pharmaceutically acceptable salts, prodrugs, or combinations thereof.

An embodiment provides a method for the treatment or prevention of a disease related to vascularization (e.g., diseases of the eye (e.g., cataract, glaucoma, macular degeneration, and diabetic retinopathy)) by administering to a host, for example a mammal, in need of such treatment, an HIF-inhibiting amount of disclosed HIF inhibitor compounds, compositions, derivatives, pharmaceutically acceptable salts, prodrugs, or combinations thereof.

Another embodiment provides a method of modulating HIF activity in a cell, for example a eukaryotic cell, by contacting the cell with an HIF-inhibiting amount of the disclosed HIF inhibitor compounds, compositions, derivatives, pharmaceutically acceptable salts, prodrugs, or combinations thereof.

Still another embodiment provides a method of treating or preventing cancer or a tumor in a host by administering to the host a HIF inhibiting amount of the disclosed HIF inhibitor compounds, compositions, derivatives, pharmaceutically acceptable salts, prodrugs, or combinations thereof.

Cancer is a general term for diseases in which abnormal cells accumulate and divide without control. Cancer cells can invade nearby tissues and can spread through the bloodstream and lymphatic system to other parts of the body. It has been discovered that the administration of an HIF-1 inhibitor to a host, for example a mammal, inhibits or reduces cancer, tumor growth or formation, and the metastasis of tumor cells.

There are several main types of cancer, and the disclosed compositions can be used to treat any type of cancer. For example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled, and coordinated unit, a tumor is formed. Generally, a solid tumor is an abnormal mass of tissue that usually does not contain cysts or liquid areas (although some brain tumors do have cysts and central necrotic areas filled with liquid). A single tumor may even have different populations of cells within it with differing processes that have gone awry, including cancer stem cells. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors, yet such cancers are supported by angiogenesis in the bone marrow that may also be inhibited by the HIF inhibitors. The compositions described herein can be used to reduce, inhibit, or diminish the proliferation of tumor cells, and thereby assist in reducing the size of a tumor. In particular, the disclosed compositions are useful for the treatment of solid tumors or pathologies in areas of hypoxia. Cancers can also have genetic alterations that lead to constitutive HIF expression independently of hypoxia.

Representative cancers that may be treated with the disclosed compositions and methods include, but are not limited to, bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others. Additional cancers are described in World Cancer report, World Health Organization and International Agency for Research on Cancer, edited by B W Steward and P Kleihues, Lyon France 2003; IARC Press (ISBN 92 832 0411 5), which is incorporated herein by reference.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (e.g., that with a very different environment, not normally conducive to their growth), and continue their rapid growth and division in this new location. This is called metastasis. Once malignant cells have metastasized, achieving cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, benign gliomas can be just be as life threatening as malignant lesions. An example of this would be a benign tumor in the brain, which can grow and occupy space within the skull, leading to increased pressure on the brain. The compositions provided herein can be used to treat benign or malignant tumors.

Accordingly, one embodiment provides a method of modulating gene transcription, for example the transcription of VEGF, erythropoietin, glucose transporter-1, glycolytic enzymes, or tyrosine hydroxylase, in a cell, for example a tumor or cancer cell, by contacting the cell with an HIF inhibiting amount of one or more of the disclosed HIF inhibitor compounds, pharmaceutical salts, prodrugs, or derivatives thereof. Alternatively, such transcription can be inhibited in a host by administering to the host an HIF inhibiting amount of the disclosed HIF inhibitor compounds and compositions.

Another embodiment provides a method of modulating gene expression in a tumor cell by contacting the tumor cell with an HIF modulating amount of one or more of the disclosed HIF inhibitor compounds, compositions, pharmaceutically acceptable salts, derivatives or prodrugs thereof. The modulation of the HIF pathway with the disclosed HIF inhibitor compounds and compositions can occur at transcriptional, translational and/or post-translational levels.

Another embodiment provides a method for treating a hypoxia-related pathology by administering the combination of the disclosed HIF-inhibitor compounds and compositions with conventional chemotherapeutic agents and/or radiotherapy. For example, the disclosed HIF inhibitor compositions can be used to treat a pathology, for example a proliferative pathology such as cancer or other hypoxia related pathology independently or in combination with one another or with one or more additional therapeutic agents. Representative therapeutic agents include but are not limited to antibiotics, anti-inflammatories, anti-oxidants, analgesics, radioisotopes, antibodies, chemotherapeutic agents such as nascapine, paclitaxel, nocodazole, vinca alkaloids, adriamycin, alkeran, Ara-C, BICNU, busulfan, CCNU, carboplatinum, cisplatinum, cytoxan, daunorubicin, DTIC, 5-FU, fludarabine, hydrea, idarubicin, ifosfamide, methotrexate, mithramycin, mitomycin, mitoxantrone, nitrogen, mustard, velban, vincristine, VP-16, gemcitabine (gemzar), herceptin, irinotecan (camptosar, CPT-11), leustatin, navelbine, rituxan, STI-571, taxotere, topotecan, (hycamtin), xeloda (capecitabine), zevelin, BCNU, taxol, temozolomide, and combinations thereof.

It will be appreciated that the HIF inhibitor compounds of the present disclosure can be used in combination with radiation therapy or surgical procedures for the treatment of a pathology, for example cancer.

In one embodiment, the disclosed HIF inhibitor composition is administered to a host having developed resistance to conventional chemotherapeutic agents.

Pharmaceutical HIF Inhibitor Compositions

Pharmaceutical HIF inhibitor compositions and dosage forms of the disclosure include a pharmaceutically acceptable salt of disclosed or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. For example, a dosage form used in the acute treatment of a disease or disorder may contain larger amounts of the active ingredient, for example the disclosed compounds or combinations thereof, than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Typical pharmaceutical compositions and dosage forms comprise one or more excipients. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure comprise a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, and more preferably in an amount of from 50 mg to 500 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665):1818-22 (2004)).

Oral Dosage Forms

Pharmaceutical HIF inhibitor compositions of the disclosure that are suitable for oral administration can be presented as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms of the compositions of the disclosure are prepared by combining the pharmaceutically acceptable salt of disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Due to their ease of administration, tablets and capsules represent the most advantageous solid oral dosage unit forms, in which case solid pharmaceutical excipients are used. If desired, tablets can be coated by standard aqueous or non-aqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the disclosure include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Plano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

This disclosure further encompasses lactose-free pharmaceutical compositions and dosage forms, wherein such compositions preferably contain little, if any, lactose or other mono- or di-saccharides. As used herein, the term "lactose-free" means that the amount of lactose present, if any, is insufficient to substantially increase the degradation rate of an active ingredient.

Lactose-free compositions of the disclosure can comprise excipients which are well known in the art and are listed in the USP(XXI)/NF (XVI), which is incorporated herein by reference. In general, lactose-free compositions comprise a pharmaceutically acceptable salt of an HIF inhibitor, a binder/filler, and a lubricant in pharmaceutically compatible and pharmaceutically acceptable amounts. Preferred lactose-free dosage forms comprise a pharmaceutically acceptable salt of the disclosed compounds, microcrystalline cellulose, pre-gelatinized starch, and magnesium stearate.

This disclosure further encompasses anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms

Pharmaceutically acceptable salts of the disclosed HIF inhibitor compounds can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite®AP143 (Rohm&Haas, Spring House, Pa. USA).

One embodiment of the disclosure encompasses a unit dosage form that includes a pharmaceutically acceptable salt of the disclosed compounds (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the disclosure. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the disclosure include, but are not limited to, the OROS® Push-Pull™, Delayed Push-Pull™, Multi-Layer Push-Pull™, and Push-Stick™ Systems, all of which are well known. See, e.g. worldwide website alza.com. Additional OROS® systems that can be used for the controlled oral delivery of compounds and compositions of the disclosure include OROS®-CT and L-OROS®; see, Delivery Times, vol. 11, issue II (Alza Corporation).

Conventional OROS® oral dosage forms are made by compressing a drug powder (e.g., a HIF inhibitor salt) into a hard tablet, coating the tablet with cellulose derivatives to form a semi-permeable membrane, and then drilling an orifice in the coating (e.g., with a laser). Kim, Chemg-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility. Because HIF inhibitor salts and complexes of this disclosure (e.g., an HIF inhibitor sodium salt) may be far more soluble in water than an HIF inhibitor itself, they may be well suited for osmotic-based delivery to patients. This disclosure does, however, encompass the incorporation of an HIF inhibitor, and non-salt isomers and isomeric mixtures thereof, into OROS® dosage forms.

A specific dosage form of the HIF inhibitor compositions of the disclosure includes: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent the exit orifice and in direct or indirect contacting relationship with the expandable layer; and a flow-promoting layer interposed between the inner surface of the wall and at least the external surface of the drug layer located within the cavity, wherein the drug layer includes a salt of an HIF inhibitor, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the disclosure includes: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of a HIF inhibitor, or a polymorph, solvate, hydrate, dehydrate, co-crystal, anhydrous, or amorphous form thereof. See U.S. Pat. No. 6,342,249, the entirety of which is incorporated herein by reference.

Parenteral Dosage Forms

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that alter or modify the solubility of a pharmaceutically acceptable salt of a HIF inhibitor disclosed herein can also be incorporated into the parenteral dosage forms of the disclosure, including conventional and controlled-release parenteral dosage forms.

Topical, Transdermal And Mucosal Dosage Forms

Topical dosage forms of the disclosure include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For nonsprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990).

Transdermal and mucosal dosage forms of the HIF inhibitor compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, Isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of an HIF inhibitor of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of an HIF inhibitor can be used to further adjust the properties of the resulting composition.

Kits

Typically, active ingredients of the pharmaceutical compositions of the disclosure are preferably not administered to a patient at the same time or by the same route of administration. This disclosure therefore encompasses kits which, when used by the medical practitioner, can simplify the administration of appropriate amounts of active ingredients to a patient.

A typical kit includes a unit dosage form of a pharmaceutically acceptable salt of an HIF inhibitor and optionally, a unit dosage form of a second pharmacologically active compound, such as an anti-proliferative agent, or an anti-cancer agent. In particular, the pharmaceutically acceptable salt of an HIF inhibitor is the sodium, lithium, or potassium salt, or a polymorph, solvate, hydrate, dehydrate, co-crystal, anhydrous, or amorphous form thereof. A kit may further include a device that can be used to administer the active ingredient. Examples of such devices include, but are not limited to, syringes, drip bags, patches, and inhalers.

Kits of the disclosure can further include pharmaceutically acceptable vehicles that can be used to administer one or more active ingredients (e.g., an HIF inhibitor). For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: water for injection USP; aqueous vehicles such as, but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Other embodiments are directed to the use of the disclosed compositions in the preparation of a medicament for the treatment hypoxia-related pathology.

EXAMPLES

Example 1

Genetically engineered LN229 cells (a human glioma cell line) which stably express the alkaline phosphatase reporter gene under the control of six copies of a hypoxia-responsive element was used to identify small-molecule inhibitors of the HIF-1/HRE pathway. The engineered LN229 cell line is disclosed in U.S. Provisional Patent Application No. 60/235,283, which is incorporated by reference in its entirety herein. Cells were seeded at 40,000 cells per well in 96-well plates. Compounds of interest with 2,2-dimethylbenzopyran motifs were added and the plates were incubated under hypoxia (1% $O_2$, 5% $CO_2$ and 94% $N_2$) at 37° C. for 24 h. Cells were then washed with phosphate-buffered saline and incubated with p-nitrophenyl phosphate at 37° C. for 30 min. The reaction was terminated by adding 3 N NaOH and the plates were read for absorbance at 405 nm. The anti-HIF-1/HRE activity of each compound was quantified as the decrease of percentage of alkaline phosphatase (AP) activity compared to the untreated control cells.

Figure 7:
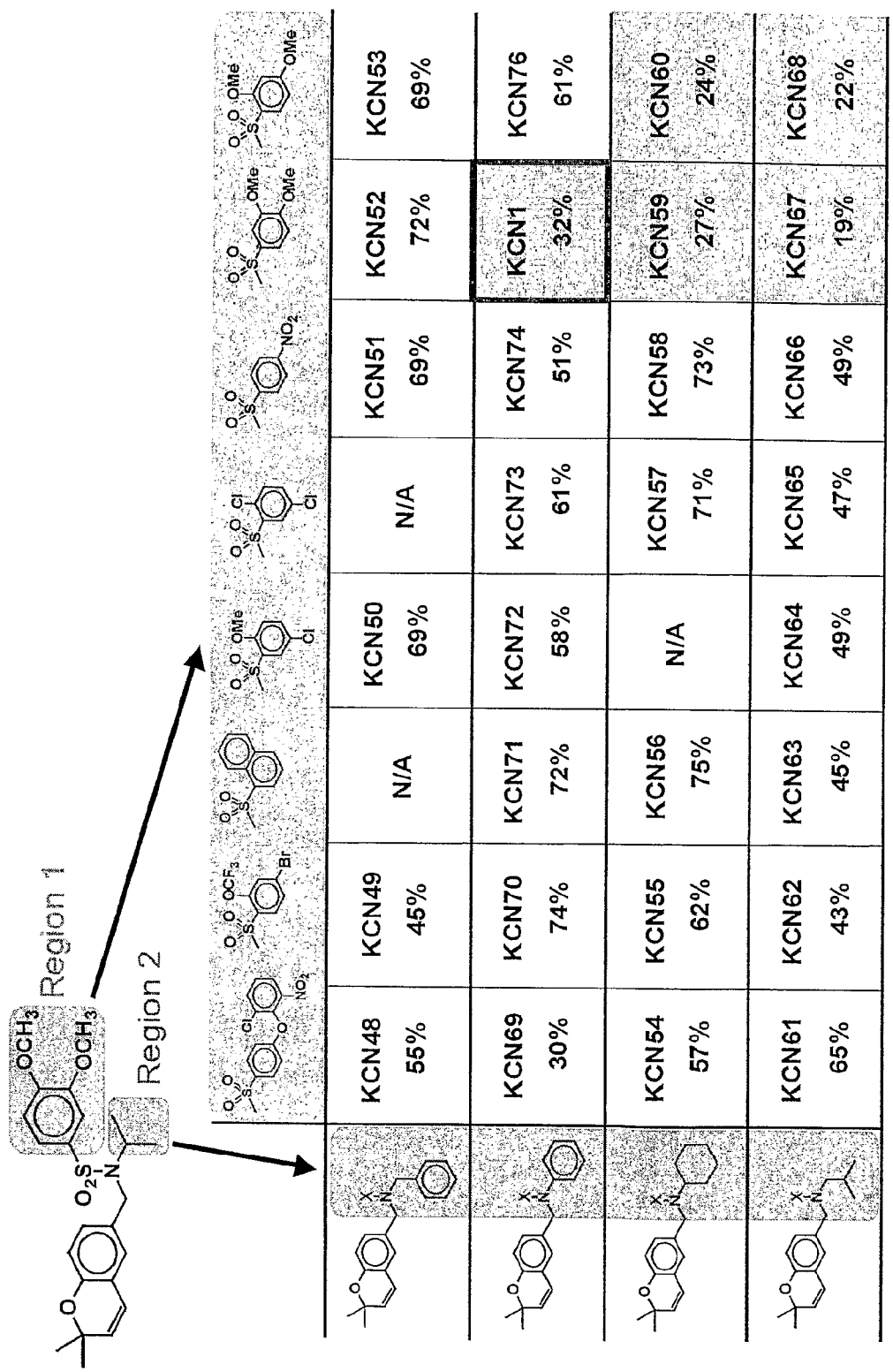
FIG. 7 illustrates exemplar HIF-inhibitor compounds that showed AP activity at 10 μM and contain a 2,2 dimethyl benzopyran motif.
Figure 8:
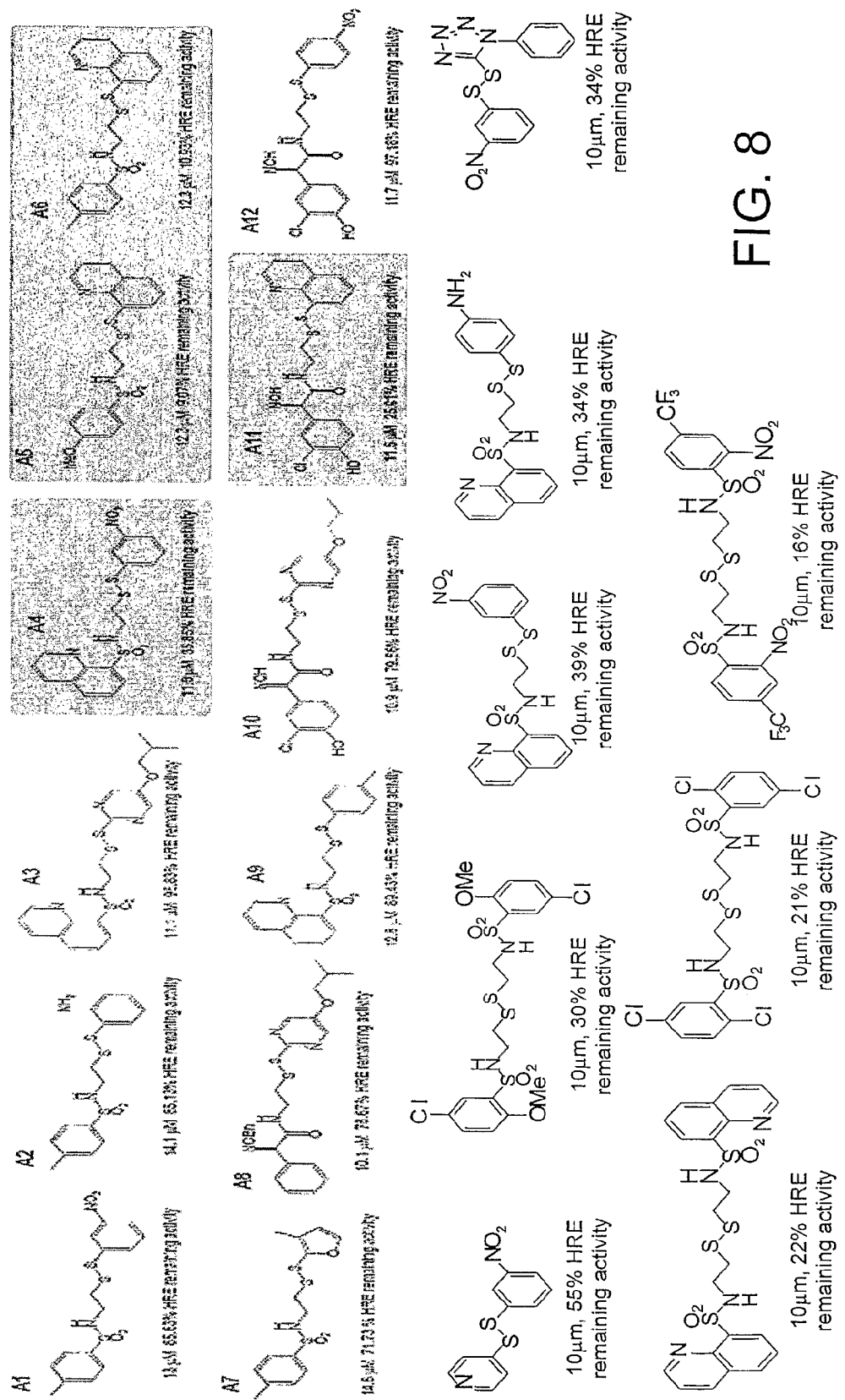
FIG. 8 illustrates exemplar HIF-inhibitor compounds that showed AP activity at 10 μM and harbor a psammaplin-like structure.
Figure 9:
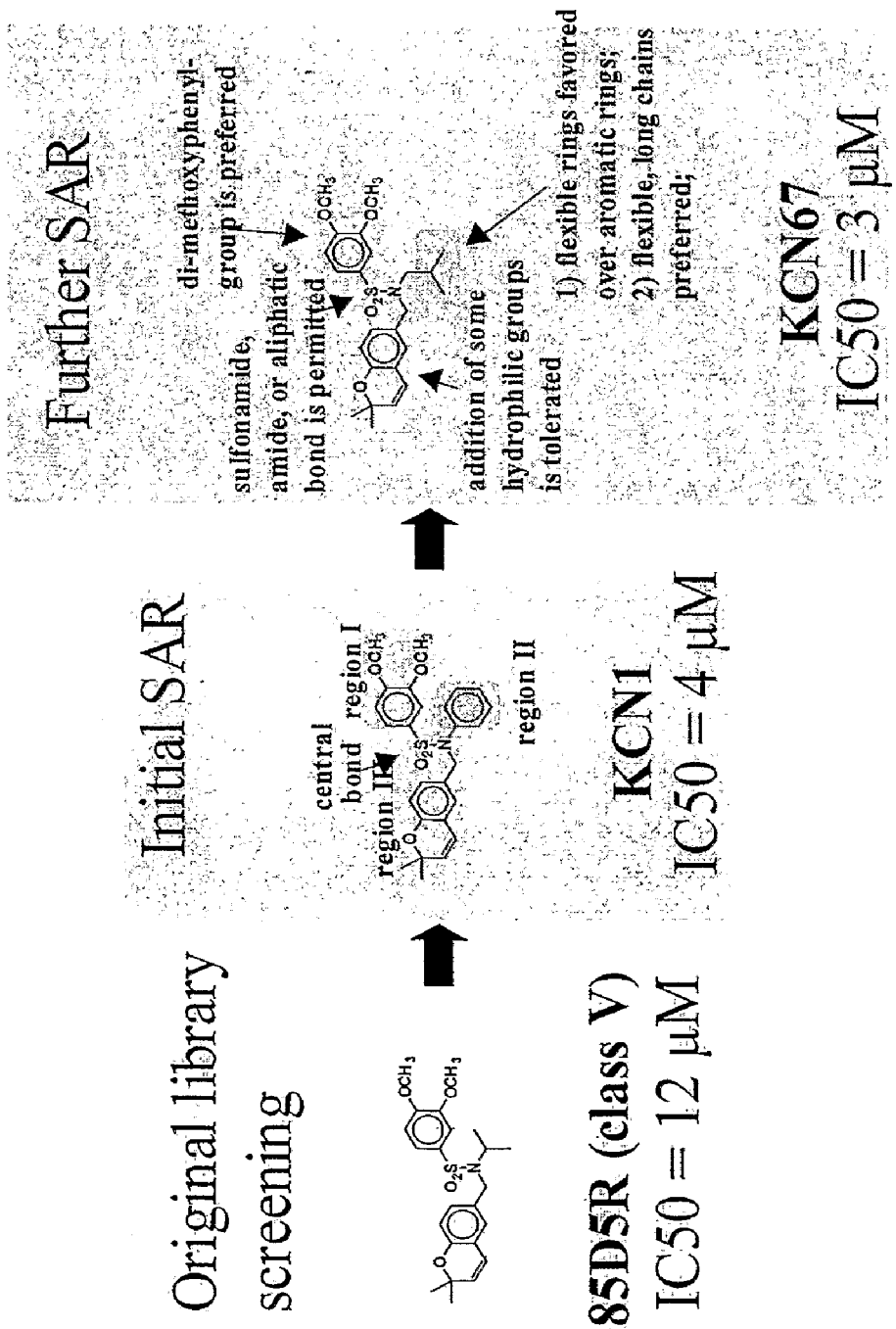
FIG. 9 illustrates a schematic of to exemplar HIF-inhibitors.

FIGS. 7 and 8 illustrate exemplar HIF-inhibitor compounds that showed AP activity at 10 µM. It should be noted that % indicated in FIGS. 7 and 8 represent percent of AP activity leftover after inhibition, e.g., the lower the percent the better the anti-HRE activity in this assay. FIG. 9 presents a summary schematic of the findings of the structure-activity relationship studies (SAR) on the initial HIF-inhibitor 85D5R. The inhibitory activity of this compound was improved by modifications in the regions I and II to generate compounds with improved acitivities (KCN1 and KCN67, as also seen in FIG. 7). Studies on the independent elimination of region III highlighted the resemblance with "psammaplins" and a number of psammaplins tested also exhibited anti-HRE activities in the bioassay (see FIG. 8).

Example 2

This example presents experiments that show HIF inhibitors can inhibit HIF-1 alpha and the growth of an aggressive human tumor (glioblastoma) in mice.

To screen for small molecule HIF-1 pathway inhibitors, a cell-based assay was established by stably transfecting a glioma cell line with a hypoxia-inducible alkaline phosphatase (AlkPhos) expression vector (LN229-HRE-AP). Exposure of the cells to hypoxia (1% $O_2$) induced reporter gene expression, which could be detected and quantitated by a calorimetric reaction. This bioassay was used to screen 10,000 natural product-like compounds built upon a 2,2-dimethylbenzopyran scaffolding motif. The 2,2-dimethylbenzopyran motif was chosen as a preferential synthetic scaffold for drug design because it is present in >4,000 natural products, is sufficiently lipophilic to ensure good cell membrane penetration and will generate compounds on average of less than 500 Da which are likely to cross the BBB and reach hypoxic tumor (Nicolaou, K. C. et al. Natural Product-like Combinatorial Libraries Based on Privileged Structures 1. General Principles and Solid-Phase Synthesis of Benzopyrans. J. Am. Chem. Soc. 122:9939-9953 (2000); Nicolaou, K. C. et al. Natural Product-like Combinatorial Libraries Based on Privileged Structures. 2. Construction of a 10,000-Membered Benzopyran Library by Directed Split-and-Pool Chemistry Using NanoKans and Optical Encoding. J. Am. Chem. Soc. 122:9954-9967 (2000); Nicolaou, K. C. et al. Natural Product-like Combinatorial Libraries Based on Privileged Structures Natural Product-like Combinatorial Libraries Based on Privileged Structures 3. The "Libraries from Libraries" Principle for Diversity Enhancement of Benzopyran Libraries. J. Am. Chem. Soc. 122:9968-9976 (2000)).

Figure 10:
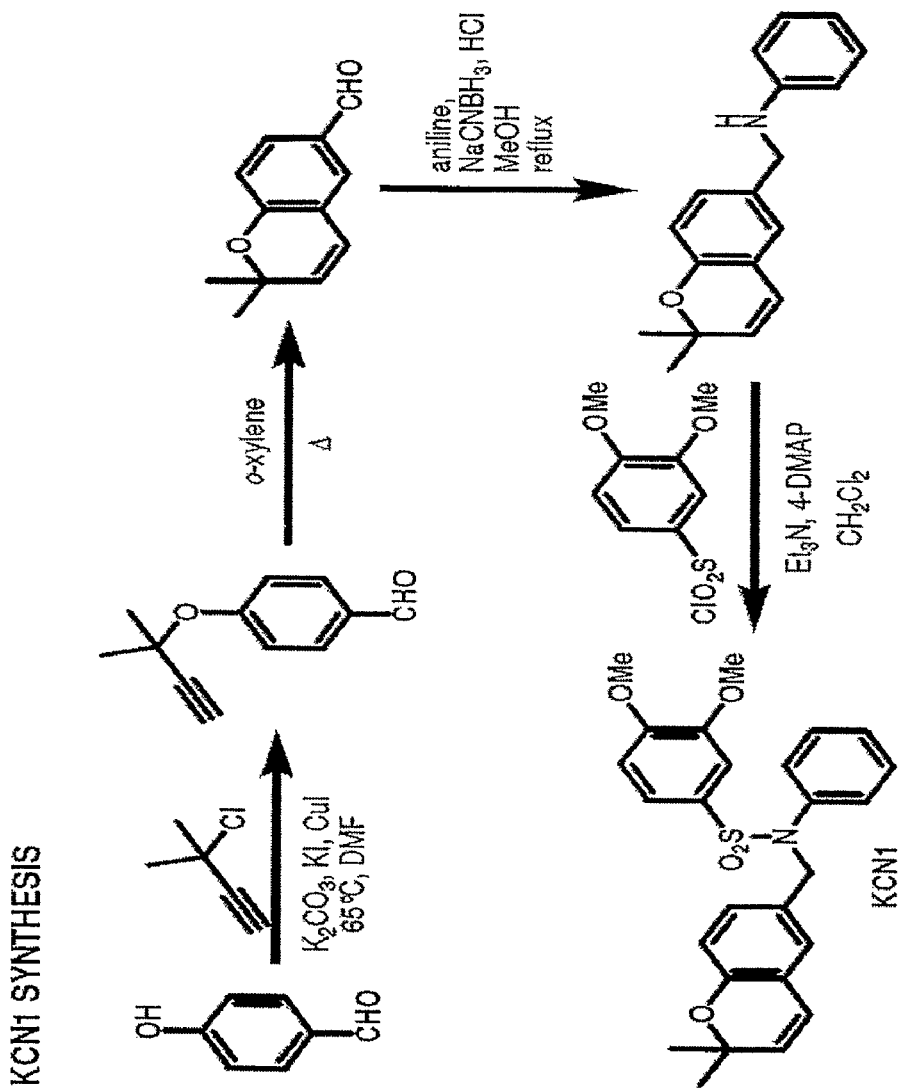
FIG. 10 illustrates an exemplar method of making KCN1 (Formula D'/X7' in FIGS. 2A and 2B).

One example of a compound found was KCN1 (formula D'/X7' in FIGS. 2A and 2B), a derivative with an improved $IC_{50}$ of ~4 uM and an experimental LogP of 3.9 (not shown; cLogP=5.8). Four grams of KCN1 have been synthesized for initial PK and anti-tumor studies. FIG. 10 illustrates an illustrative embodiment of a method for forming KCN1.

Figure 11:
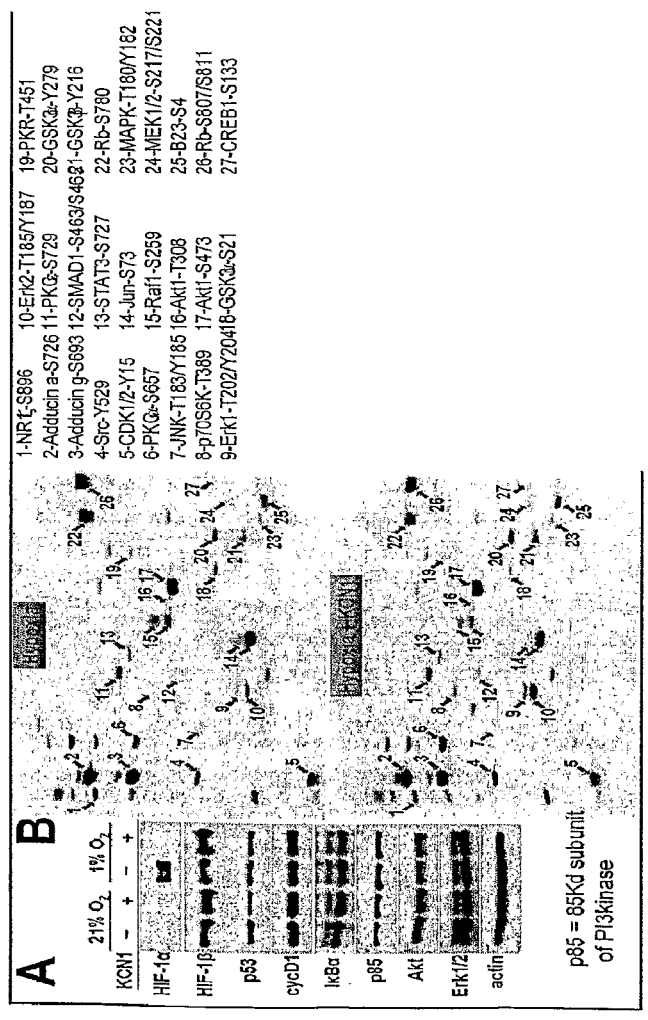
FIG. 11 illustrates an analysis of specificity of KCN1. LN229 cells were pre-treated with KCN1 (25 uM) for 1 h and then put in 1% $O_2$ for 5hrs. Cell extracts were analyzed by Western blot for levels of total proteins (FIG. 11 (A)) and phospho-proteins by multiplex Western FIG. 11 (B)). It should be noted that a strong increase of HIF-1α levels under hypoxia is inhibited by KCN1. Densitometry analysis showed the other proteins analyzed had only minimal changes in expression (<1.5 fold) in the same time frame.
Figure 11:
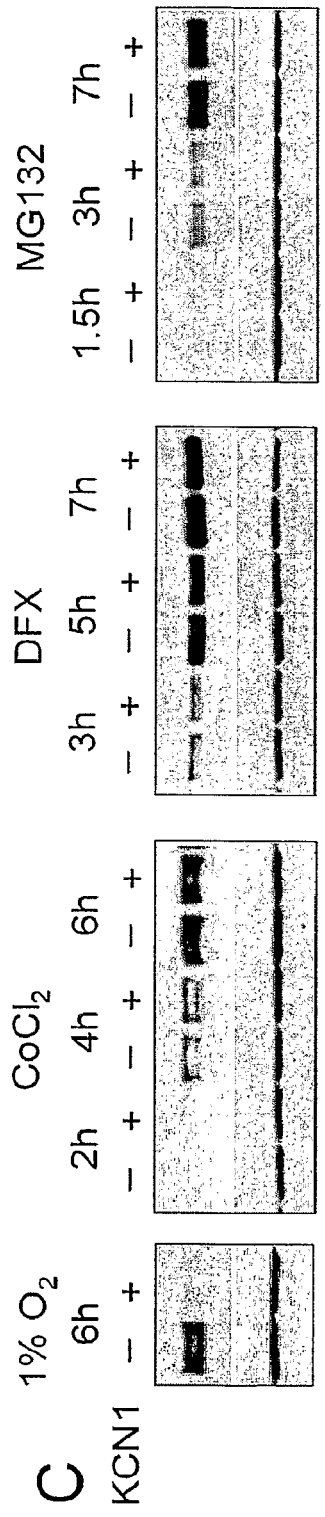

Extracts of normoxic and hypoxic cells were analyzed for changes in total protein expression levels mediated by KCN1 by Western blot at 5 hrs and strong anti-HIF-1α activity is detected. No changes were observed for signal transduction proteins (Akt, p85 PI3K subunit, Erk1/2), short-lived proteins (p53, IkBα, cyclin D1) or control proteins (HIF-1β and actin) (FIG. 11(A)). The above extracts were further analyzed to detect changes in the activity states of key signal transduction proteins by multiplex Western (Kinexus). This method allows the simultaneous screening of 37 different phospho-proteins involved in key cell signaling pathways. These results show that KCN1 has minimal effects (<1.5 fold) on the 27 of these proteins that show detectable phosphorylation in these cells (FIG. 11(B)). KCN1 inhibits only HIF-1α under hypoxic conditions (FIG. 11 (C)). Stabilization of HIF-1alpha under normoxia by $CoCl_2$, desferroxiamine or proteasome inhibitor MG132 is not inhibited by KCN1. This suggests that KCN1 has a unique mechanism of action, perhaps the targeting of a component of the HIF translation machinery operating specifically under hypoxia.

Figure 12:
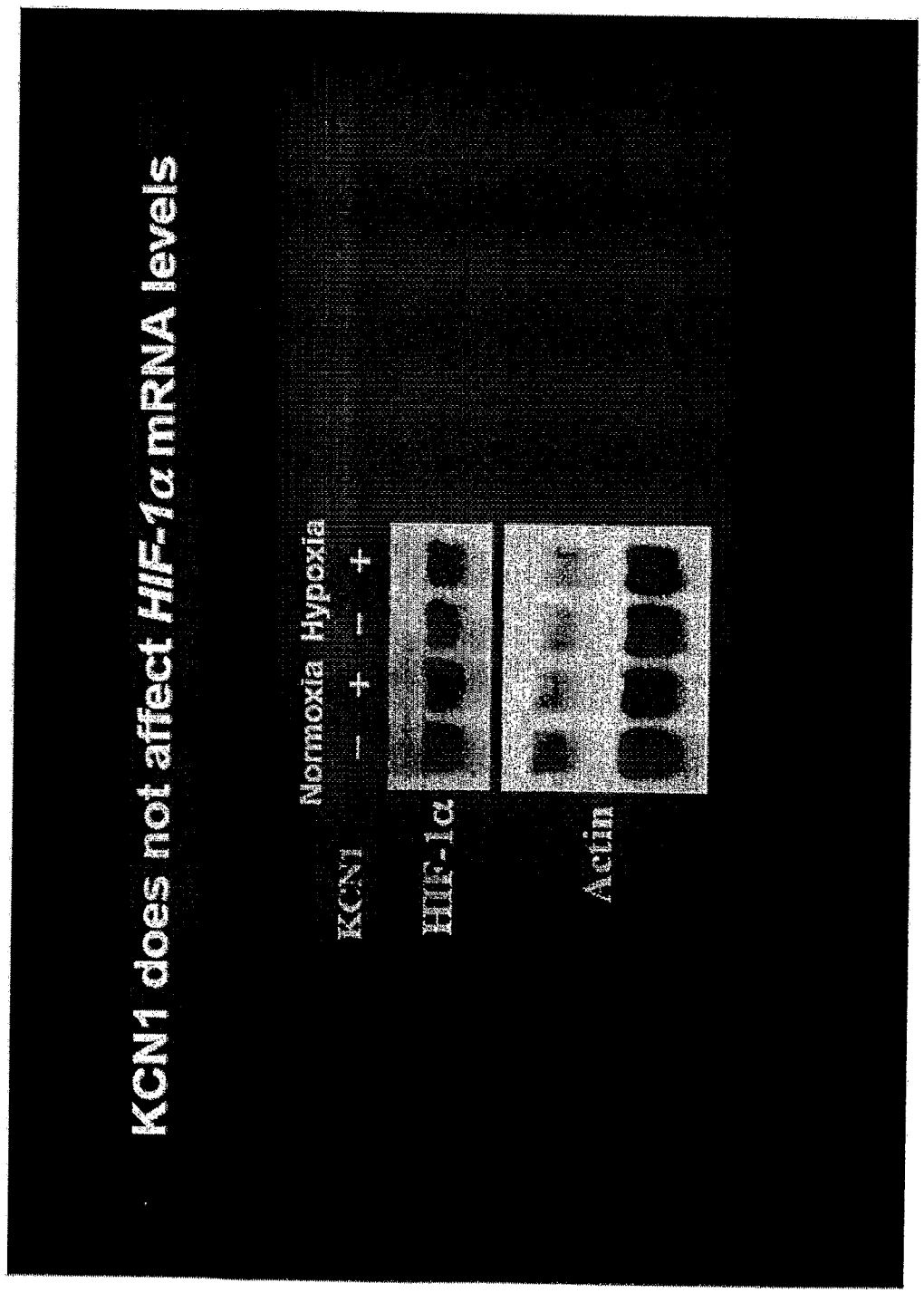
FIG. 12 illustrates that KCN1 does not affect HIF-1 alpha mRNA levels. To examine whether KCN1 might interfere with mRNA synthesis or stability Northern blots were performed. HIF-1 alpha mRNA levels remained constant with or without KCN1 treatment.
Figure 13:
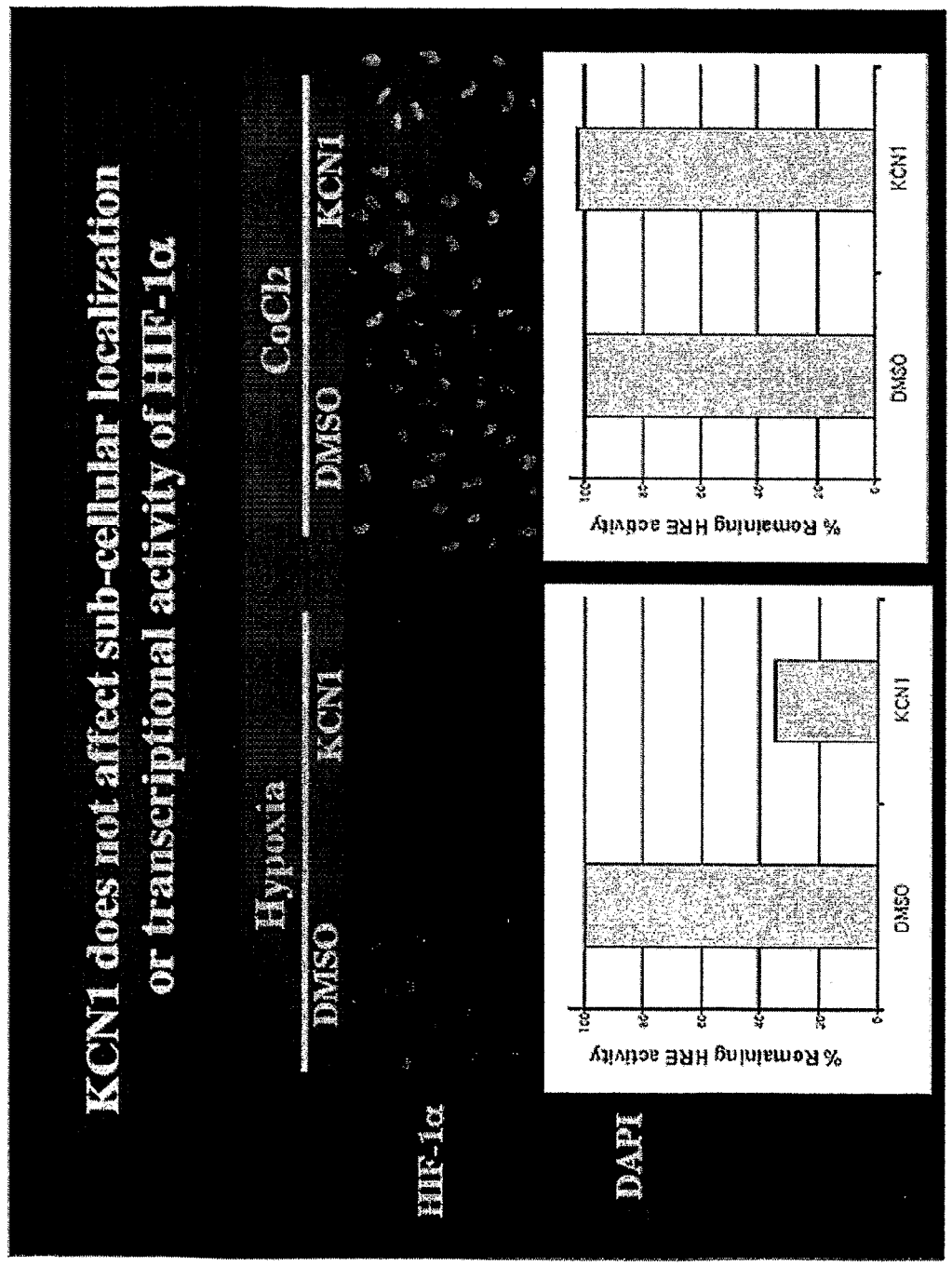
FIG. 13 illustrates that KCN1 does not affect sub-cellular localization or transcriptional activity of HIF-1 alpha. To examine whether KCN1 might interfere with the ability of HIF to translocate to the nucleus, its location was examined by microscopy in LN229 cells containing a stably integrated HRE-luciferase reporter construct. Under hypoxia KCN1 inhibits HIF accumulation and no HIF is seen in the nucleus or cytoplasm. Under $CoCl_2$ conditions HIF is chemically induced and its levels are not affected by KCN1. HIF is predominantly present in the cell's nuclei in both untreated and KCN1 treated cells, suggesting KCN1 does not interfere with nuclear accumulation. Measurement of HIF-induced luciferase activity (lower panel) confirms that HIF is transcriptionally active in the presence of KCN1 in the $CoCl_2$ treated cells.

To gain insight into the possible mechanism of action of KCN1 a number of experiments listed below were performed. First, an experiment focused on whether KCN1 might block HIF at the mRNA or protein level was performed. To examine whether KCN1 might interfere with HIF-1 alpha mRNA synthesis or stability, Northern blots were performed. HIF-1alpha mRNA levels remained constant with or without KCN1 treatment (FIG. 12). Second, an experiment focused on whether KCN1 might interfere with the ability of HIF to translocate to the nucleus was performed by examining its location by microscopy in LN229 cells. Under hypoxia KCN1 inhibits HIF accumulation, confirming the Western blot results and no HIF is seen in the nucleus or cytoplasm. Under $CoCl_2$ conditions, HIF is "chemically induced" and its levels are not affected by KCN1 as expected from the Western blots above (FIG. 11C). HIF is predominantly present in the cell nuclei in both untreated and KCN1 treated cells, suggesting KCN1 does not interfere with nuclear accumulation (FIG. 13).

Figure 14:
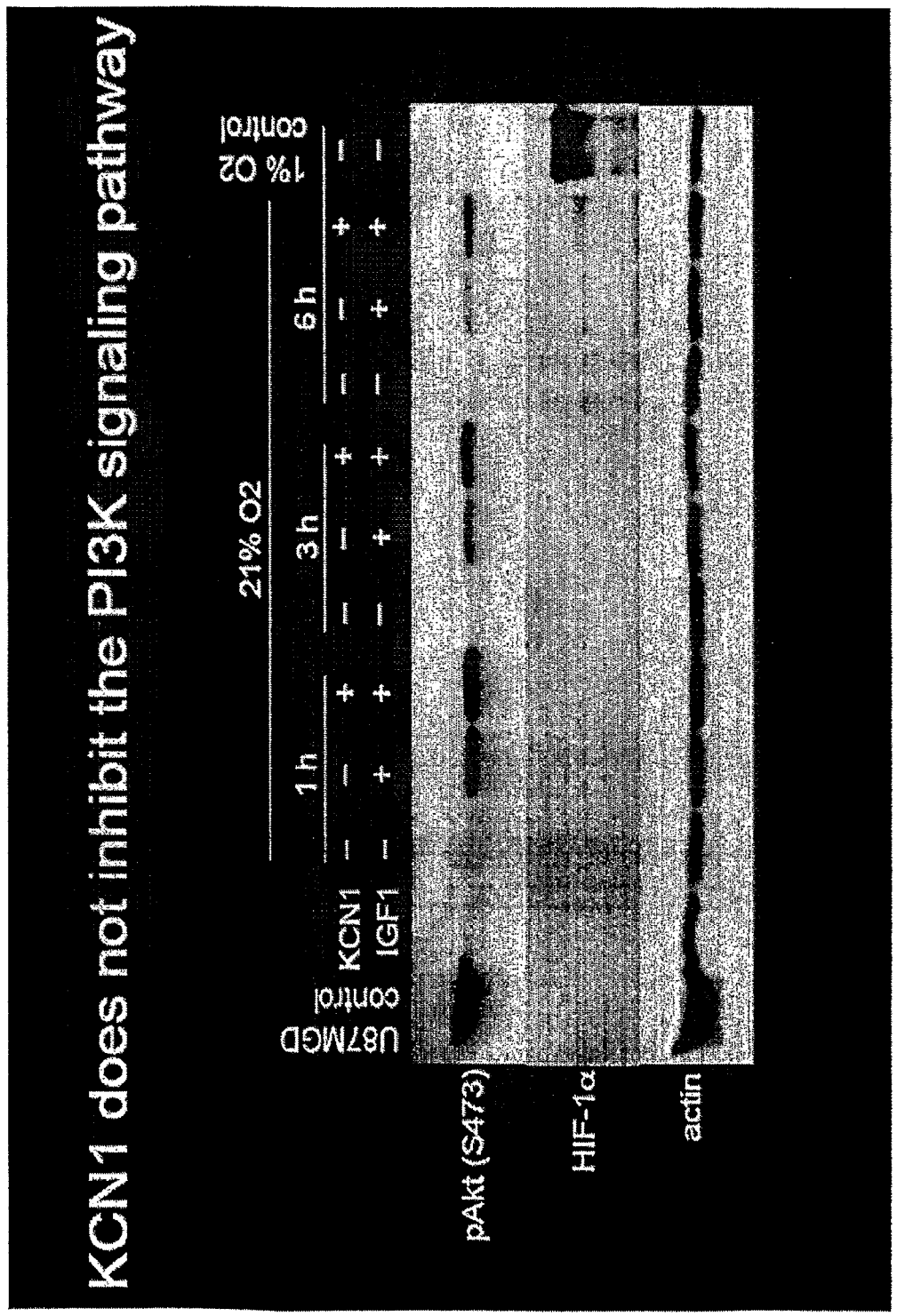
FIG. 14 illustrates that KCN1 does not inhibit the PI3K signaling pathway but stimulates Akt phosphorylation. Phosphorylation of Akt on S473 is rapidly induced upon IGF1 treatment and this signal is not inhibited by KCN1 at 1, 3, and 6 hrs. An increase in phospho-Akt is observed with KCN1 at 1, 3 and 6 hrs.

In addition, experiments focused on whether HIF present in the nucleus of the KCN1 and $CoCl_2$ treated cells was transcriptionally active were performed. It was found that the luciferase activity of the HRE-luciferase reporter present in the cells remained active, suggesting that KCN1 does not block HIF's ability to function as a transcription factor. Third, an experiment focused on whether KCN1 might interfere with HIF synthesis through the PI3 kinase/Akt/mTOR pathway that controls mRNA translation was performed. The effects of KCN1 on the phosphorylation of Akt in response to growth factor IGF1 (insulin growth factor 1) were examined. FIG. 14 shows that phosphorylation of Akt on Serine 473 is rapidly induced upon IGF1 treatment and this signal is not inhibited by KCN1 at 1, 3, and 6 hrs. Interestingly, an increase in phospho-Akt is observed with KCN1. The reasons for this are currently unclear, but this finding suggests that KCN1 might inhibit a phosphatase or increase the activity of a kinase. This finding might have therapeutic implications independently of the activities of KCN1 on HIF.

Figure 15:
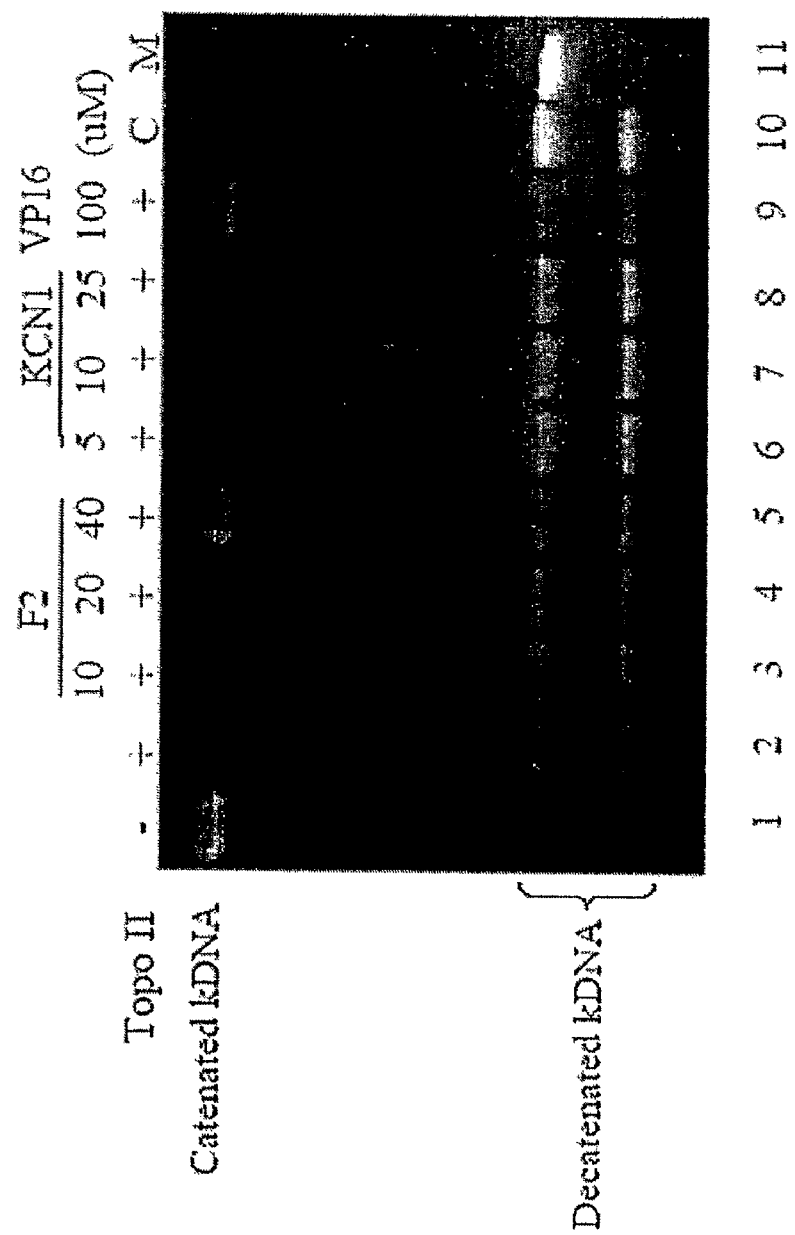
FIG. 15 illustrates that HIF inhibitor F2 (Psammaplin analogue) but not KCN1 inhibits topoisomerase II activity. Purified topo II activity with F2 or KCN1 was analyzed under normoxia using kDNA decatenation assay. To examine the activity, 1% agarose gel with ethidium bromide was used and it enabled to detect catenated kDNA and decatenated kDNA. In lanes 5 and 9, inhibition of topoisomerase II activity was detected as evidenced by the presence of catenated DNA.

Finally, an experiment focused on whether some of the HIF inhibitors might have an effect on topoisomerase function was performed. It has been reported in the literature that some HIF inhibitors may act via a topoisomerase-dependent mechanism (Rapisarda A et al 2004, Cancer Res 64-1475-82). KCN1 and psammaplin analogue F2 (FIG. 8) were tested and their inhibitory effect on topoisomerase II using a kinetoplast DNA decatenation assay (FIG. 15) was examined. F2 partially inhibits topo II activity at 40 uM in the assay as shown by the presence of catenated kDNA (upper band in ethidium bromide electrophoresis), similar to the inhibitory activity observed with 100 uM etoposide (VP16), a known topo II inhibitor in use in the clinic. In contrast, KCN1 did not inhibit topo II in this assay at concentrations that inhibit HIF (5-25 uM). These data suggest: that F2 may be a viable topo II inhibitor that can have therapeutic applications and that KCN1's ability to inhibit HIF is not linked to topo II inhibition and that KCN1 does not inhibit topo II at concentrations up to 25 uM.

Collectively, these results suggest that inhibitors of the present disclosure potently prevent HIF-1α stabilization under hypoxia within 5 hrs, while they do not perturb main cellular signaling events or stability of other short-lived proteins in the cells during the same time frame.

Figure 16:
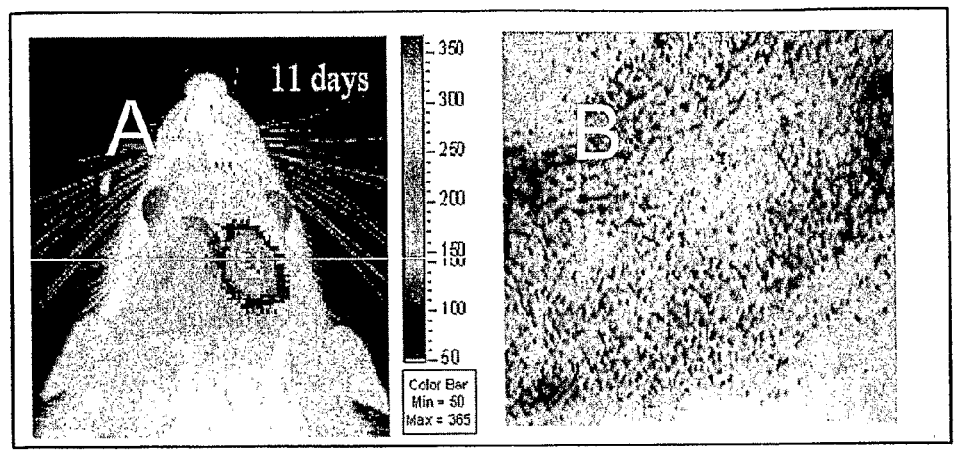
FIG. 16 illustrates (A) non-invasive imaging of HIF activity in 9 L intracranial rat glioma model of 11 days following tumor cell implantation and (B) histological stain: B-galactosidase on a section.
Figure 17:
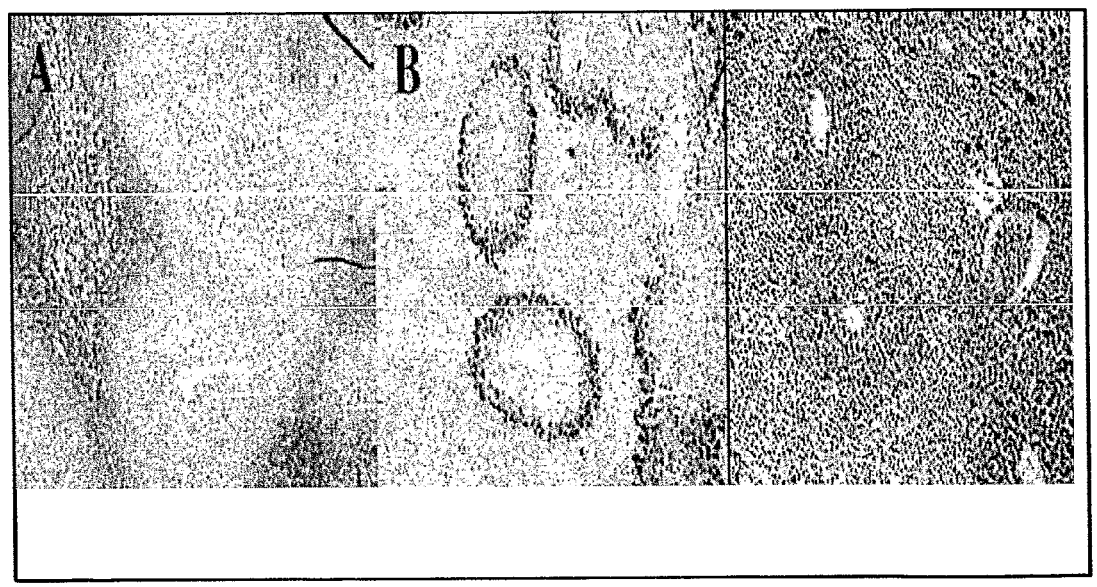
FIG. 17 illustrates pimonidazole staining of hypoxic areas in gliomas.

Glioma cell lines were developed that contain a bi-directional LacZ-HRE-firefly luciferase reporter. When xenografted into rat brains, the appearance of HIF activity can be monitored by bioluminescence imaging (BLI) (FIG. 16). BLI can be detected from about 8 days post-injection once tumors reach a critical size and hypoxia develops (FIG. 17). The tumors can be stained for hypoxia-induced LacZ expression.

Detection of hypoxic areas in xenografted gliomas with pimonidazole involves rodent injections with pimonidazole, a compound that binds to thiol-containing proteins in hypoxic cells and can be detected in tumor sections by immunohistochemistry. To demonstrate this technique, we show detection of hypoxic areas in sc. and ic. xenografts of human gliomas grown in rodents (FIG. 17).

Figure 18:
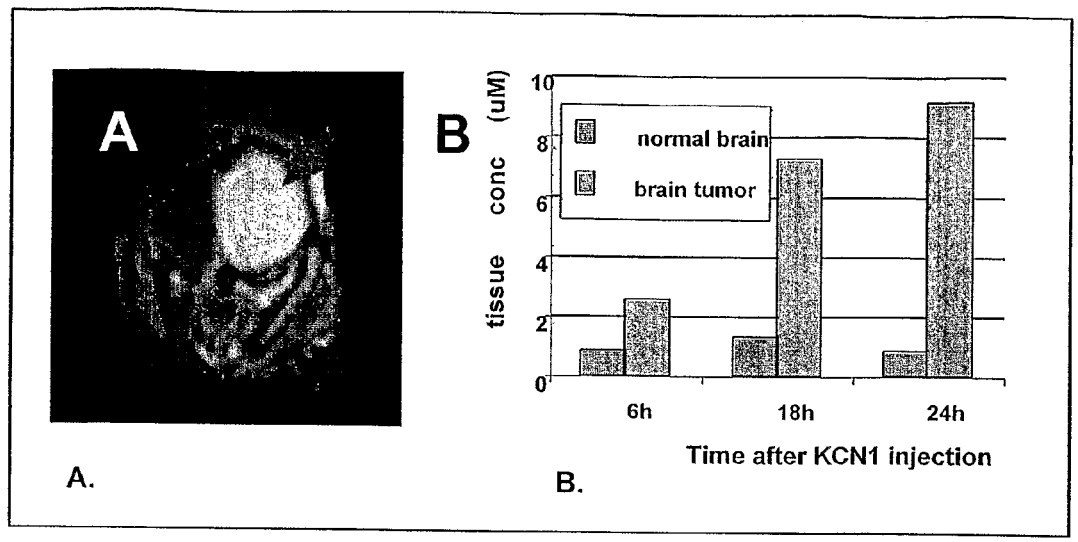
FIG. 18 illustrates a PK study of KCN1 in a brain tumor model.

The BBB may constitute an obstacle to drug delivery. To examine whether KCN1 would reside in the brain over a longer period of time and whether it would accumulate in higher amounts in the tumor versus normal brain we carried out a preliminary PK experiment. Nude mice carrying U87MG-EGFRvIII tumors were injected iv. with KCN1 and sacrificed at 6, 18 and 24 hrs. KCN1 concentration in the brain tumor and contra-lateral normal brain was performed by HPLC. This pilot experiment suggests that KCN1 reaches the brain and that it preferentially accumulates in and is retained in the brain tumor (FIG. 18).

Figure 19:
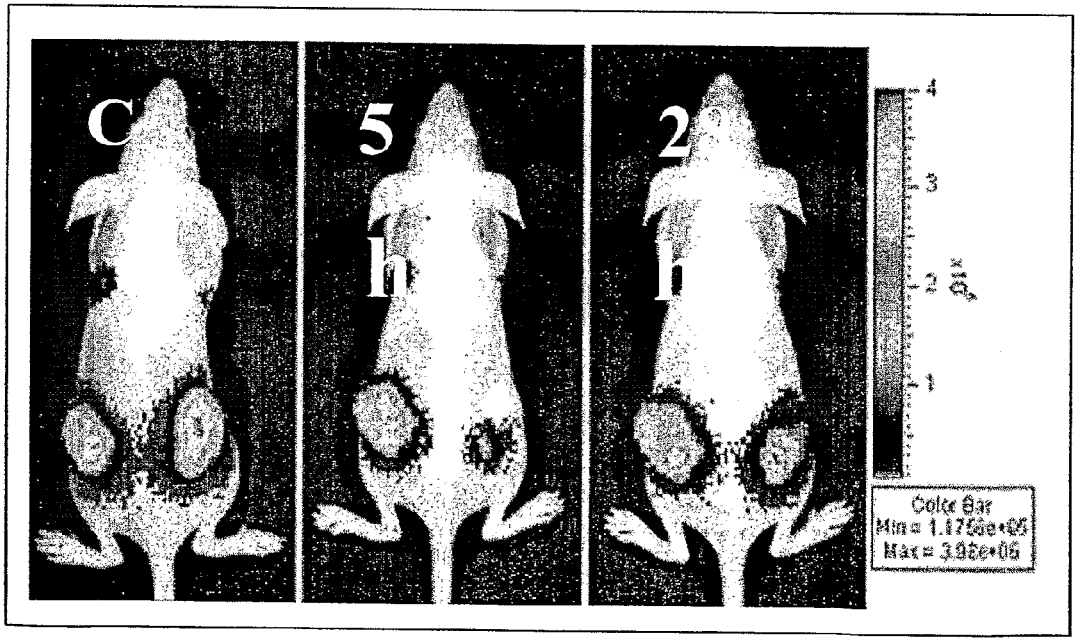
FIG. 19 illustrates a pharmacodynamic study of KCN1 in nu/nu mouse bearing LN229HRE-luci-ferase gliomas. KCN1 (2 mg) dissolved in DMSO was injected in the right hind tumor, and DMSO control in the left hind tumor. The mouse was injected with D-luciferin and imaged by BLI before FIG. 19 (C) and 5 & 28 hrs after injection. It should be noted strong reduction in HIF-dependent luciferase activity in right hind tumor at 5 hrs and partial recovery of HIF signaling after 28 hrs. (n=2). No change in luciferase activity was observed in vehicle-treated left tumor.

It is well appreciated that the efficacy of anti-cancer agents in rodents is an imprecise predictor of the success of these drugs in clinical trials. Therefore, evaluating the molecular and mechanistic end points of drug treatment is an important complementary approach to early pre-clinical studies. With this in mind, we sought to determine whether our lead HIF-1 pathway inhibitor (KCN1) can reduce HIF activity in a glioma xenograft model. In a pilot study, we used a mouse bearing 4 xenografts of LN229 cells containing a stable HIF responsive luciferase reporter (size-matched medium sized tumors in the back and small ones in the front). The HIF-dependent luciferase activity in the tumors was detected by non-invasive BLI. As expected, the larger hind tumors produced the strongest luciferase signal, likely due to the increase in the hypoxic volume. KCN1 was injected in the right hind tumor, and the left hind tumor with the vehicle (DMSO) as a control (frontal tumors were left untreated). 5 hrs later the mouse was re-examined by BLI, demonstrating a >90% reduction of the HIF-dependent luciferase activity in the KCN1-injected tumor, whereas the control tumor remained unchanged (FIG. 19). Luciferase activity recovered after 28 h, showing KCN1 did not reduce BLI signal by inducing acute tumor cell death. This experiment was repeated twice with similar results (not shown), strongly suggesting that KCN1 inhibits HRE activity in GBM cells in vivo.

Figure 20:
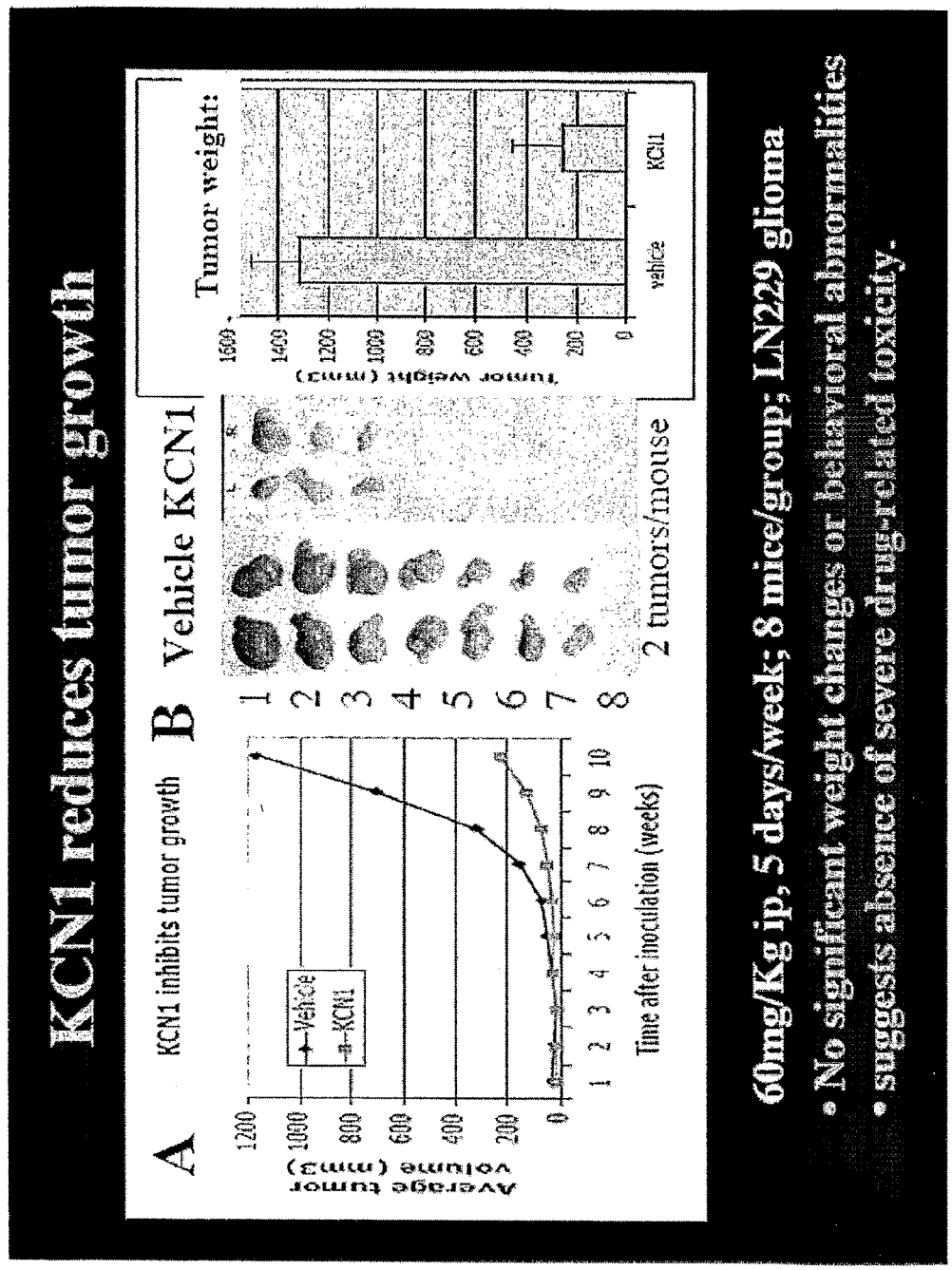
FIG. 20 illustrates that KCN1 inhibits sc LN229 glioma xenograft growth. LN-229 ($5 \times 10^6$) was implanted in both flanks of nude mice (8/group) and 1 week later started intraperitoneal injections of KCN1 (60 mg/kg; 5 days/week).

KCN1 was formulated in Cremaphor/EtOH for mice delivery and determined empirically (i.e., without prior understanding of its in vivo pharmacology) whether preliminary anti-tumorigenic effects could be observed. A strong and sustained inhibition of tumor growth was observed in the KCN1 treated animals (FIG. 20). An important conclusion from the above studies was also that KCN1 was found to be well tolerated, and no apparent toxicity was observed in it. and iv. (up to 100 mg/kg) injected animals.

Embodiments of the inhibitors can be modified to improve characteristics of the inhibitor. In an embodiment, the inhibitor can be defined into regions, such as the following: region I (the right-hand alkyl/aryl substituents), region II (acyl/sulfonyl substituent), and region III (the benzopyran aromatic ring system). The modification can include, but is not limited to, selecting compounds that have a "leaving" group such as a hydroxyl group, which will allow both augmentation of hydrophilicity (e.g., lower LogP) and permit the preparation of redox-sensitive prodrugs for hypoxia-targeting. This can be done to introduce a redox-sensitive prodrug moiety that can be cleaved through reduction under hypoxia. This is an attractive concept as it will allow for a synergistic effect: the molecular mechanism of hypoxia can be targeted and by using a hypoxia-sensitive prodrug also minimize potential toxicity to benign tissues.

Figure 21:
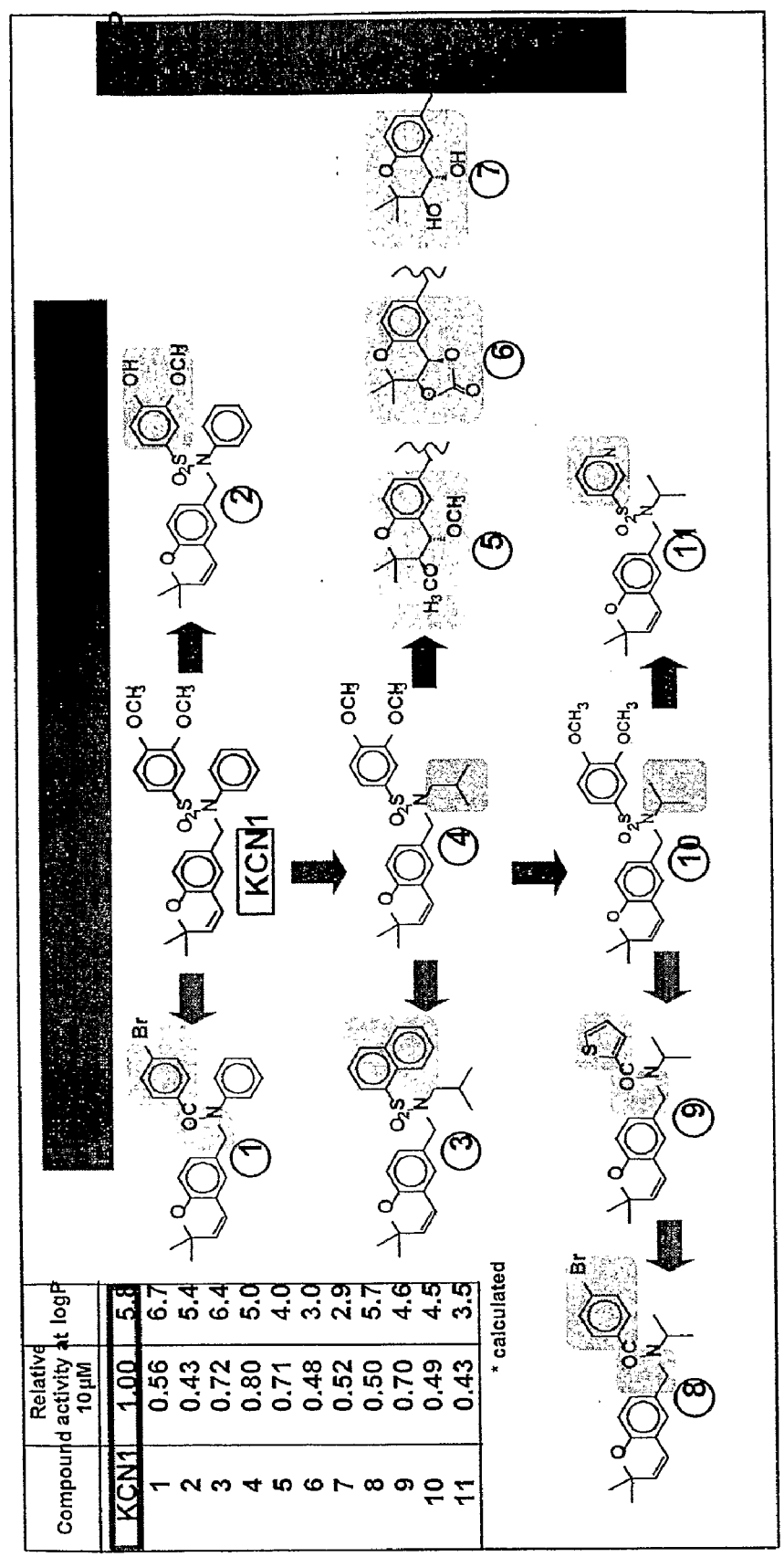
FIG. 21 illustrates structures of potent HIF-1 inhibitors generated by targeted chemical modification of KCN1. Four regions of KCN1 were systematically modified in our SAR studies (FIG. 21). The region(s) chemically distinct from the parental KCN1 molecule are highlighted in each structure. Using this approach, a pipeline of eleven potent inhibitors ($IC_{50}$<20 μM) with a broad range of logP values and solubility were generated. Arrows and gradient symbols indicate modification that increase (red) or decrease (blue) logP values. The table on the left lists the activities of each compound relative to KCN1, and their calculated logP.

The 2,2-dimethylbenzopyran scaffolds (region II) can be synthesized according to solid-phase and solution-phase methodologies (Nicolaou, K. C., Pfefferkorn, J. A., Mitchell, H. J., Roecker, A. J., Barluenga, S., Cao, G.-Q., Affleck, R. L. & Lillig, J. E. Natural product-like combinatorial libraries based on privileged structures. 2. Construction of a 10,000-membered benzopyran library by directed split-and-pool chemistry using NanoKans and optical encoding. *J Am Chem Soc* 122, 9954-67 (2000), which is incorporated herein by reference). These scaffolds, containing an aldehyde functionality, will be subsequently elaborated using short synthetic sequences which will diversify regions I and II: Grignard addition followed by acylation (class V); or, reductive amination followed by sulfonylation (class V). These methods are well-established, use commercially available building blocks and publications from our group have shown the feasibility of such chemistry. Further diversification on region III can be achieved elaborating on the carbon-carbon double bond of the pyran ring. These compounds will be synthesized using parallel synthesis, purified by common chromatographic techniques and characterized by LC- or GC-MS technologies. This resulted in KCN1 that is currently being further refined (FIG. 21). We will also examine whether we can further stabilize the central core of the molecule by replacing the sulfonamide bond with an amide, phosphonamide or related groups as described above. Nitroaryl compounds as redox triggers for the release of leaving groups attached to the benzylic position will be explored. This strategy requires a "leaving group" on the drug candidate such as a hydroxyl and we have already identified some active HIF inhibitors with hydroxy groups by SAR studies (FIG. 21 and data not shown).

In conclusion, it has been shown that: (i) biological reporter glioma cell lines were generated that reliably evaluate HIF transcriptional activity by measuring AlkPhos or luciferase; (ii) this reporter system was used for the screening of small-molecule HIF inhibitors; (iii) KCN1 suppress hypoxia induced increases in HIF-1α levels; (iv) methodologies were established to further examine the mechanism responsible for the inhibitors effects on translation, both through polyribosome analysis and signal transduction components controlling translation; (v) the HIF-responsive reporter system can be utilized in vivo to detect HIF activity non-invasively in the brain by BLI; (vi) intracranial glioma xenografts were performed, including histological analyses for β-gal expression, alkaline phosphatase expression and detection of hypoxic areas by pimonidazole IHC; (vii) HIF-1 was validated as an anti-tumor target using siRNA and virotherapy approaches; (viii) biodistribution of KCN1 was demonstrated in an intracerebrally-grown rat glioma, (ix) KCN1 injections decreases HIF-driven luciferase reporter gene activity in an in vivo tumor, and (xii) KCN1 can inhibit tumor growth in vivo.

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim:

1. A pharmaceutical composition comprising, a compound selected from one or more of the following:

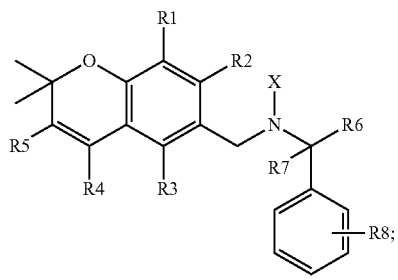

Formula A

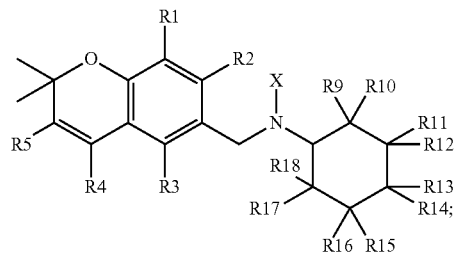

Formula B

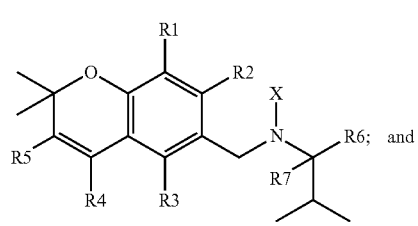

Formula C

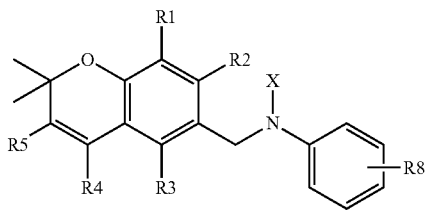

Formula D wherein X is selected from at least one of the following groups:

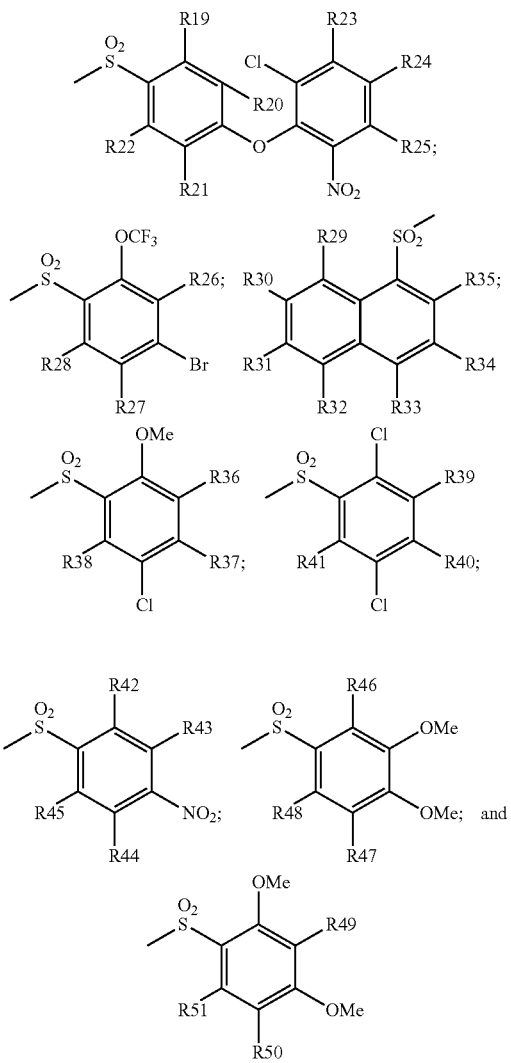

wherein R1, R2, R3, R4, R5, R6, R7, R8, R9, R10, R11, R12, R13, R14, R15, R16, R17, and R18, are each independently selected from the following groups: H, OH, a branched or unbranched $C_{1-12}$ alkyl group, an alkenyl group, an alkoxy group, an aryl group, a heterocycle group, an imidazole group, a substituted imidazole group, an alkyl substituted aryl group, a halogen substituted an aryl group, a halogen group, an amine group, $NO_2$, and an acyl group;

wherein R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, and R51 are each independently selected from the following groups: H, OH, a branched or unbranched $C_{1-12}$ alkyl group, an alkenyl group, an alkoxy group, an aryl group, a heterocycle group, an imidazole group, a substituted imidazole group, an alkyl substituted aryl group, a halogen substituted aryl group, a halogen group, an amine group, $NO_2$, and an acyl group;

or a pharmaceutically acceptable salt thereof.

2. A pharmaceutical composition comprising, one or more compounds selected from the following:

Formula E

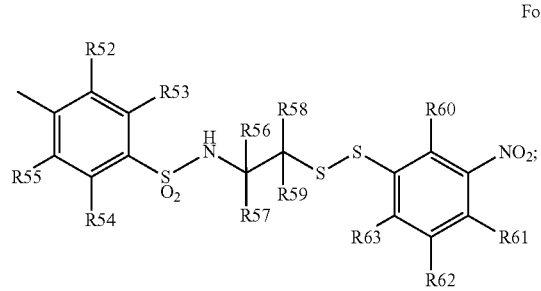

Formula F

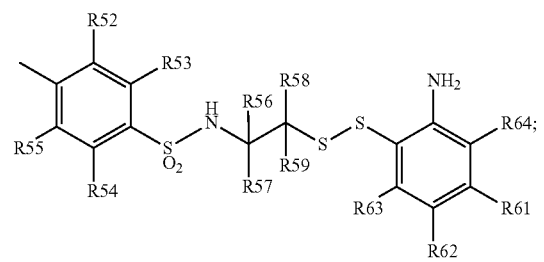

Formula G

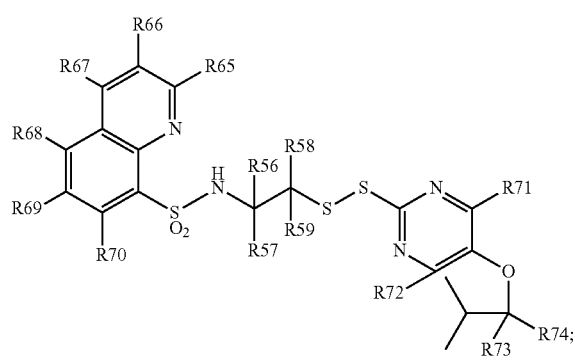

Formula H

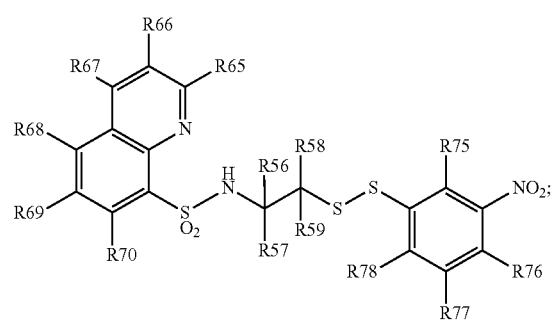

Formula I

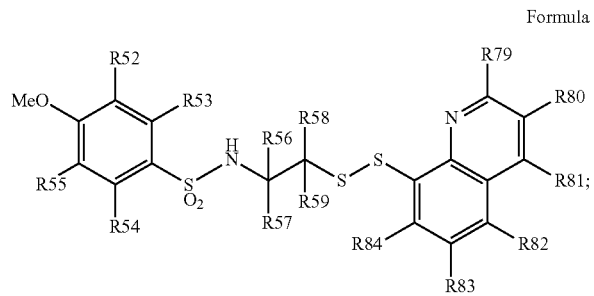

Formula J

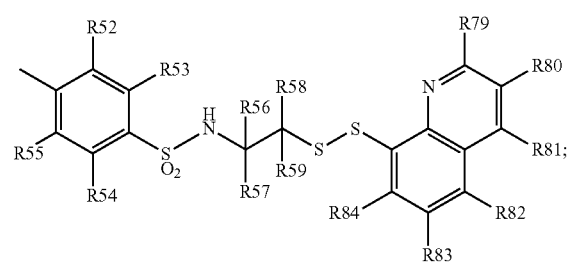

Formula K

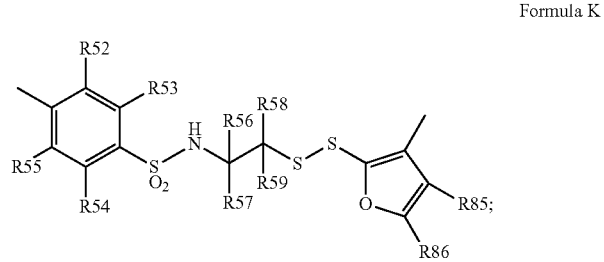

Formula L

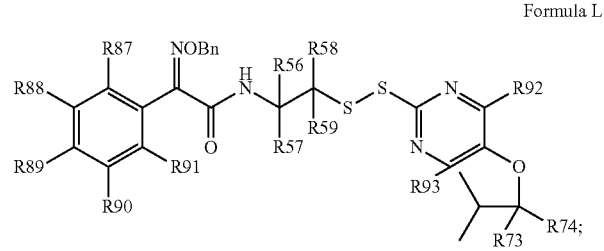

-continued
Formula M
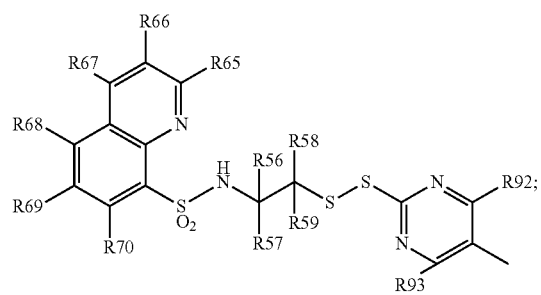
Formula N
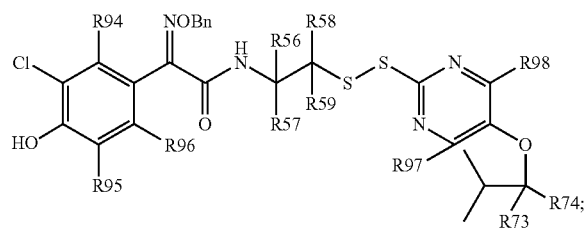
Formula O
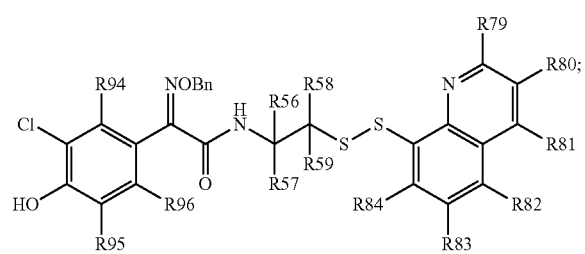
Formula P
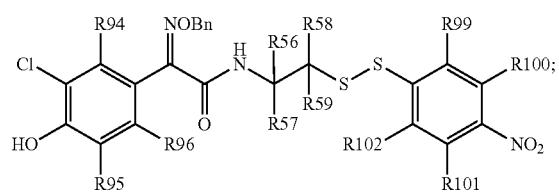
Formula Q
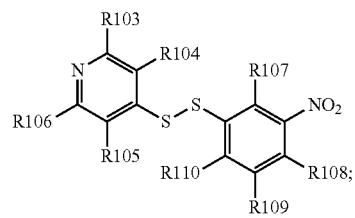
Formula R
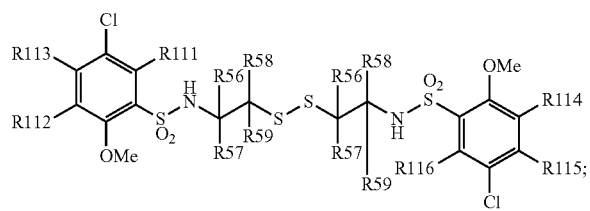
Formula S
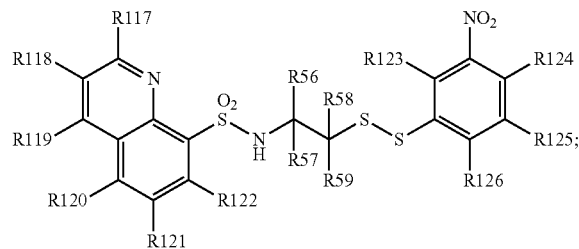
Formula T
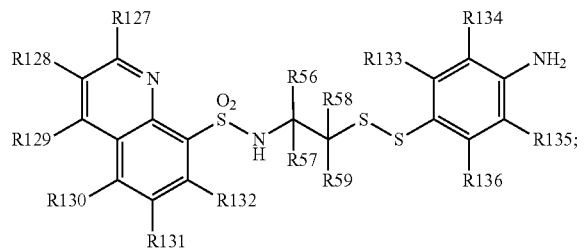
Formula U
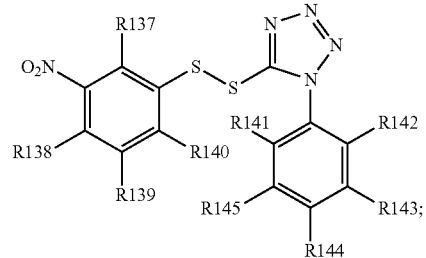
Formula V
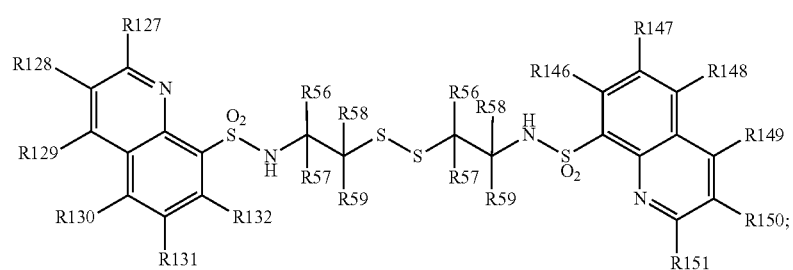

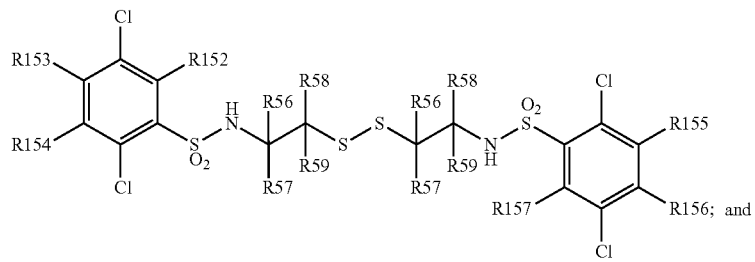

Formula W

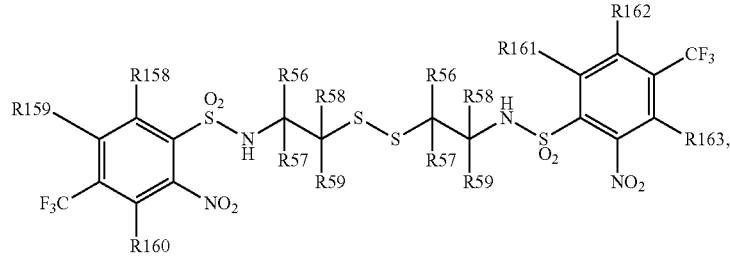

Formula X wherein R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89, R90, R91, R92, R93, R94, R95, R96, R97, R98, R99, R100, R101, R102, R103, R104, R105, R106, R107, R108, R109, R110, R11, R112, R113, R114, R115, R116, R117, R118, R119, R120, R121, R122, R123, R124, R125, R126, R127, R128, R129, R130, R131, R132, R133, R134, R135, R136, R137, R138, R139, R140, R141, R142, R143, R144, R145, R146, R147, R148, R149, R150, R151, R152, R153, R154, R155, R156, R157, R158, R159, R160, R161, R162, and R163, are each independently selected from the following groups: H, OH, a branched or unbranched $C_{1-12}$ alkyl group, an alkenyl group, an alkoxy group, an aryl group, a heterocycle group, an imidazole group, a substituted imidazole group, an alkyl substituted aryl group, a halogen substituted aryl group, a halogen group, an amine group, $NO_2$, and an acyl group;

or a pharmaceutically acceptable salt thereof.

3. The pharmaceutical composition of claim 1, further comprising a second therapeutic compound.

4. The pharmaceutical composition of claim 3, wherein the second therapeutic compound is an antibody, antibiotic, anti-inflammatory, anti-oxidant, analgesic, radioisotope, noscapine, paclitaxel, nocodazole, vinca alkaloids, adriamycin, alkeran, Ara-C, BiCNU, busulfan, CCNU, carboplatinum, cisplatinum, cytoxan, daunorubicin, DTIC, 5-FU, fludarabine, hydrea, idarubicin, ifosfamide, methotrexate, mithramycin, mitomycin, mitoxantrone, nitrogen mustard, velban, vincristine, VP-16, gemcitabine, herceptin, irinotecan, camptosar, CPT-11, leustatin, navelbine, rituxan, STI-571, taxotere, temozolomide, topotecan, hycamtin, xeloda, capecitabine, zevelin, and combinations thereof.

5. The pharmaceutical composition of claim 2, further comprising a second therapeutic compound.

6. The pharmaceutical composition of claim 5, wherein the second therapeutic compound is an antibody, antibiotic, anti-inflammatory, anti-oxidant, analgesic, radioisotope, noscapine, paclitaxel, nocodazole, vinca alkaloids, adriamycin, alkeran, Ara-C, BiCNU, busulfan, CCNU, carboplatinum, cisplatinum, cytoxan, daunorubicin, DTIC, 5-FU, fludarabine, hydrea, idarubicin, ifosfamide, methotrexate, mithramycin, mitomycin, mitoxantrone, nitrogen mustard, velban, vincristine, VP-16, gemcitabine, herceptin, irinotecan, camptosar, CPT-11, leustatin, navelbine, rituxan, STI-571, taxotere, temozolomide, topotecan, hycamtin, xeloda, capecitabine, zevelin, and combinations thereof.

7. A method of modulating HIF activity in a cell comprising: contacting the cell with a HIF inhibiting amount of the compositions of claim 2.

8. A method of treating cancer or a tumor in a host comprising administering to the host a HIF inhibiting amount of the compositions of claim 2 wherein the cancer or tumor is selected from the group consisting of cervical, ovarian, colon, breast, gastric, lung, skin, ovarian, pancreatic, prostate, and renal cancer.

9. A pharmaceutical composition of claim 1, wherein the compound of Formula B is N-cyclohexyl-N-((2,2-dimethyl-2H-chromen-6-yl)methyl)-2,4-dimethoxybenzenesulfonamide or salt thereof.

10. A pharmaceutical composition of claim 1, wherein the compound of Formula C is N-((2,2-dimethyl-2H-chromen-6-yl)methyl)-N-isobutyl-3,4-dimethoxybenzenesulfonamide or salt thereof.

11. A pharmaceutical composition of claim 1, wherein the compound of Formula D is N-((2,2-dimethyl-2H-chromen-6-yl)methyl)-3,4-dimethoxy-N-phenylbenzenesulfonamide or salt thereof.

* * * * *

UNITED STATES PATENT AND TRADEMARK OFFICE
CERTIFICATE OF CORRECTION

PATENT NO.       : 8,071,795 B2
APPLICATION NO.  : 11/997809
DATED            : December 6, 2011
INVENTOR(S)      : Erwin G Van Meir and Kyriacos Nicolaou It is certified that error appears in the above-identified patent and that said Letters Patent is hereby corrected as shown below:

Col. 1, immediately below the subtitle, "Statement Regarding Federally Funded Research," please replace line 16 thru 18 with the following:

--This invention was made with government support under Grant No. CA086335, awarded by the National Institutes of Health. The government has certain rights in the invention.--

Signed and Sealed this
Seventh Day of February, 2012

David J. Kappos
*Director of the United States Patent and Trademark Office*